United States Patent
Price et al.

(10) Patent No.: US 11,773,398 B2
(45) Date of Patent: Oct. 3, 2023

(54) MODIFIED EXCISABLE 5307 MAIZE TRANSGENIC LOCUS LACKING A SELECTABLE MARKER

(71) Applicant: INARI AGRICULTURE TECHNOLOGY, INC., Cambridge, MA (US)

(72) Inventors: Joshua L. Price, Cambridge, MA (US); Michael Andreas Kock, Rheinfelden (DE); Michael Lee Nuccio, Salem, NH (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/058,161

(22) Filed: Nov. 22, 2022

(65) Prior Publication Data
US 2023/0077473 A1   Mar. 16, 2023

Related U.S. Application Data

(63) Continuation of application No. PCT/US2021/043483, filed on Jul. 28, 2021.
(Continued)

(51) Int. Cl.
*C12N 15/82* (2006.01)
*C12Q 1/6895* (2018.01)
(Continued)

(52) U.S. Cl.
CPC .......... *C12N 15/8201* (2013.01); *A01H 5/10* (2013.01); *A01H 6/4684* (2018.05); *A01H 6/542* (2018.05);
(Continued)

(58) Field of Classification Search
None
See application file for complete search history.

(56) References Cited

U.S. PATENT DOCUMENTS 7,632,985 B2   12/2009 Malven et al.
7,956,246 B2    6/2011 Bing et al.
(Continued)

FOREIGN PATENT DOCUMENTS

| CN | 104830860 A | 8/2015 |
| WO | 2022026375 A1 | 2/2022 |

(Continued)

OTHER PUBLICATIONS

Yau & Stewart "Less is more: strategies to remove marker genes from transgenic plants" 2013 BMC Biotechnology 13:36 (23 total pages). (Year: 2013).*

(Continued)

*Primary Examiner* — Matthew R Keogh
*Assistant Examiner* — Rebecca Stephens
(74) *Attorney, Agent, or Firm* — McKee, Voorhees & Sease, PLC

(57) ABSTRACT

Transgenic INIR17 maize plants comprising an ecry3.1Ab expression cassette linked to a secondary nopaline synthase terminator element which lack a selectable marker gene and/or which comprise modifications that provide for facile excision of the INIR17 transgenic locus from the maize plant genome are provided. Genomic DNA of INIR17 transgenic plants, detection of INIR17 plants and products thereof, methods of making INIR17 plants, and use of INIR17 plants to facilitate breeding are disclosed.

12 Claims, 17 Drawing Sheets

Figure 1:
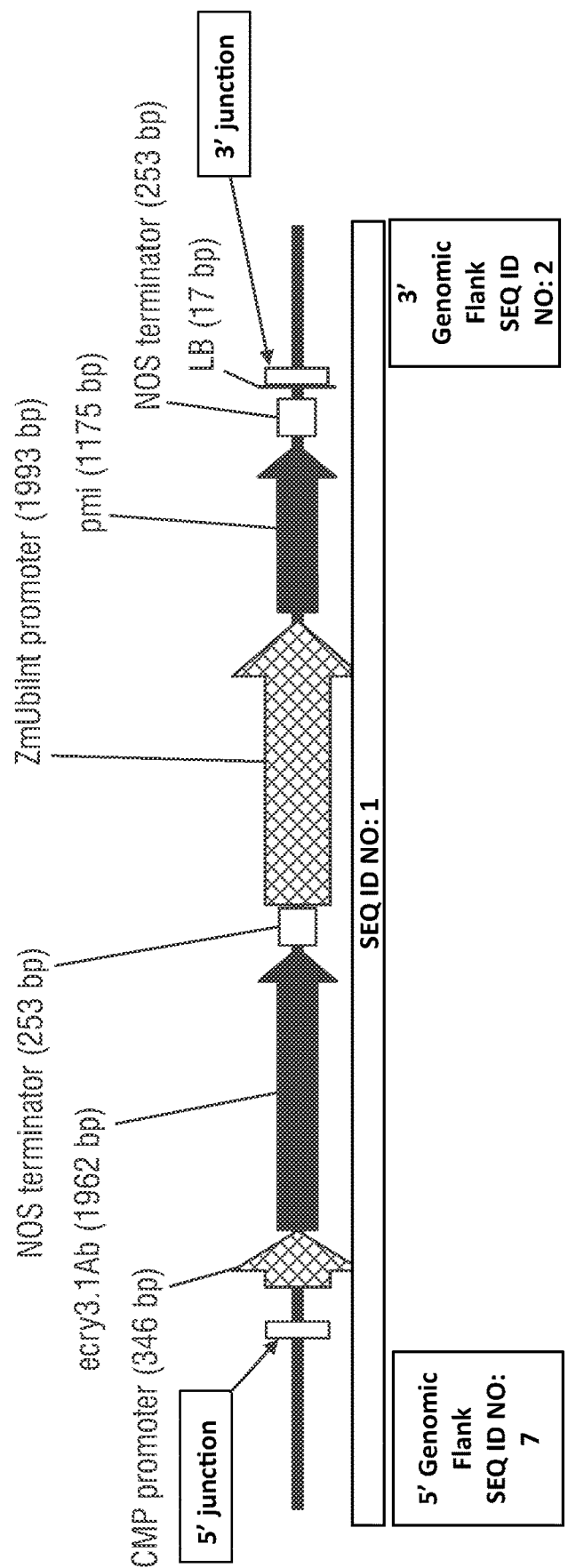

Specification includes a Sequence Listing.

Event 5307

Related U.S. Application Data

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,949, filed on Feb. 4, 2021, provisional application No. 63/199,951, filed on Feb. 4, 2021, provisional application No. 63/199,930, filed on Feb. 3, 2021, provisional application No. 63/059,916, filed on Jul. 31, 2020, provisional application No. 63/059,963, filed on Jul. 31, 2020, provisional application No. 63/059,860, filed on Jul. 31, 2020, provisional application No. 63/059,813, filed on Jul. 31, 2020.

(51) Int. Cl.
| | |
|---|---|
| *C12N 9/22* | (2006.01) |
| *C12N 15/11* | (2006.01) |
| *A01H 6/54* | (2018.01) |
| *A01H 5/10* | (2018.01) |
| *C12Q 1/6834* | (2018.01) |
| *A01H 6/46* | (2018.01) |

(52) U.S. Cl.
CPC ............ *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01)

(56) References Cited

U.S. PATENT DOCUMENTS

| | | | |
|---|---|---|---|
| 8,232,456 | B2 | 7/2012 | Long et al. |
| 8,450,561 | B2 | 5/2013 | Beazley et al. |
| 8,455,198 | B2 | 6/2013 | Gao et al. |
| 8,455,720 | B2 | 6/2013 | Long et al. |
| 8,466,346 | B2 * | 6/2013 | DeFramond ....... C12N 15/8286 514/4.5 |
| 8,575,434 | B2 | 11/2013 | Diehn et al. |
| 8,680,363 | B2 | 3/2014 | Bard et al. |
| 9,187,756 | B2 | 11/2015 | Nuccio |
| 9,428,765 | B2 | 8/2016 | Anderson et al. |
| 9,447,428 | B2 | 9/2016 | Brinker et al. |
| 9,540,655 | B2 | 1/2017 | Cui et al. |
| 9,738,904 | B2 | 8/2017 | Cui et al. |
| 9,944,944 | B2 | 4/2018 | Cui et al. |
| 11,041,172 | B2 | 6/2021 | Cermak |
| 11,214,811 | B1 | 1/2022 | Nuccio et al. |
| 11,242,534 | B1 | 2/2022 | Nuccio et al. |
| 11,359,210 | B2 | 6/2022 | Price et al. |
| 2003/0088081 | A1 | 5/2003 | Maliga et al. |
| 2010/0162428 | A1 | 6/2010 | Brown et al. |
| 2011/0191877 | A1 | 8/2011 | Russell et al. |
| 2011/0191899 | A1 | 8/2011 | Ainley et al. |
| 2013/0333071 | A1 | 12/2013 | Boukharov et al. |
| 2014/0162272 | A1 | 6/2014 | Long et al. |
| 2014/0196169 | A1 | 7/2014 | D'Halluin et al. |
| 2015/0059010 | A1 | 2/2015 | Cigan et al. |
| 2015/0082478 | A1 | 3/2015 | Cigan et al. |
| 2016/0333363 | A1 | 11/2016 | Srivastava |
| 2017/0166912 | A1 | 6/2017 | Brower-Toland et al. |
| 2018/0057878 | A1 | 3/2018 | Bing et al. |
| 2018/0163218 | A1 | 6/2018 | Corbin et al. |
| 2019/0136249 | A1 | 5/2019 | Sakai et al. |
| 2019/0284644 | A1 | 9/2019 | Mackenzie et al. |
| 2019/0320607 | A1 | 10/2019 | Christensen et al. |
| 2019/0352655 | A1 | 11/2019 | Niu et al. |
| 2020/0157554 | A1 | 5/2020 | Cigan et al. |
| 2020/0399626 | A1 | 12/2020 | Liu et al. |
| 2020/0405649 | A1 | 12/2020 | Wang et al. |
| 2021/0274783 | A1 | 9/2021 | Chae |
| 2022/0030806 | A1 | 2/2022 | Price et al. |
| 2022/0030822 | A1 | 2/2022 | Nuccio et al. |
| 2022/0033833 | A1 | 2/2022 | Gilbertson et al. |
| 2022/0033836 | A1 | 2/2022 | Price et al. |
| 2022/0098602 | A1 | 3/2022 | Nuccio et al. |
| 2022/0154194 | A1 | 5/2022 | Nuccio et al. |
| 2022/0251584 | A1 | 8/2022 | Nuccio et al. |
| 2022/0364105 | A1 | 11/2022 | Price et al. |
| 2023/0077473 | A1 | 3/2023 | Price et al. |
| 2023/0078387 | A1 | 3/2023 | Kock et al. |
| 2023/0083144 | A1 | 3/2023 | Nuccio et al. |
| 2023/0087222 | A1 | 3/2023 | Kock et al. |
| 2023/0147013 | A1 | 5/2023 | Nuccio et al. |

FOREIGN PATENT DOCUMENTS

| | | |
|---|---|---|
| WO | 2022026379 A1 | 2/2022 |
| WO | 2022026390 A1 | 2/2022 |
| WO | 2022026395 A2 | 2/2022 |
| WO | 2022026403 A2 | 2/2022 |
| WO | 2022026540 A1 | 2/2022 |
| WO | 2022026801 A1 | 2/2022 |
| WO | 2022026841 A2 | 2/2022 |

OTHER PUBLICATIONS

Gleditzsch et al. "PAM identification by CRISPR-Cas effector complexes: diversified mechanisms and Structures" 2019 RNA Biology 16(4): 504-517. (Year: 2019).*
Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.
Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.
Bissler, J.J., "Triplex DNA and human disease," Frontiers in Bioscience, May 1, 2007, vol. 12, pp. 4536-4546.
Bortesi et al., "The CRISPR/Cas9 system for plant genome editing and beyond," Biotechnology Advances, Dec. 20, 2014, vol. 33, Issue 1, pp. 41-52.
Charpentier et al., "Biogenesis pathways of RNA guides in archaeal and bacterial CRISPR-Cas adaptive immunity," FEMS Microbiology Reviews, May 19, 2015, vol. 39, Issue 3, pp. 428-441.
Cho et al., "Nonallelic homologous recombination events responsible for copy number variation within an RNA silencing locus," Plant Direct, vol. 3, Aug. 27, 2019, 16 pages.
Du et al., "Construction of Marker-Free Genetically Modified Maize Using a Heat-Inducible Auto-Excision Vector," Genes, May 17, 2019, vol. 10, No. 374, 17 pages.
Du et al., "Infection of Embryonic Callus with *Agrobacterium* Enables High-Speed Transformation of Maize," International Journal of Molecular Sciences, Jan. 11, 2019, vol. 20, No. 279, 15 pages.
Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.
Gurusaran et al., "RepEx: Repeat extractor for biological sequences," Genomics, Jul. 21, 2013, vol. 102, pp. 403-408.
International Searching Authority in connection with PCT/US21/43897 filed Jul. 30, 2021, "Invitation to Pay Additional Fees And, Where Applicable, Protest Fee," mailed Oct. 27, 2021, 3 pages.
International Searching Authority in connection with PCT/US21/43935 filed Jul. 30, 2021, "Invitation to Pay Additional Fees And, Where Applicable, Protest Fee," mailed Oct. 26, 2021, 3 pages.
International Searching Authority in connection with PCT/US21/43945 filed Jul. 30, 2021, "Invitation to Pay Additional Fees And, Where Applicable, Protest Fee," mailed Oct. 27, 2021, 3 pages.

(56) References Cited

OTHER PUBLICATIONS

Kim et al., "CRISPR/Cpf1-mediated DNA-free plant genome editing," Nature Communications, Feb. 16, 2017, vol. 8, Article No. 14406, 7 pages.

Li et al., "Expanding the Scope of CRISPR/Cpf1-Mediated Genome Editing in Rice," Molecular Plant, Jul. 2, 2018, vol. 11, No. 7, pp. 995-998, 14 pages.

Luo et al., "Improperly Terminated, Unpolyadenylated mRNA of Sense Transgenes is Targeted by RDR6-Mediated RNA Silencing in *Arabidopsis*," The Plant Cell, Mar. 23, 2007, vol. 19, pp. 943-958.

Malzahn et al., "Application of CRISPR-Cas12a temperature sensitivity for improved genome editing in rice, maize, and *Arabidopsis*," BMC Biology, Jan. 31, 2019, vol. 17, No. 9, 14 pages.

Non-Final Office Action in U.S. Appl. No. 17/248,936, dated Mar. 25, 2021, 25 pages.

Non-Final Office Action in U.S. Appl. No. 17/249,640, dated Jun. 29, 2021, 10 pages.

Non-Final Office Action in U.S. Appl. No. 17/302,110, dated Jun. 29, 2021, 22 pages.

Non-Final Office Action in U.S. Appl. No. 17/302,121, dated Jul. 8, 2021, 10 pages.

Non-Final Office Action in U.S. Appl. No. 17/302,739, dated Aug. 3, 2021, 24 pages.

Notice of Allowance in U.S. Appl. No. 17/249,640, dated Sep. 22, 2021, 7 pages.

Que et al., "Maize transformation technology development for commercial event generation," Frontiers in Plant Science, Aug. 5, 2014, vol. 5, Article No. 379, 19 pages.

Srivastava et al., "Gene Stacking by recombinases," Plant Biotechnology Journal, Feb. 2016, vol. 14, pp. 471-482.

Srivastava, et al., "Dual-targeting by CRISPR/Cas9 for precise excision of transgenes from rice genome," Plant Cell Tissue and Organ Culture, Jan. 20, 2017, vol. 129, pp. 153-160.

Ward et al., "Petition for Determination of Nonregulated Status for Insect-Resistant MIR162 Maize," Syngenta Biotechnology, Inc., Aug. 31, 2007, 271 pages.

"What is a CRISPR-Cas system?," CRISPR-Cas++, Universite Paris-Saclay, accessed Nov. 2, 2021. Retrieved from the Internet <URL:https://crisprcas.i2bc.paris-saclay.fr/Home/About>, 2 pages.

Xing et al., "Revealing frequent alternative polyadenylation and widespread low-level transcription read-through of novel plant transcription terminators," Plant Biotechnology Journal, Sep. 2010, vol. 8, pp. 772-782.

Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.

Danilo et al., "The DFR locus: A smart landing pad for targeted transgene insertion in tomato," PLoS One, Dec. 6, 2018, vol. 13, No. 12, 14 pages.

Eaglesham et al., "New DNA-Editing Approaches: Methods, Applications & Policy for Agriculture," North American Agricultural Biotechnology Council Report, NABC Report 26, 2014, 255 pages.

Rudgers et al., "EXZACTTM Precision Technology: Scientific and Regulatory Advancements in Plant-Genome Editing with ZFNs," North American Biotechnology Council, 2014, pp. 113-124.

Shi et al., "ARGOS8 variants generated by CRISPR-Cas9 improve maize grain yield under field drought stress conditions," Plant Biotechnology Journal, 2017, vol. 15, pp. 207-216.

Office Action in U.S. Appl. No. 18/058,081, dated Apr. 11, 2023, 27 pages.

Office Action in U.S. Appl. No. 18/058,156, dated May 19, 2023, 32 pages.

Begemann et al., "Precise insertion and guided editing of higher plant genomes using Cpf1 CRISPR nucleases," Scientific Reports, Sep. 14, 2017, vol. 7, No. 11606, pp. 1-6.

Begemann et al., "Supplementary Data—Precise insertion and guided editing of higher plant genomes using Cpf1 CRISP nucleases," Scientific Reports, Sep. 14, 2017, vol. 7, No. 11606, pp. 1-6.

Forsyth et al., "Transcription Activator-Like Effector Nucleases (TALEN)-Mediated Targeted DNA Insertion in Potato Plants," Frontiers in Plant Science, Oct. 2016, vol. 7, No. 1572, pp. 1-12.

International Search Report in PCT/US2021/043161, dated Jan. 5, 2022, 6 pages.

International Search Report in PCT/US2021/043170, dated Jan. 5, 2022, 6 pages.

International Search Report in PCT/US2021/043187, dated Jan. 6, 2022, 6 pages.

International Search Report in PCT/US2021/043192, dated Jan. 5, 2022, 7 pages.

International Search Report in PCT/US2021/043207, dated Jan. 27, 2022, 6 pages.

International Search Report in PCT/US2021/043440, dated Dec. 2, 2021, 3 pages.

International Search Report in PCT/US2021/043468, dated Nov. 26, 2021, 4 pages.

International Search Report in PCT/US2021/043479, dated Nov. 23, 2021, 3 pages.

International Search Report in PCT/US2021/043483, dated Dec. 16, 2021, 3 pages.

International Search Report in PCT/US2021/043496, dated Dec. 1, 2021, 4 pages.

International Search Report in PCT/US2021/043851, dated Dec. 30, 2021, 6 pages.

International Search Report in PCT/US2021/043919, dated Jan. 20, 2022, 8 pages.

International Search Report in PCT/US2021/043933, dated Dec. 30, 2021, 6 pages.

International Search Report in PCT/US2021/044198, dated Jan. 19, 2022, 6 pages.

Mookan et al., "Selectable marker independent transformation of recalcitrant maize inbred B73 and sorgum P898012 mediated by morphogenic regulators Baby Boom and WUSCHEL2," Plant Cell Reports, 2017, vol. 36, pp. 1477-1491.

Non-Final Office Action in U.S. Appl. No. 17/680,647, dated Jun. 23, 2022, 11 pages.

Non-Final Office Action in U.S. Appl. No. 18/057,860, dated Jun. 1, 2023, 49 pages.

Non-Final Office Action in U.S. Appl. No. 18/057,867, dated Jun. 7, 2023, 17 pages.

Non-Final Office Action in U.S. Appl. No. 18/058,144, dated Jun. 7, 2023, 49 pages.

Non-Final Office Action in U.S. Appl. No. 18/162,134, dated Jun. 21, 2023, 28 pages.

Notice of Allowance in U.S. Appl. No. 17/248,936, dated Mar. 10, 2022, 7 pages.

Zhang et al., "Off-target Effects in CRISPR/Cas9-mediated Genome Engineering," Molecular Therapy Nucleic Acids, 2015, vol. 4, No. e264, pp. 1-8.

Zhong et al., "Plant genome editing using FnCpf1 and LbCpf1 nucleases at redefined and altered PAM sites," Molecular Plant, 2018, vol. 11, No. 7, pp. 999-1002.

Zhong et al., "Supplementary Data—Plant genome editing using FnCpf1 and LbCpf1 nucleases at redefined and altered PAM sites," Molecular Plant, 2018, vol. 11, No. 7, pp. 999-1002.

\* cited by examiner

FIG. 7B

```
TACAAGAATATTGAGAGCGTGAGTACATAGCAGCATTGCATTAGCAAGCATTTCATTAGCAAGCATTTCAAAAGAATTAATTTCTCATAGCAAGTG
ATATCTCTCCTCACGCTCAATCTTCAGTTCCTCATGTAGAGCACATATGTCCATCCACAAATCATGACAATTTTATGGTTTCTAAC
TCTATTAAACACATCTTTGCAAAGGCCCTCTAAAAGGGTGTTTTGGCCTTAGCATTCTCATAGTTCAACTCTTCACCTAC
AAGATTTGTGTGGATCTCTAGGTTCGGGGAATCTTTGTGTGGCGGGCTTGTAGACACCAATGTCTATAGCCTCTAAATATGCTTCC
ATACGAATTTTCCAATATGGAAAATCGTCACCATAAAAAACGGGAGAAGGTCCATCCCCACGGACATCGTTACTCTAGCGGTTA
AGCTAATCTAAGACAACAAGGCTCTTATACCAATTGAAAGGATCACGATGCCCAAGAGGGGGGTTGAATTGGGCTTTTCTAAA
AATCAACACTAACTAAAATCTAAGCAAGAGCCCAACTTCACCCCGACACTTCACCCCGACAACTAGCACTAAGAGAATAATACTAGAAATACAACAATG
CTAAGATAATACTTCAATACTTGCTAAACAATACACAATGTAAAATACTTGAATTAAGTGCGAATGTAAAGCAAGGTTTAGAAG
ACTCCTCCAATTTTCTAGAGGTATCAAAGAGTCGGCACTCTCCCCTAGTCCTCGTTGGAGCACCTGCGTAAGGGTATCGCTCTC
CCTTGGTCATCGCAAGAACCAAGTGCTCACACAGAGATGATCCTTTGCCACTCCGGGACGCTCCCAAGCGCTCTAGGTGATGCCGATCA
AACTTGAGTCGGGTCACCAACAAGATCTCCACGTGACCAAGAAGCCTAATGCATGCGGGTGTGTGCTAGGTGGCTCTCGCTAGCG
CCAAGAGTAATAAGCCATAGCTTTCACTTGACCAAGAAGCCTAATGCATGCGGGTGTGTGGCTTGTGGTGCTTGCAATGCTCTACCAATGTGTAGG
TTAATGAGGTCCAAATGCGGGATTAAGATTCTCAAGTCACCTCACTAGGTGATGGGGTATAAATAGCCCTCACCACCACCAACTAGCCATTACCAGGA
AGTAAATGTGGGCAGCAAGAACCATCAATATGGTAGGTGGATGGGGTATAAATAGCCCTCACCACCAACTAGCCATTACCAGGA
ATCTGCTGCGCATGGGCGCACCGGACAGTCCGGTGTCGCCAACGGTCCGGTGCCAACGTGCGACTCAAACGGCTAGTTCTGACAGCT
AGCCGTTGACAGATGGCATACCGGACAGTCCGATACGCTGTCCGGTGTCGCCAACGTGCGACTCAAACGGCTAGTTCTGACAGCT
ACTGAAGGCGGGAAACGACAATCTGATCATGAGCGGAGAATTAAGGGAGTCACGTTATGACCCCGCCGATGACGCGGACAA
GCCGTTTACGTTTGGAACTGGAACGGCCAACGCTGCAGGAATTGGCCGCAGCTGCCATTAAATCAATTGGGCGCCGGAA
TTCGAGCTCGGTACAAGCTTCTGGCAGACAAAGTGCAGACATACTGTCCCACAAATGAAGATGAATCTGTAAAGAAAACGC
GTGAAATAATGCGTCTGACAAGGTTAGGTGCGGTCTGCCTTTAATCAATACCAAAGTGGTCCTACCACGATGGAAAACTGTGCA
GTCGGTTTGGCTTTTTCTGACGAACAACAAATAAGATTCGTGGCCGACAGGTGGGGGTCCACCATGTGAAGGCATCTCAGACTCCA
ATAATGGAGCAATGACGTAAGGGCTTACGAAATAAGGGTAGTTTGGGAAATGTCCACTCACCCGTCAGTCTATAAATACTT
AGCCCCTCCCTCATTGTTAAGGAGCAAGGATCCACCATGACTAGTAGTAACGGCGCAACGTGTGTCGCCCTTATGACGG
CCGACAACAACCGGACCGGAAACCAAGGAGCAGCAGCAGCAAGGACGTGATCACCACCAAGGACGTGATCAGCGTGGTGGGGCGACCTGCTG
GGCGTGGTGGGCTTCCCCTTCGGCGGCTTCCCCTTCGGCGGCAGGTGGAGGCCGCCGCTGGTGAGCTTCTACACCAACCATCTGGCCCAGCAGGACCCC
CTGGAAGGCCTTCATGGACCAGGTGGAGGCCGCCAGAAGATCGCCGACCAGAAGATCGCCGACTACGCCAGAAGAACCCGCTGTTCCGCAA
CTACAGGGCCCTCCAGAACAACGTGGAGGACTATGTGAGCGCCCTGAGCAGCCCTGAGCGCCCCAGCCGGGAGAGCCTGAGCGCCCCCCCC
CCCCACACAGCAGGGCCAGCCCGCATCCGCGAGCTGTTCAGCCAGGCCGAGCCGAGCACTTCCGCAACAGCATGCCAGCTTCGCCATC
AGCGGCTACGAGGTGCTGTTCCTGACCACCTACGACAGCGAGAAGGACACTCGCGCCGAGTTCTACAAGCGCCGAGTACACCGAC
CACTGCGTGAAGTGGTACAACGTGGGGCTACGAGAAGGACACTCGCGCCGAGTTCTACAAGCGCCGAGTACACCGAC
CCGCGAGATGACCCTGACCGTGCTGACCCTGGACCTGGACCTGGACCCTGTACCGACGTGCGCCTGTACCCCAAGGAGGTGAAGA
```

FIG. 8A

CCGAGCTGACCCGCGACGTGCTGACCGACCCCATCGTGGGCGTGAACAACCTGCGCGGCTACGGCCACCACCTTCAGCAACAT
CGAGAACTACATCCGCAAGCCCACCTGTTCGACTACCTGAGCGCATCCAGTTCCACACGCGTTTCCAGCCGGCTACGG
CAACGACAGCTTCAACTACTGGAGCGGCAACTACGTGAGCGAACCTGAGTTGCAGCCCCAGCATCGGCAGCAACGACATCATCACCAGCCCT
TCTACGGCCGTGTGCCGGAGCAGCCGTGCAGAGGCCTTGAGTTCAAGGCGAGAAGGTGTACCGCGTGGCTAACACCAAC
CTGGCCGTGTGCCCTCTGCACCACGACAAGAGCCGGTGTACAGCGGCACGTGGAGTTCAGCGACAGCAGCATCAACGACCAGACGAGGCCA
GCACCCAGACCTACGACGACAAGCAACGCCACCAGCTGAACTACGTGATGCTTCCTGATGCAGGGCAGCTGCCCCCGAGACCACCGA
CGAGCCCCTGGACCTGGAGACCCACAGAGACGTGAACTACGTGACTTCTTCAACATGATCATCGACACAGAAGAGATCACCCAGTGCCCCTGACCAAGAG
GTGCTGACCTGGAAGGGCTACCACGACTGGAGCGTGAACCAGGCCCCGGCTTCACCGGCGGACATCCTGCGCGGCCAGCCCCGG
CACCAACCTGGGCAGCGGCCACCCAGCATCGACACCTGGTGTGAAGGGCCCGGACATCCTGCGCGACATCCTGCCGCGTACCGCCAGCACCACC
CCAGATCAGCACCCTGCGCGTGAACATCGACGGCCCGCCCATCAACCAGGGCAACTTCAGCGACCATGAGCGGCAGCGGCAGCAACCT
AACCTGCAGTTCCACACCAGCATCGACGCTTCCGCACCGGCCAGCTTCACCCGTGGGCTTCAACTTCAGCAACGGCCAGCAGCATCGAGTTCGTGCCCGCCGGCCGAGTTCGTGTTCACCCGGCCGAGTACGAC
GCAGAGCGGCAGCTCGAACAGCGGCAACGAGGTGTACATCGACGAGCTGTTCAACAGCGGCTCAGAGGAGGTGACCTTCGAGGCCGAGTACGAC
ACGTGTTCAACAGCGCTCAGGTGTAGGGCCTCAGAGGCTGAACAGCGGCTCAGGGCCGGCTAGCAGCAACCAGATCGGCAACGTGACGACCTCTACC
CTGGAGAGCGTGTAGGGCCTCAGAGGCTGAGAGCCGTGAACAGCAGCAGCAACCAGATCCGGTTC AAACATTGGCAATAAGTTCTTAAGATT
GAATCCTGTTGCCGGTCTTGCGATGATTATCATATAATTTCTGTTGAATTACATTAATACGTTAAGCATGATAGAAAACAAAATATAGCGCGCAAACT
GTTATTTATGAGATGGGTTTTATGATTAGAGTCCCGCAATTATACATTAATACGGCGATAGAGAAAACAAAATATAGCGGCAAACT
AGGATAAATTATCGCGCGGTGTCATCTATGTTACTAGATCGGGAATTGGTATACCAGCTTGCATGCCTGCAGTGCAGCGTGAC
CCGGTCGTGCCCCTCTCTAGAGATAATGAGCATTGCATGTCTAAGTTATAAAAATTATAAGAATAATAATAAATATCAGTGTTTA
AAGTGCAGTTATCTATCTTATACATATATTTAAACTTACTACGAACAATTGAGTATTTGACAACAGGACTCTACAGTTTTATCTTTTAGT
GAGAATCATATAAATGAACAGTTAGACATGGTCTAAAGGACATGGTCTAAAGCTTCAACTTCACCTATTTTATTCCATATCCATTAGGGTTAGGG
GTGCATGTGTCTCCTTTTTTTGCAAATAGCTTCACCTATATTTTATTCTTTAGCCTCTAAATAAGAAAATACCCTTAAGAAATTAAAAACTAG
TTAATGGTTTTTATAATATTAGATATAAAATAGAATAAATAAAGTGACTAAAATTAAACAAATACCCTTAAGAAATTAAAAACTAAG
GAAACATTTTCTTGTTTCGAGTAGATAATGC CAGCCTGTTAAACGCCGTCGACGAGTCTAAACGGACACCAACCAGCGAACCAGC
AGCGTCGCGTCGGGCCAAGCAGACGAAGCAGACGGCACGCATCTCTGTCGCTGCTCTGGACCCCTCTGAGAGTTCCGCTCCAC
CGTTGGACTTGCTCGGCTGTCGGCATCCAGAAATTGCGTGGCGAGCGTGAGGACGTGAGCGGGCAGGGCGGCCTCTC
CTCCTCTCACGGCACGGCACCCTCTTTCCCCAACCTCGTGTTGTTCGGAGCGCACACAACACAGATCTCCTGCCCGCTAATAATAG
ACACCCCTCCACAACCCTCTTTCCCCAACCTCGTGTTGTTCGGAGCGCACACAACACAGATCTCCCCAAATCCACCCG
TCGGCAACCTCCGGCTTCAAGGTACGGGCCTGCTCGTCCTCCCCCCGCTCCTCTAGATCGGGATCGGCGGTTCCGGTCCATGG

FIG. 8B

```
TTAGGGCCCGGTAGTTCTACTTCTGTTGTTCATGTTGTTGTGTTAGATCCGTGTTGTGTTAGCCGTTCGTACACGG
ATGCGACCTGTACGTCAGACACGTTCTGATTGCTAACTTGCCAGTGTTTCTTGGGAATCCTGGGATGGCTCTAGCCGTTCC
GCAGACGGGATCGATTCATGATTTTTTGTTCGTTGCATAGGGTTGCCCTTTCCTTATTCAATATATGCCGTGCA
CTTGTTGTCGGGTCATCTTTCATGCTTTTTTTGTCTTGGTGATGATGGTCGTTCTAGATCGGAGT
AGAATTCTGTTCAAACTACCTGGTGGATTTATTAATTTGGATCTGTATGTGTGCCATACATTCATAGTTACGAATGAAGA
TGATGGATGGAAATATCGATCTAGGATAGGTATACATGTTACTGATGCGGGTTTACTGATGCCATATACAGAGATGCTTTTGTTCGT
TGGTTGTGATGATGTGGTGTGGGCGGTCGTCGTTCATTCGTTCTAGATCGGAGTAGAATACTGTTCAAACTACCTGGTGTATT
TATTAATTTGGAACTGTGGGTTTACTGATGTTAAGATGGATGGAAATATCGATCTAGGATAGGTAT
ACATGTTGATGTGGGTTTACTGATGCATATACATGCAGCATCTATTCATATGCTCTAACCTTGAGTACCTATCTAT
TATAATAAACAAGTATGTTTTATAATATTTGATCTTGATAATACTTGGATGATGATGCTCTTTTGTCGATGCTGTTTCTTTGGTGTTACTTCTGCAGGGAT
CCCTGCCTTCATACGCTATTTATTGCTTGGTACTGTTTCTTTGTCGATGCTGTTTGGTGTTACTTCTGCAGGGAT
CCCGATCATGCAAAACTCAT TAACTCAGTGCAAACTATGCCTGGGCACATCCGAAAAGCAGTTCACGAGTGCAGAATGCCGCCGGA
AATCCGTCCAGCCGATGGGCGAGCTGTGGATGGGCGCACATCTGCTCGGAGAGGCCGTTGCCAAACGCTTGGCGAACTG
GATATCGTTCACTGCGTGATGTGATTGAGAGTGATAAATCGACTCTCCATTCAGGTTCATCCAAACACAATTCTGAAATCGGTTTTGC
CCTTTCCTGTTCAAAGTATTATGCGCAGCAC AGCCACTCTGTCAAGCCGATGGGATCCCGGGTATCCGAGCGTTAACTATAAAGATCCTAACCAAGCCGGAGCTGGTTTTGC
CAAAGAAAATGCCGGAGCTAGGTATCGCCGATGAACGCGTTTCGTGCGATGAACCCTGAATTTCCGAGATTGTCTCCTACTCCAGCCGTGTCGCAGTGCACATCC
GCTGACGCGCCTTCCTTGCGATGAACGCGTTTCGTGCGATGAACCTGTTAAGCGAACGTTAAGCGCCAGCAGCCTGTTGAATATGCAGGGTGAAGA
GGCGATTGCTCACTTTTACAACAGCCTGGCGATTTTAAAATCGGCCCTGCGATCCGCTGGTGCAAACGATTCGTTAATTCTGA
AAAATCCCGCGCTGCGATTTTAAAATCGGCCCTGTCTCCCCGTATTGCTGAAGTGGTGAATGGCAAACCTGGGAAGCGATGTTCCTGTTC
ATTTTACCCGGAAGACACGCACGCTTACCTGCAAGGCGTGGCGCGATTACCGGAACTGGTGCCAATGTGAAATTCGAAGCCAAACCTCCGATAACGTGCTGCGTGCGGGTCTGAC
GCTGAAACACCGCACGCTTGATATTCCGGAACTGGTTGCCAATGTGAAATTCGAAGCCAAACCGGCTAACCAGTTGTTGACCAGCCGGT
GCCTAAATACATTGATATTCCGGAACTGGACTTCCCAGATTTGTTCTGCGTCGAAGGCGATGCAAGGTTCTCAGCAGTTACAGCTTAAA
GAAACAAGGTGCAGAAGTGCCGCCATTTGTTCTGCGTCGAAGGCGATGCAAGGTTCTCAGCAGTTACAGCTTAAA
ATTAGGCCAGAGTGCCGCCATTGTTATTGCCGCCAACGAATCACCCGGTGACTGTCAACGCCGCAGTCGATCCGTGTTCAAACATTTGGC
CCGGGTGAATCAGCGTTATTGCCGCCAACGAATCACCCGGTGACTGTCAAAGGCCACGCCGTTGACCGCTGACCTGCAGATCGTTCAAACATTTGGC
CTGTAAGAGCTTACTGAAAAATTACAT CTCTTGCTAAGCTCTTGCCGATGATTATCATATAATTCGTGAATTACGTTAAGCATGTAATAA
AATAAAGTTTCTTAAGATTGAATCCTGTTGCCGATCTTGCCGATGATTATCATATAATTCGTGAATTACGTTAAGCATGTAATAA
TTAACATGTAATGCATGACGTTATTATGAGATGGGTTTTATGAGTCCCGCAATTATACATTTAATACGGATAGAAAACA
AAATATAGCGCGCAAACTAGGATAAATTATCGCGCGCGAATGTCATCTATGTTACTAGATCTGCTAGCCCTGCAGGAAATTTACCG
GTGCCCGGGGCCCAGGCCAGCATGGCCGTATCCGGCAAATGTGTATTAAGTTGTCTAAGCGTCAATTGTTTACCACACATATACCCTC
TCCCTGGGCGTGGGCCACTGCCAAAGGTGCACCGGACAGTGCCGTGCCCAAAGCCAGAAAACCCTAGCTTCTGTT
TGTGCTGTTTTTCAATTGGTTTTTTGTTCTAACTTGTGAGTATGTCTAGATGTGAGTACACTAGCACTAGAGTACACTAGCACTAGAGTTCTAGATGTGAGTGAATATGC
```

FIG. 8C

```
ACCAACACTACACTAGAACTCTTTTGGTCAAACTACTTATCGACAACCCCTCTTTATAGTACGGCTAAAACAAATAAAGACCTA
ACTATATCACGAGTGTCCGCAACTCCTTGACACTCGGAATACGAAGACCTTCACTTTTGTTCGTCGTTAGCCGTTGCTTCAA
GTTTTATCTCCGGGATTGTTTTCACCATTGTAGTACATCTACCTGTAATGCGACTAACTTACCATTGCCTCTGCAAAACACAT
GTTAGTCACATATAAAATTACGTTGTCATTAATCACTAAAACCAGGGCCTAGATGCTTTCTAGTTAAATCCCCAACAAGT
CAAAATTCTTTCTATTTTTTGCAAGTTCCAATTGACATCTGAAAGGTTGTAAGGTACACGTTGGCTCTCATTGATAACGGGG
GAAAGATACAGTGCAAACCACCATATAATGACCCACTTCTAATCGAATGGACCTGTAACGACGAAATACCCTGTGAGAACTATGG
TTCACTCATGTTAATTCATTGAAATTGTGTAGTGAATGACATCGGTTGGGAGCCTGCTTAGAGAGTATAGATTGTCACTTTTTT
GGACCGCAACTTATTTTAAAAGATATTGCGATCGCTTGTTAGTAGCGTGTTTCAGGCCCCAATGCAGTTTCTATCGTGATCCATT
TAAGTCACTCAACATTCTCATACTTTGCATTAATTCATTCCAATCTCCAATCTCCACTACTATAAAATACTAGCTTCGATGGTCGTC
ATACGCCATGCACGAAGCATGTAGATCAATCCGCATACCAGTGGCATCTATAGATAGGCTGTGAAAACCACCCAATCCCTACT
AGTGGACATTTATCTATAGATGGACCGTGAGAAACCACACAAGTCTAACACGACAGG
```

FIG. 8D

TACAAGAATATTGAGAGCGTGAGTACATAGCAAGCATTCATTAGCAAGCATTTCAAAAGAATTAATTTCTCATAGCAATGTG
ATATCTCTCCTCACGCTCAATTCTAGTTCCTTCATGTAGAGCACATATGTCCATCCACAATCATGACAATTTTATGGTTTCTAAC
TCTATTAAACACATCTTTGCAAAGGCCCTCTAAAAGGGTGTTTTGGCCTTAGCATTCTCTCATAGTTCAACTCTTCACCTAC
AAGATTTGTGGGATCTCTAGGTTCGGGAATCTTTGTGTGGCGGCTTTGTAGACACCAATGTCTATAGCCTCTAAATATGCTTCC
ATACGAATTTCCAATATGGAAAATCGTCACCATAAAAAAACGGGAGAAGGTCCATCCCCACGGACATGTACTCTAGCGGTA
AGCTAATCTAAGAGCAACAAGGCTCTTATACCAATTGAAAGGATCACGATGCCCAAGAGGGGGTTGAATTGGGCTTTTCTAA
AATCAACACTAACTAAAATCTAAGCAAGAGCCCAACTTCACCCGACACTTCACCCGACACTAAGAGAATATACTAGAAATACAACAATG
CTAAGATAATATACTTCAAATACTTGCTAAACAATACACAATGTAAAATACTTGAATTAAGTGCGGAATGTAAAGCAAGGTTAGAAG
ACTCCTCCAATTTTCTAGAGGTATCAAAGAGTCGGCACTCTCCCCTAGTCCTCGTTGGAGCACCT GCGTAAGGGTATCGCTCTC
CCTTGGTCATCGCAAGAACCAAGTGCTCACACAGAGATGATCCTTTGCCACTCCGGGCTGGATCCTCCACGACCGCTTACA
AACTTGAGTCGGGTCACCAACAGATCTCCACGCTGATCACCGAGCTCCCAAGCCGTCTAGGTGGCTCTCGCTAGCG
CCAAGAGTAATAAGCCATAGCCTTTGACCAAGAAGCCTAATGCATGGCTTTGTGGTGCTTGCAATGCTCTACCAATGTGTAGG
TTAATGAGGTCCAAATGCGGGATTAAGATTCTCACTAGTAGGTGGATGGGTATAAATAGCCCTCACCACCAACTAGCCATTACCAGGA
AGTAAATGTGGGCAGCAAGACCATCAATATGTAGGTCCGGTGTGCCACCGGTGTCCGGTGTGCTCAACGGTCTAGTTCTGACAGCT
AGCCGTTGGACAGATGGCATGCGCGACATCCGGACAGTCCGGCATACCGGACAGTCCGGTGTGCCTCTAAATTCAACTCACGA*TTTACACCACAAT*
*ATACCCCTCTTCCCT*tagtttaaactgaaggcggaaacgacaatcgatcatgagcggagaattaaggagtcacgttatgaccccgcgatgacgcggacaagccgttttac
gtttggaactgacagaacgcaacgctgcaggaattgccgcagtcgagctgctgaatcaattgggcgccgcagcttctgcgcagcagcttcttcgcagcagcttctgagctttgagctgcagcttgcagcttgagctgtacaagctgagctgcagcttgcagacatact
gtcccacaaatgaagatgaatcgtaaaagaaaaacgtgaaataagtcgtctgacaaagttaggtcgctgcctttaatcaatacaaagttgtcctaccacgatgaaaactgtg
cagtcggtttggcttttctgacgaacaaataagattcgtgccgacaggtggggtcacccatgttgaaagtcatcttcagactccaataatgagcatgagcaatgagcttacgaaataagt
aaggtagtttggaaatgtccactcaccgtcagtctataaatactttaagggagcaaggatcaccatgacgtgtggtggcgaccgtgtggccgccgcagtgtcgttaattcgccctt
atgacggccgacaacaacaccgaggcctgacagcagacagcagacgtgatcagaagggcatcacgtggtgggcaccgtgtgggcgttgggcttccccttcggcgcg
ccctggtgagctctacaccaacatcctgaacacggcctgaacaccatcctggagctgagaagtcatgagcagttgagcagttgagcagttgagcagtgcgactacgcaag
aacaaggcactgccgagctgttcagccaggccgccaaatcacgagaggagtgggcgagcagcagcagtcctacaaagccgcaacaccagccgcgccaaacacc
cacctgtcctctgaaggaccgccaatcacgagagagtccggagcagcagcgagcagcagcgagcagcagttgggctacaagcgccgagttctacagcgccagcgagctgaacctgaccaagtcaccaccaccaccac
tgcgtgaagtggtacaacgtgcgctgtgctgaccgccgaaggagcagccgcaagcgccgcaagcgcgagatgaacctgaccgtgtggacctgtggacctgtgaccctgaccctgaccctgacctgatcgcctg
ttcccctgtacgacgtgcgctacccaaggagtgaccctgtaccccaaggagtgaccctgtgctgcacgacgtgaacaacctgctgaccgaccacatcagtgaccacatcagtggccgcgacgacccgcgacacctgaccccttcag
caacatcgagcaccgcaacctggccaagcccacctgttcgactacctgacgacactatcaccaccgccaagaggcagagctgcgcaccaccaccaccgccaccgacacactggagcgcaa
ctacgtgagcaccgccaacgctggccgcagcaacgaccatcatcaccaggcagcagagcagcagacccgtgcaagaagcaagcctgagttcaacggcgagaaggtaccg
cgccggtgctaacaccaacctggccgtgtggccgtgtggccgttggccggcgacaaggtgaccgttcagccaaggtgagttcagccgagttcagccgaggagttcagccgagttcagccgaggccgacgaccgaccagaccacgaccacacgaccagaccacgagacctacga
cagcaagcgcaacgtgggcgccgtgagctgagccgtgccgtgccccgagaccgccccgagaccagcttgaaggaaggctacagcttcaccaccacctgtgaactacgtgatgtgct

*FIG. 9A* tcctgatgcagggcaggccggcaccatcccgtgctgacctggaccacccaagagcgtgacttcttcaacatgatgacagcaagaagatcaccagctgccctgaccaagagcac
caacctgggcagccgagccaccagcgtggtgaagggccccggcttcaccggccccgacatcctgccgccgacaccagctgccgtgcacctgccgtgaacatcaccgccccct
gagccagccgctaccgcgtccgcatccgctacgccagccggcagcctgcagttccacaccagcatctgcaacttcagcgccaacttcagcgccaccatgagcagcgg
cagcaacctgcagagcgcagttgcgcacctgggcttccgcacctgggctttcaccacccccttcaacctgagcgcaacgcagcagtcaaacagcggcaacgaggtgt
acatcgaccgcatcgagttcgtgccgccgagtgacttgccccgaggtgacctgagagggctcagaaggcgtagagagctgttcaccagcagcagatcggcctgaa
gaccgactgaccgactaccacatcaggtgagattgaattcttgaattgcgtgacatcgttgccgttgcgatgattgattacatatcttgaattacatatacatgttgataccatcatatcatgttcatatgttattattcatgttcatatagttcatatgttcata
agatcgttcaaacatttggcataaagtttttaagattgaatccatcggttgccggttgccgtagtcgtctgcatttcgtgatgcatcattacatttgaatagcatatcatagattaagcatgaatctatcatgtacgcgcacgggtgtcatcattatctagatctgcta
atgagatgggtttttatgattagagtccgcaattatacatttaatacgcgatagaaaacaaaatagcgcaaactaggataaattatgcgcgcggtgcatctattatcatagatctgctaTTTACACCACAATATACCCTCTTCCCTG
gccctgcaggaaatttaccggtgcccggcgccagcatgccccgaggcccgcggcccatcgcaatgtgtttaagtgtcaatggtctaaggcatGCCAAGCACTAGCTTCGTGTTGTGTGCCAAGCGATTCGCCTTCGTGTTTGTGCTG <u>GGCCAGGCTGGGCCCACTGCTGCCAAAGGGTGCACAAGGGGTGGGCCAAAGCCAGTCCGTGCCAAGCCAGCTTCGTGAGTGTGAATATGCACCAACA</u>
<u>TTTTTCAATTGGTTTTGTCTAACTTGGTCAAATCTCTTGGTCAAATCTCTTTGACACTTTCTACAGGTACACCTAGCACTTCATCTGAGTGTGAATATGCACCAACA</u>
<u>CTACACTAGAACTCTTTGGTCAAATCTCTTGACACTACTATCGACAACCCTCTTTATAGTACGGCTAAACAAATAAAAGACCTAACTATATC</u>
<u>ACGAGTGTCCGCAACTCCTGACATTGTAGTACTACTACTCGGAATACGAAGACCTTCACTTTTGTTCGTCGTTGCTTCAAGTTTTTAT</u>
<u>CTCGGGATTGTGTTTCACCATTGTCATTAATCACTGTAGTACATCTAAAACCAACCAGGGCCTAGATGCGAATCAGGGCCTAGATGCGAACCTGTAATGCGAACCAGGGCCTAGATGCGAATCAGATCGTTAATCCCCAACAAGTCAAAATCT</u>
<u>CATATAAAATTACGTTGTCATTAATCACTGTAGTACATCTAAAACCACTTCACTTCTAGTTAAATCCCAACAAGTCAAAATCT</u>
<u>TTCTATTTTTTGCAAGTTCCAATTG ACATCTGAAAGTTGTAAGGTTGTAACGTTGGCTCTCATTGATAACGGGGAAAGATAC</u>
<u>AGTGCAAACCACCATATAATGACCACTTCTAATCGAATGGTTGGGACATGGTTGGGAGGCCTGCTTAGAGAGTATAGATGTCACTTTTTTGGACCGCA</u>
<u>GTTAATTCATTGAAATTGTGTAGTGAATTGACATGGTTAGTAGCGCTTGTTTAGTAGCTGTTTCAGGCCCCAATGCAGTTCTATCAGTTCTATCGTGATCCATTAAGTCACT</u>
<u>ACTTATTTTAAAAGATATTGCGATCGCTTGTTAGTAGCGCTTGTTAGTAGCTGTTTCAGGCCCCAATGCAGTTTCAGGCCCCAATGCATCGGGCATCCGATCAATCCGGCATCGGGCATCCAGTGGGCATCTATAGATAGGCTGTGAAAACCACCAACAGTCTAACACGACAGG</u>
<u>CAACATTCTCATCTTCATTTTGCATTAATTCATTCAATCTCCAATCTCCACTATAATCCGATCAAATACTAGCTTCGATGTCGTCATACGCCAT</u>
<u>GCACGAAGCATGTCAATCCGCATACCAGTGGGCATCCAGTGGGCATCTATAGATAGGCTGTGAAAACCACCAACAGTCTAACACGACAGG</u>
<u>TTTTATCTATAGATGGACCGTGAGAAAACCACCAACAGTCTAACACGACAGG</u>

FIG. 9B

MODIFIED EXCISABLE 5307 MAIZE TRANSGENIC LOCUS LACKING A SELECTABLE MARKER

CROSS-REFERENCE TO RELATED APPLICATIONS

This is a continuation application of International Application No. PCT/US2021/043,483, filed on Jul. 28, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, each of which are incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 21, 2022, is named "P13639US01_SequenceListing.xml" and is 120,439 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic maize event which confers tolerance to certain lepidopteran insect pests is the 5307 transgenic maize event disclosed in U.S. Pat. No. 8,466,346. The 5307 transgenic maize plants express an ecry3.1Ab protein (also referred to as an FR8a protein) which can confer resistance to western corn rootworm (*Diabrotica virgifera virgifera*), northern corn rootworm (*D. longicomis barberi*), southern corn rootworm (*D. undecimpunctata howardi*), and Mexican corn rootworm (*D. virgifera zeae*) infestations. 5307 transgenic maize plants also express a phosphomannose isomerase selectable marker protein.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells, maize plant parts including seeds, and transgenic plants comprising a transgenic locus comprising the DNA molecule of SEQ ID NO: 33, 29, 30, 32, 26, 27, 34, 36, or an allelic variant thereof are provided. Use of such cells, parts, and plants for maize plant breeding are also provided.

Methods for obtaining a bulked population of seed comprising selfing the aforementioned transgenic maize plants are provided.

Methods of obtaining hybrid maize seed comprising crossing an aforementioned transgenic maize plant to a second maize plant which is genetically distinct from the first maize plant and harvesting seed comprising the INIR17 transgenic locus from the cross are provided.

DNA molecules comprising SEQ ID NO: 16, 26, 27, 28, 29, 32, 33, 34, 36, 38, 39, or 40 are provided. Processed transgenic maize plant products and biological samples comprising the aforementioned DNA molecules are provided. Nucleic acid molecule adapted for detection of genomic DNA comprising the aforementioned DNA molecules are provided. Methods of detecting a maize plant cell comprising the INIR17 transgenic locus comprising the DNA molecule of SEQ ID NO: 33, 29, 30, 32, 26, 27, 34, 36, or an allelic variant thereof, comprising the step of detecting DNA molecule comprising SEQ ID NO: 16, 26, 27, 28, 29, 32, 33, 34, 36, 38, 39, or 40, are provided.

Method of excising an INIR17 transgenic locus from the genome of the maize plant cell comprising a transgenic locus comprising the DNA molecule of SEQ ID NO: 33, 29, 30, or an allelic variant thereof, comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the originator guide RNA recognition site (OgRRS) and the cognate guide recognitions site (CgRRS) of the transgenic locus; wherein the RdDe recognizes a OgRRS/gRNA and a CgRRS/gRNA hybridization complex; and, (b) selecting a transgenic plant cell, transgenic plant part, or transgenic plant wherein the INIR17 transgenic locus flanked by the OgRRS and the CgRRS has been excised are provided.

Methods of modifying atransgenic maize plant cell comprising: obtaining a 5307 maize event plant cell, a representative sample of which was deposited at the ATCC under accession No. PTA-9561, comprising a nucleotide sequence comprising a CMP promoter, a eCry3.1Ab coding region which is operably linked to said promoter, a first nopaline synthase (NOS) terminator element which is operably linked to said eCry3.1Ab coding region, a ZmUbiInt promoter and an operably linked phosphomannose isomerase coding region, and a second NOS terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said first NOS terminator, said ZmUbiInt promoter, and said operably linked phosphomannose isomerase coding region, are provided.

Methods of modifying a transgenic maize plant cell comprising: obtaining a 5307 maize event plant cell, a representative sample of which was deposited at the ATCC under accession No. PTA-9561, comprising a nucleotide sequence comprising a 5' junction polynucleotide, a CMP promoter, a eCry3.1Ab coding region which is operably linked to said promoter, a first nopaline synthase (NOS) terminator element which is operably linked to said eCry3.1Ab coding region, a ZmUbiInt promoter and an operably linked phosphomannose isomerase coding region, and a second NOS terminator element; and modifying said nucleotide sequence to: (i) substantially, essentially, or completely remove said first NOS terminator, said ZmUbiInt promoter, and said operably linked phosphomannose isomerase coding region; and (ii) delete and/or substitute one or more nucleotides of said 5' junction polynucleotide, optionally wherein one or more nucleotides or a polynucleotide sequence comprising a CgRRS are inserted into said 5' junction polynucleotide, are provided.

Methods of making transgenic maize plant cell comprising an INIR17 transgenic locus comprising: (a) contacting the transgenic plant genome of a maize 5307 plant cell with: (i) a first set of gene editing molecules comprising a first site-specific nuclease which introduces at least one first double stranded DNA break in a 5' junction polynucleotide of a 5307 transgenic locus; and (ii) a second set of gene editing molecules comprising a second site-specific nuclease which introduces a second double stranded DNA break between the eCry3.1Ab coding sequence and the first nopaline synthase (NOS) terminator of said 5307 transgenic locus and a third site specific nuclease which introduces a third double stranded DNA break between the phosphomannose isomerase coding region and DNA encoding the second nopaline synthase (nos) terminator element of said 5307 transgenic locus; and (b) selecting a transgenic maize plant cell, transgenic maize callus, and/or a transgenic maize plant comprising an INIR17 transgenic locus wherein one or more nucleotides of said 5' junction polynucleotide have been deleted and/or substituted, wherein the CMP promoter, the eCry3.1Ab coding region which is operably linked to the CMP promoter, and the second NOS terminator element of said 5307 transgenic locus are present, and wherein DNA of said 5307 transgenic locus comprising the first NOS terminator, the ZmUbiInt promoter and the phosphomannose isomerase coding region is absent, thereby making a transgenic maize plant cell comprising an INIR17 transgenic locus, are provided.

BRIEF DESCRIPTION OF THE DRAWINGS/FIGURES

FIG. 1 shows a schematic diagram of transgene expression cassettes and selectable markers in the 5307 transgenic locus in the deposited seed of ATCC accession No. PTA-9561 with SEQ ID NO for the corresponding segments (not to scale).

Figure 2:
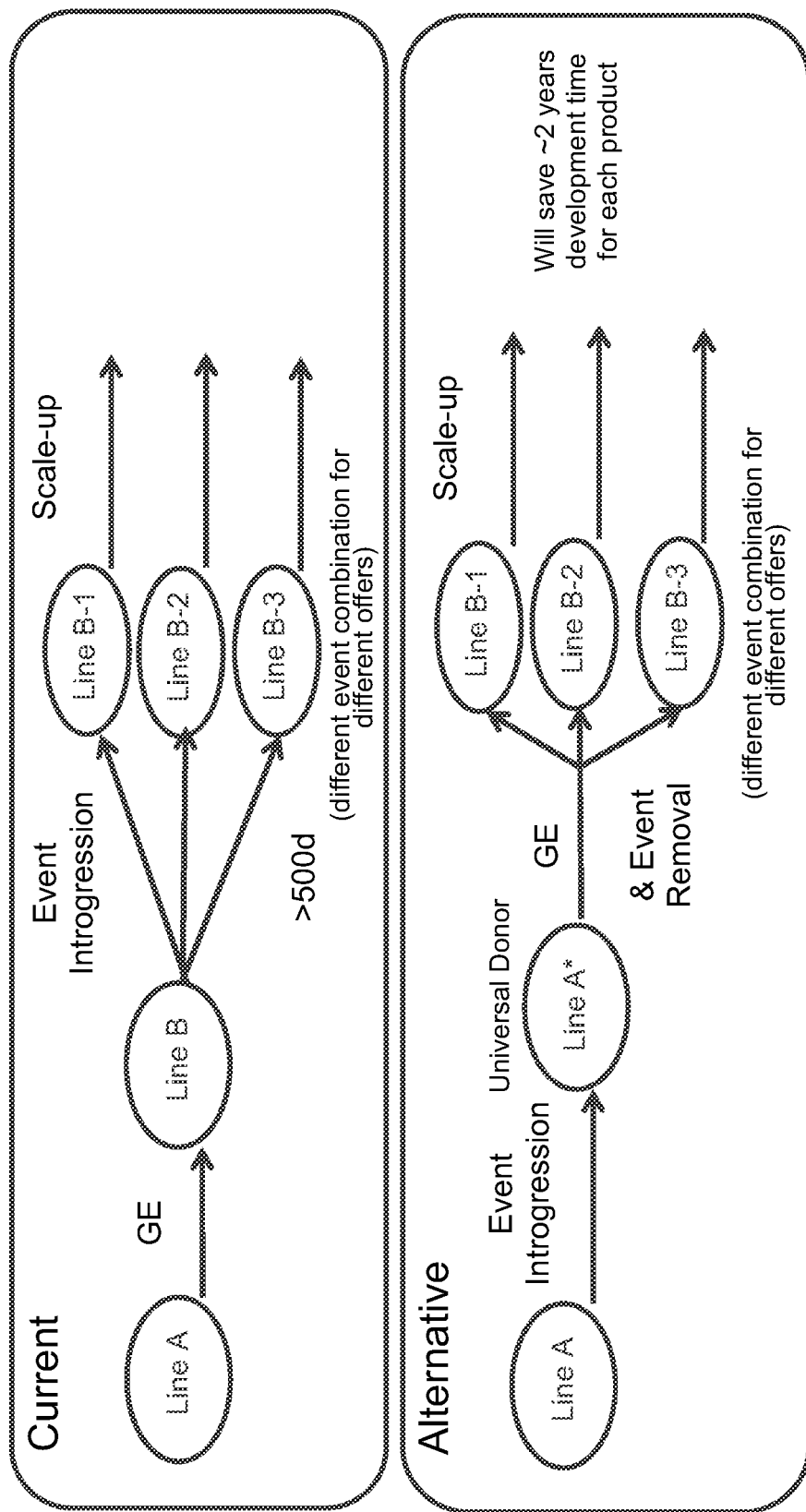

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") or portion thereof with genome editing molecules.

Figure 3A:
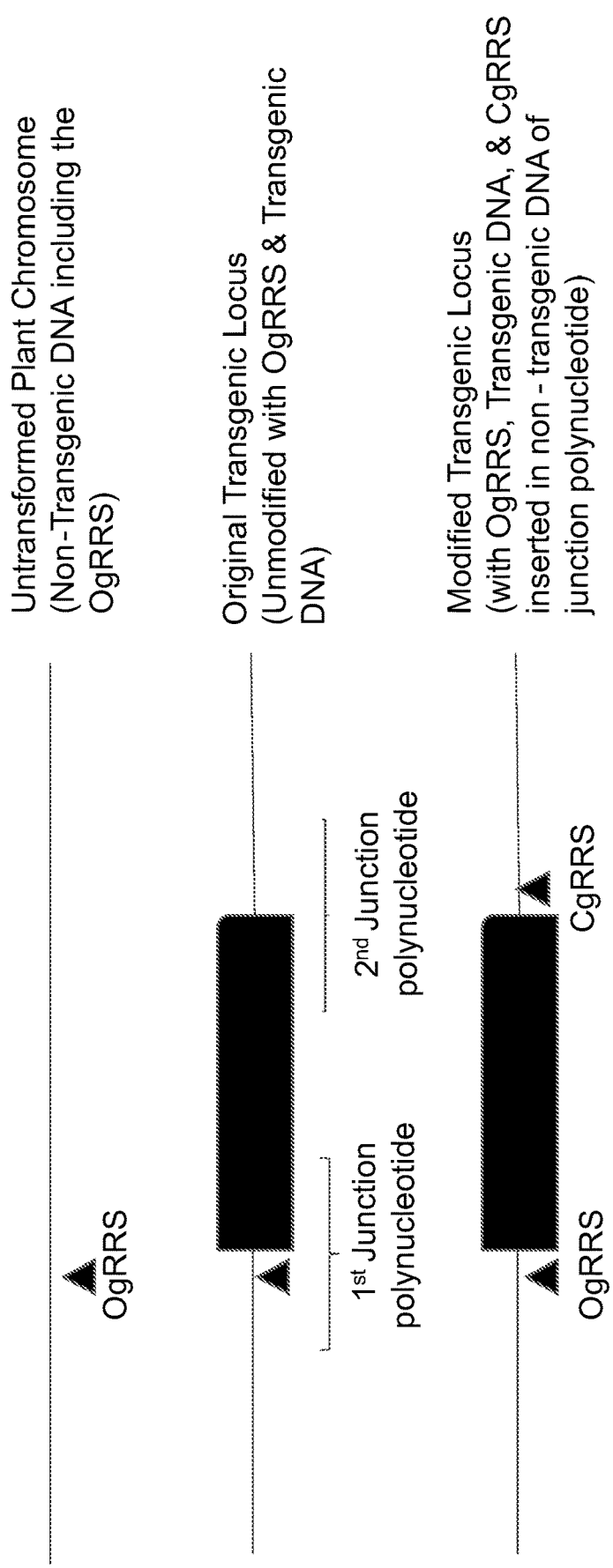
Figure 3B:
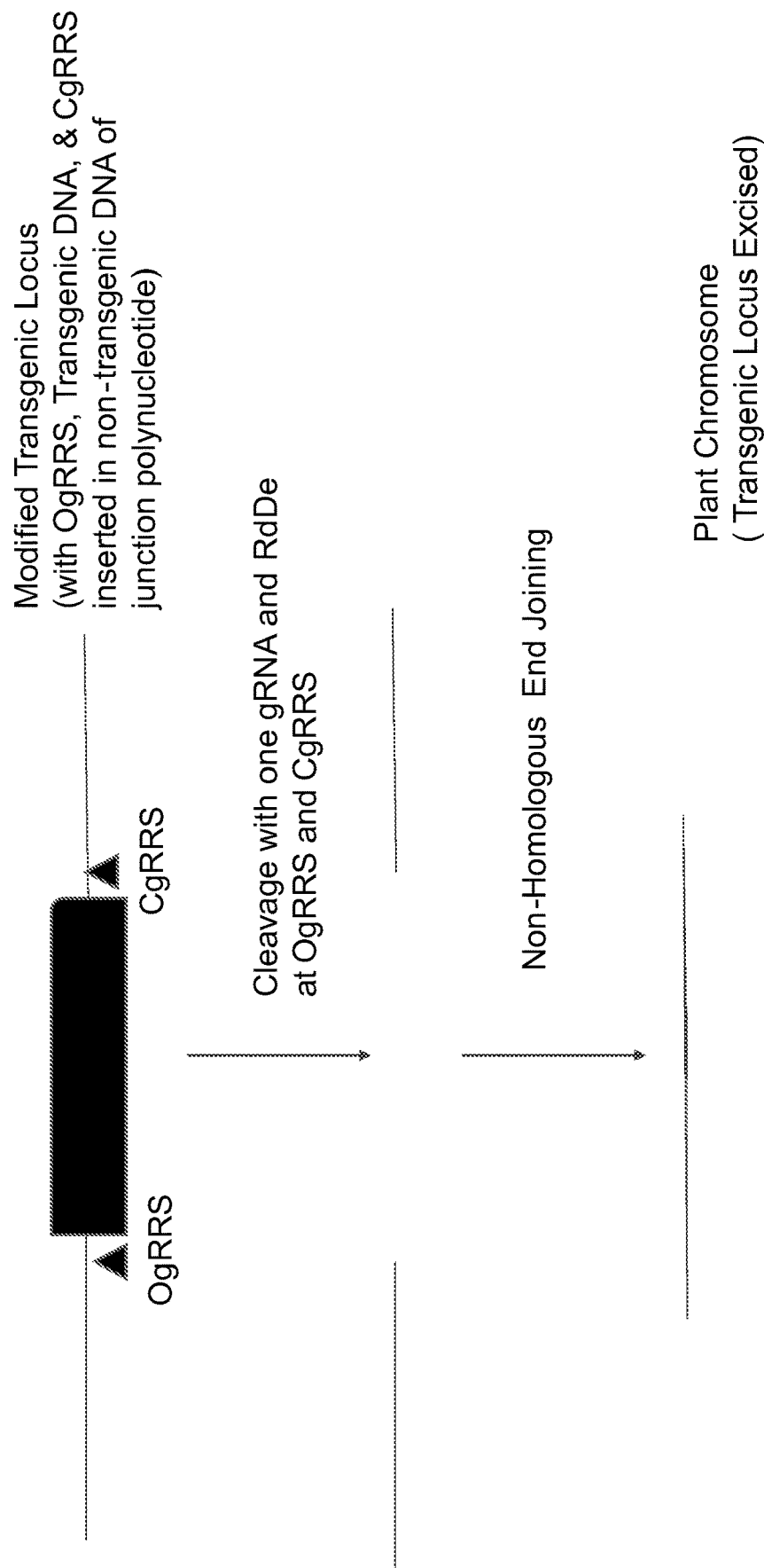
Figure 3C:
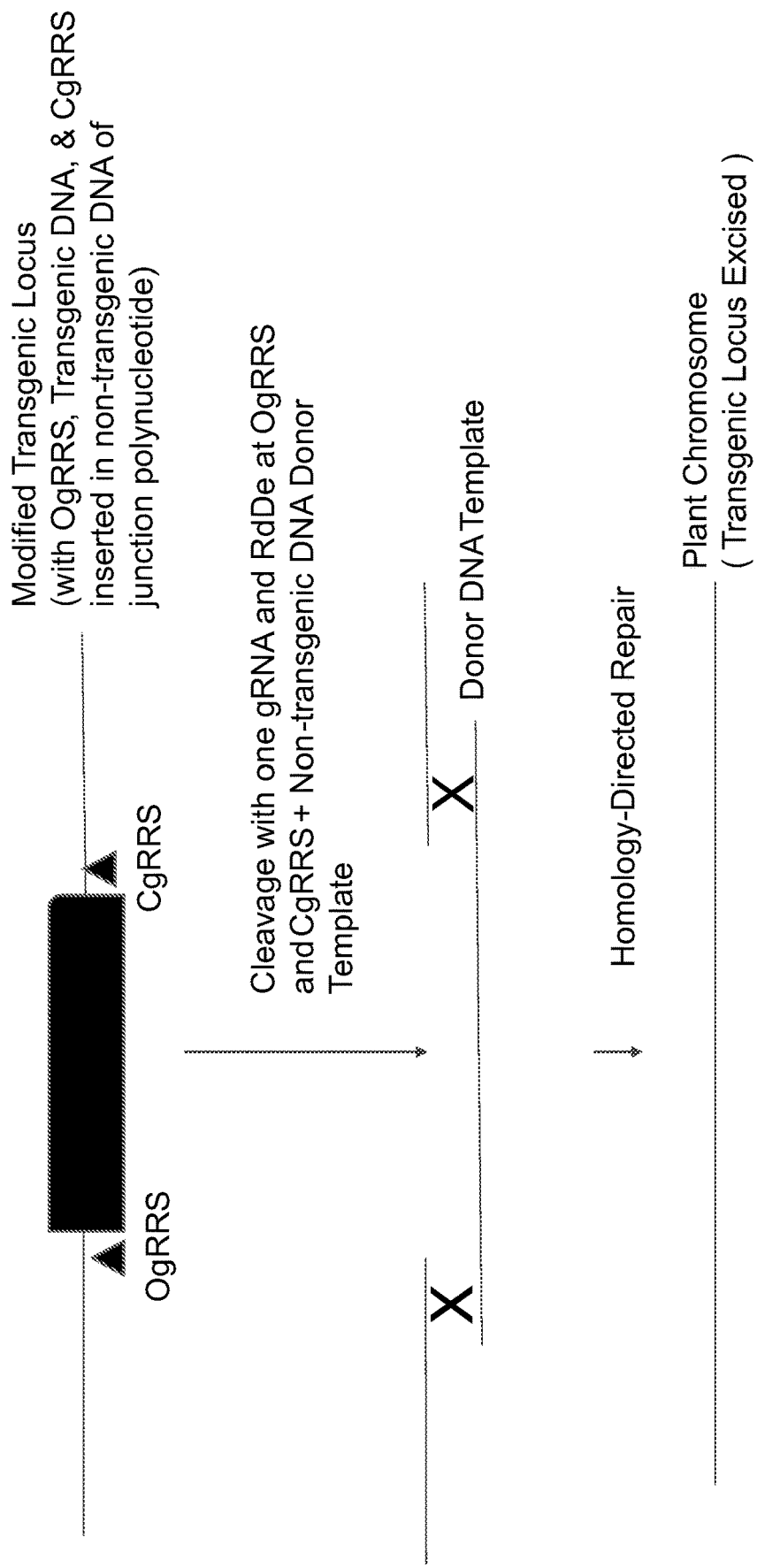

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

Figure 4:
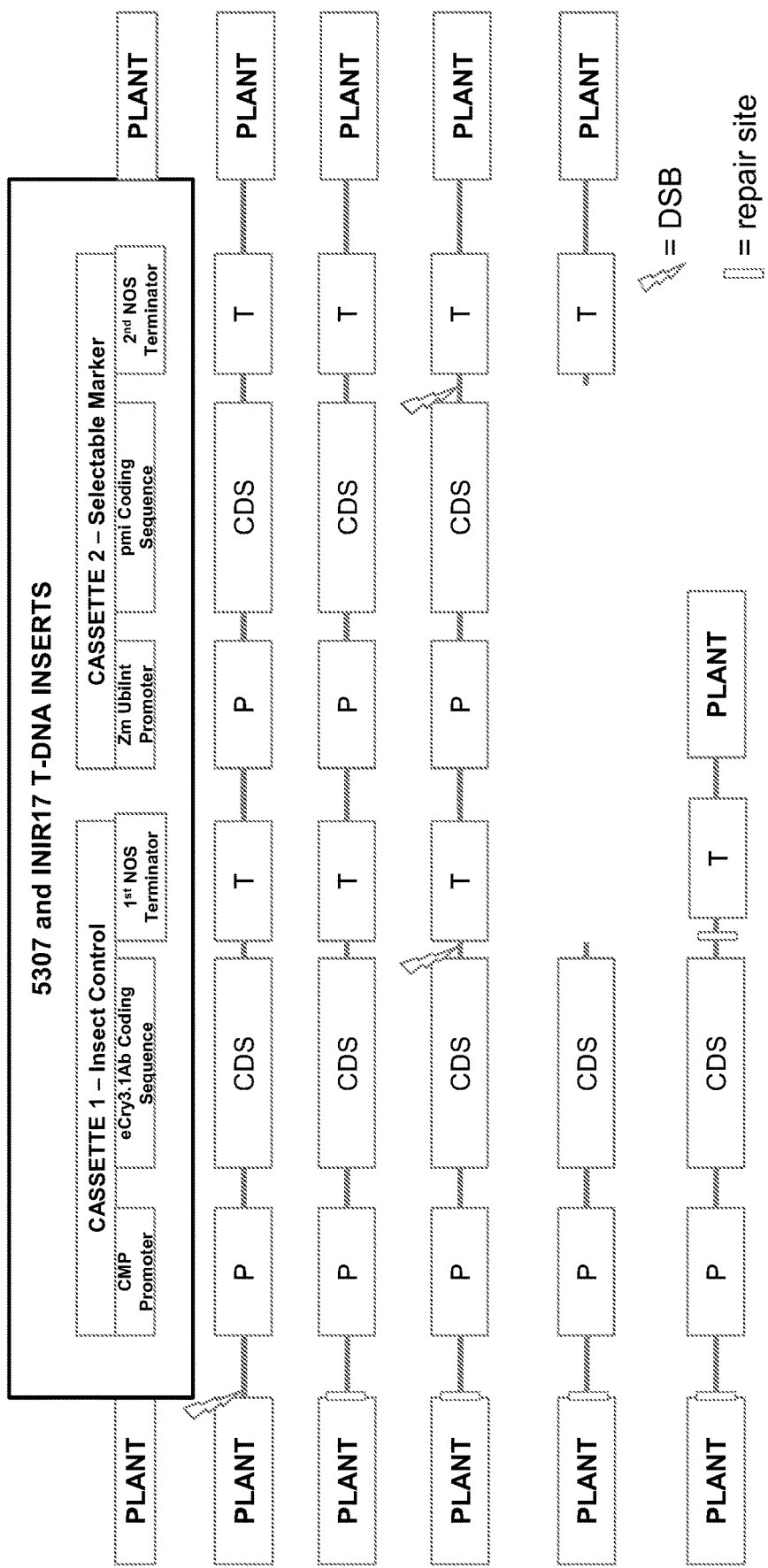

FIG. 4 shows a schematic diagram of an unmodified 5307 transgenic locus (top most), a strategy for introducing DSB at a 5' junction polynucleotide ($2^{nd}$ from top), an INIR17 transgenic locus comprising a modified 5' DNA junction polynucleotide sequence ($3^{rd}$ from top), a strategy for introducing additional DSB at sites 5' to the $1^{st}$ NOS terminator and 3' to the pmi CDS ($4^{th}$ from top), a resultant deletion of the $1^{st}$ NOS terminator, ZmUbiInt promoter, and pmi CDS ($5^{th}$ and $6^{th}$ from top), and a resultant INIR17 locus comprising a modified 5' junction sequence and the deletion of the $1^{st}$ NOS terminator, ZmUbiInt promoter, and pmi CDS (bottom most).

Figure 5:
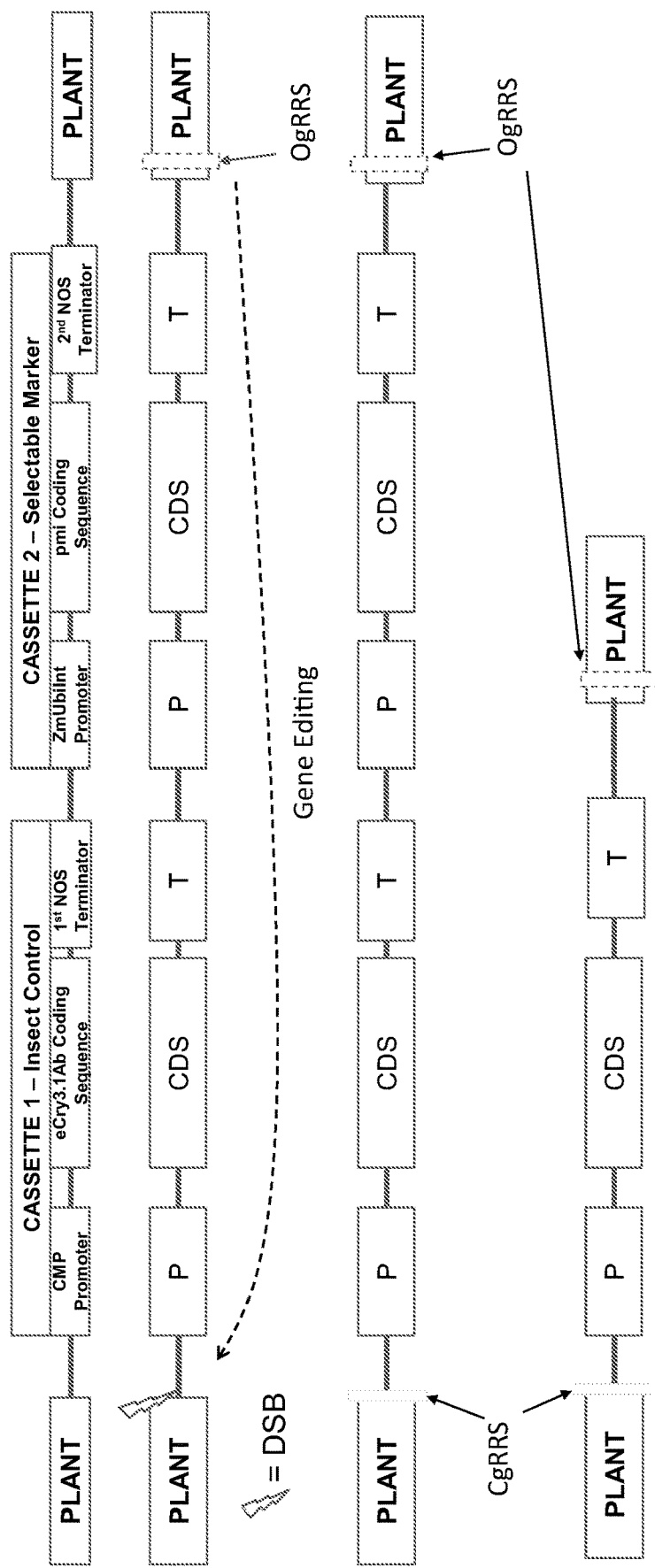

FIG. 5 shows a schematic diagram where an Originator guide RNA Recognition Site (OgRRS) present in a 5307 transgenic locus (top most and second from top) is "copied" via gene editing at the site of a DSB in a 5' junction polynucleotide (e.g., by homology directed repair with a donor polynucleotide template at the site of the DSB) to provide an INIR17 locus (third from top) with a Cognate guide RNA Recognition Site (CgRRS) which can be excised with a single gRNA that recognizes the OgRRS and the CgRRS. An INIR17 transgenic locus comprising a CgRRS and a deletion of the $1^{st}$ NOS terminator, ZmUbiInt promoter, and pmi CDS is also shown (bottom most).

Figure 6A:
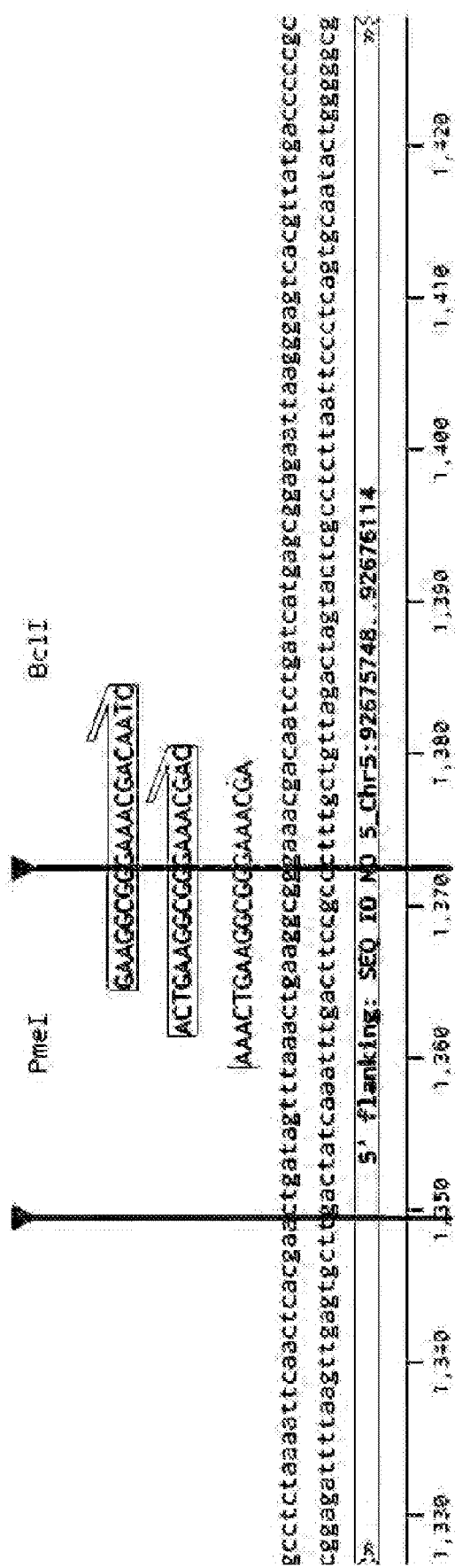
Figure 6B:
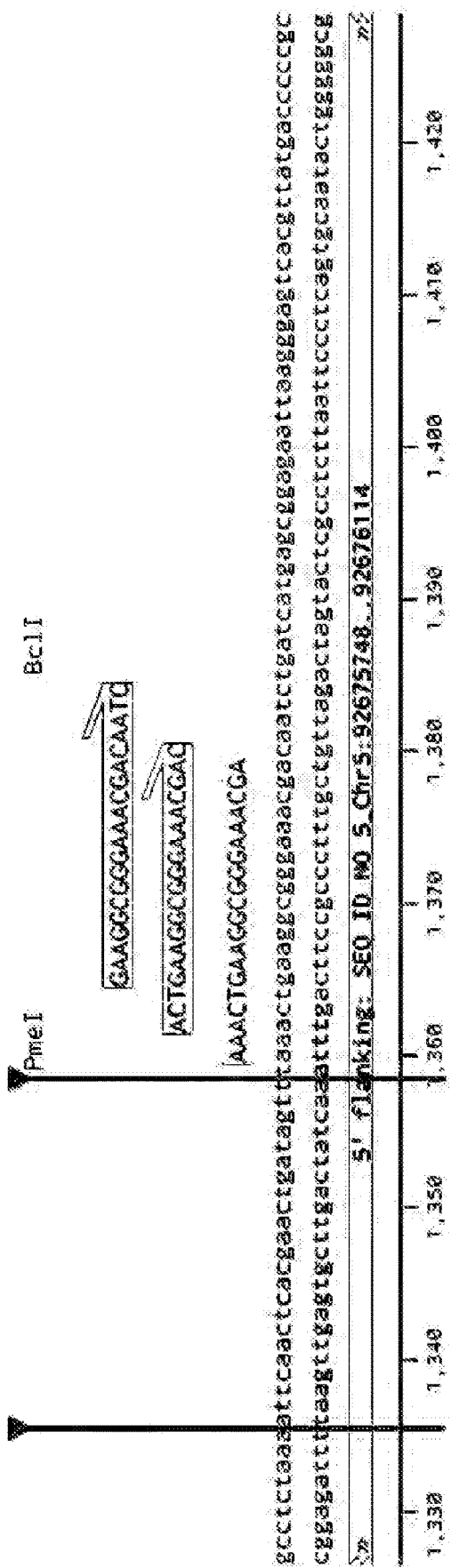

FIGS. 6A and 6B show the sequence of the DNA near the 5' junction polynucleotide of the 5307 transgenic locus and the location of Cas12a guide RNA recognition sites. In the FIGS. 6A and 6B, "SEQ ID NO:5" corresponds to the displayed section of SEQ ID NO:5 of U.S. Pat. No. 8,466, 346 and the displayed section of SEQ ID NO:7 of the instant application.

Figure 7A:
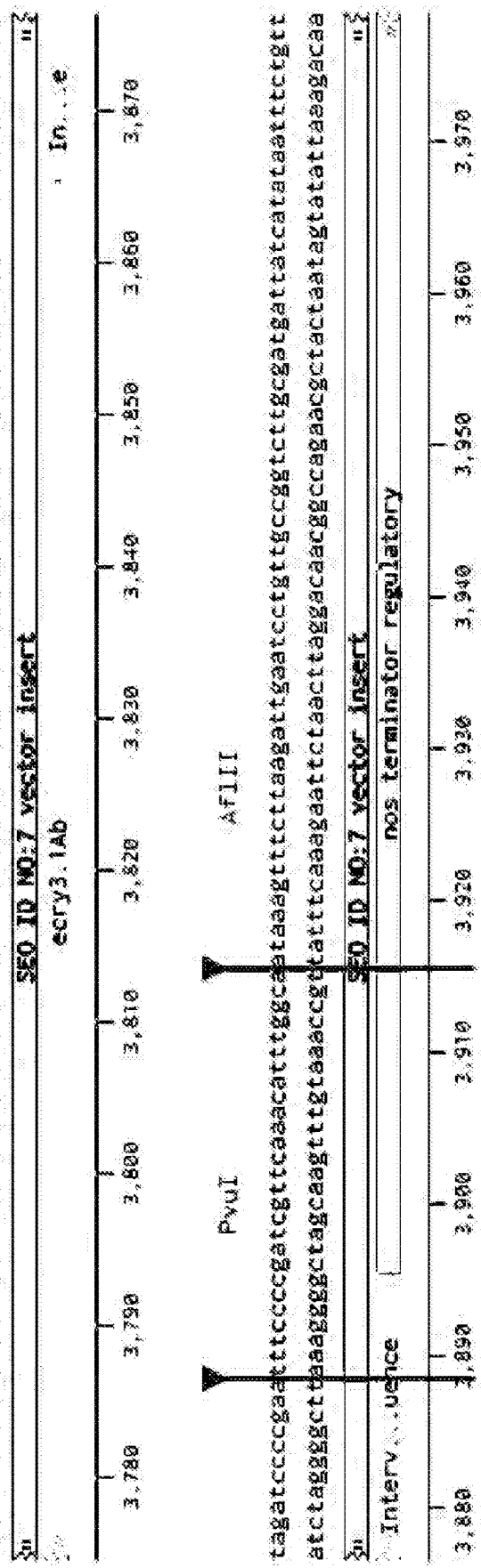
Figure 7B:
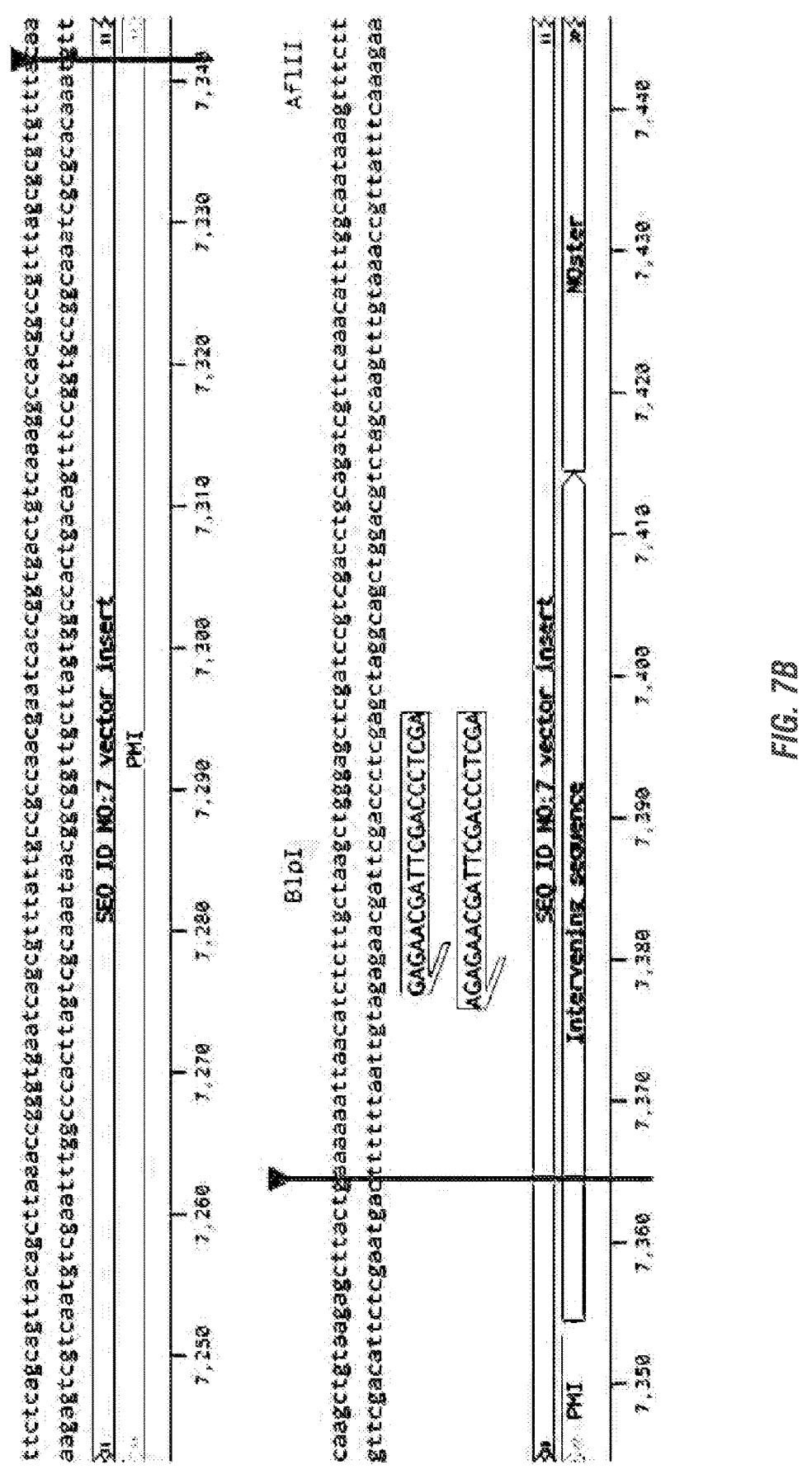

FIGS. 7A and 7B show the sequences of the 5307 transgenic locus that can be used to delete the 1st NOS terminator, ZmUbiInt promoter, and pmi coding region of the 5307 locus. Sequences located at the 5' end of the 1st NOS terminator targeted for cleavage by the guide RNA of SEQ ID NO:12 are shown in FIG. 7A and the sequences spanning the 3' end of the pmi coding region and intervening sequence targeted for cleavage by the guide RNA of SEQ ID NO:13 are shown in FIG. 7B. In the FIGS. 7A and 7B, "SEQ ID NO:7" corresponds to the displayed section of SEQ ID NO:7 of U.S. Pat. No. 8,466,346 and the displayed section of SEQ ID NO:1 of the instant application.

FIGS. 8A, 8B, 8C, and 8D show an annotated sequence of the maize 5307 transgenic locus (SEQ ID NO: 1). The 5' and 3' flanking plant genomic sequence is underlined.

FIGS. 9A and 9B show an annotated INIR17 transgenic locus sequence (SEQ ID NO: 33) which contains a CgRRS insertion at the 5'end of the CMP promoter and a deletion of DNA comprising the first NOS terminator, the ZmUbiInt promoter, and pmi coding region of the 5307 transgenic locus. The CgRRS and OgRRS sequences are in italics and uppercase. The 5' and 3' flanking plant genomic sequence is underlined and in uppercase. Transgenic insert sequence other than that corresponding to the CgRRS and OgRRS are in lowercase.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g. milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO:1) with respect to the reference polynucleotide sequence (e.g., SEQ ID NO:1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). Cas12a proteins include the protein provided herein as SEQ ID NO:37.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO:1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g. inbred or doubled haploid. Elite crop plants can include inbred lines used as is or used as pollen donors or pollen recipients in hybrid seed production (e.g. used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g. DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

As used herein, the terms "$1^{st}$ NOS terminator" or "first NOS terminator" and "$2^{nd}$ NOS terminator" or "second NOS terminator" refer respectively to the NOS terminator which is operably linked to the 3' end of the eCry3.1Ab coding region of the 5307 transgenic locus and the NOS terminator which is operably linked to the 3' end of the pmi coding region of the 5307 transgenic locus. In FIG. 1, the "$1^{st}$ NOS terminator" or "first NOS terminator" is located between the 3' end of the eCry3.1Ab coding region and the ZmUbiInt promoter. The "$2^{nd}$ NOS terminator" or "second NOS terminator" is located between the 3' end of the pmi coding region and the 3' junction in FIG. 1.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full-length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR17" is used herein to refer either individually or collectively to items that include any or all of the 5307 transgenic maize loci which have been modified as disclosed herein, transgenic maize plants and parts thereof including seed that comprise the modified 5307 transgenic loci, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

As used herein, the term "5307" is used to refer to items that include a transgenic maize locus, transgenic maize plants and parts thereof including seed set forth in U.S. Pat. No. 8,466,346, which is incorporated herein by reference in its entirety. Representative 5307 transgenic maize seed have been deposited at the American Type Culture Collection (ATCC, Manassas, VA, USA) as accession No. PTA-9561. 5307 transgenic loci include loci having the sequence of SEQ ID NO:1, the sequence of the 5307 locus in the deposited seed of accession No. PTA-9561 and any progeny thereof, as well as allelic variants and other variants of SEQ ID NO:1. Other variants of a 5307 locus can include variants in 5307 other than those disclosed herein obtained by gene editing techniques (e.g., by use of RdDe, CBE, or ABE and gRNAs, TALENs, and/or ZFN).

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS, sPAM sites, or sigRNAR sites are operably linked to junction polynucleotides when they can be recognized by a gRNA and an RdDe to provide for excision of the transgenic locus or portion thereof flanked by the junction polynucleotides. When the phrase "operably linked" is used in the context of a signature PAM site and a DNA junction polynucleotide, it refers to a PAM site which permits cleavage of at least one strand of DNA in the junction polynucleotide with an RNA dependent DNA endonuclease, RNA dependent DNA binding protein, or RNA dependent DNA nickase which recognizes the PAM site when a guide RNA complementary to sequences adjacent to the PAM site is present. When the phrase "operably linked" is used in the context of a sigRNAR site and a DNA junction polynucleotide, it refers to a sigRNAR site which permits cleavage of at least one strand of DNA in the junction polynucleotide with an RNA dependent DNA endonuclease, RNA dependent DNA binding protein, or RNA dependent DNA nickase which recognizes the sigRNAR site when a guide RNA complementary to the heterologous sequences adjacent in the sigRNAR site is present.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus or portion thereof has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "signature protospacer adjacent motif (sPAM)" or acronym "sPAM" refer to a PAM which has been introduced into a transgenic plant genome by genome editing, wherein the sPAM is absent from a transgenic plant genome comprising the original transgenic locus. A sPAM can be introduced by an insertion, deletion, and or substitution of one or more nucleotides in genomic DNA.

As used herein the phrase "signature guide RNA Recognition site" or acronym "sigRNAR site" refer to a DNA polynucleotide comprising a heterologous crRNA (CRISPR RNA) binding sequence located immediately 5' or 3' to a PAM site, wherein the sigRNAR site has been introduced into a transgenic plant genome by genome editing and wherein at least the heterologous crRNA binding sequence is absent from a transgenic plant genome comprising the original transgenic locus. In certain embodiments, the heterologous crRNA binding sequence is operably linked to a pre-existing PAM site in the transgenic plant genome. In other embodiments, the heterologous crRNA binding sequence is operably linked to a sPAM site in the transgenic plant genome.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
| --- | --- |
| 1 | 5307 transgenic locus sequence comprising 5' flanking plant genomic DNA, 5' junction, eCry3.1Ab expression cassette, pmi expression cassette, 3' junction, and 3' flanking plant genomic DNA |
| 2 | 3' flanking plant genomic DNA. |
| 3 | 3' junction (small) |
| 4 | 3' junction (large) |
| 5 | 5' junction (small) |
| 6 | 5' junction (large) |
| 7 | 5' flanking plant genomic DNA |
| 8 | DNA encoding guide targeting 5' junction |
| 9 | DNA encoding guide targeting 5' junction |
| 10 | DNA encoding guide targeting 5' junction (gRNA-3) |
| 11 | DNA encoding guide targeting 5' junction (gRNA-4) |
| 12 | DNA encoding first guide targeting 1st NOS term, ZmUbiInt promoter, and pmi removal |
| 13 | DNA encoding second guide targeting 1st NOS term, ZmUbiInt promoter, and pmi removal |
| 14 | Forward primer to PCR amplify or sequence 5'-junction |
| 15 | Reverse primer to PCR amplify or sequence 5'-junction |
| 16 | Template for HDR-mediated insertion of a CgRRS comprising SEQ ID NO: 20 at 5' end of 5307 transgenic insert |
| 17 | Sequence of an OgRRS located in 3' junction of 5307 locus |
| 18 | Forward primer to PCR amplify the HDR insert at the 5'-junction |

TABLE 1-continued

Description of sequences.

| SEQ ID NO | Description |
|---|---|
| 19 | Reverse primer to PCR amplify the HDR insert at the 5'-junction |
| 20 | Guide RNA recognition site in OgRRS of SEQ ID NO: 17 |
| 21 | HDR product produced by PCR with SEQ ID NO: 18 and 19 primers. |
| 22 | HDR product produced by PCR with SEQ ID NO: 18 and 19primers |
| 23 | This is 5307-PMI-ampseq-5' in the text. Used to confirm elimination of NOS::ZmUBI::PMI. Currently SEQ ID NO: 35. |
| 24 | This is 5307-PMI-ampseq-3' in the text. Used to confirm elimination of NOS::ZmUBI::PMI. |
| 25 | The complete, modified insert sequence after SEQ ID NO: 8 (cut/repair-Option 1 from Example 1) |
| 26 | INIR17 transgenic locus subsequence comprising the 5' flanking genomic DNA and 5' junction polynucleotide using 1st option (SEQ ID NO: 8) for single cut |
| 27 | The complete, modified insert sequence after SEQ ID NO: 9 cut/repair-Option 2 from Example 1 |
| 28 | INIR17 transgenic locus subsequence obtained using 2d option (SEQ ID NO: 9) for single cut |
| 29 | INIR17 transgenic locus comprising a 5'-CgRRS addition in 5307 transgenic locus using the SEQ ID NO: 8 gRNA recognition site |
| 30 | INIR17 transgenic locus comprising a 5'-CgRRS addition in 5307 transgenic locus using the SEQ ID NO: 8 gRNA recognition site |
| 31 | guide RNA target sequence for effecting deletions in a 5307 5' junction sequence |
| 32 | INIR17 transgenic locus comprising a NOS::ZmUbi::PMI deletion obtained with SEQ ID NOS: 12 & 13 |
| 33 | INIR17 transgenic locus comprising a 5'-CgRRS addition and a NOS::ZmUbi::PMI deletion obtained with SEQ ID NOS: 12 & 13. |
| 34 | INIR17 transgenic locus subsequence comprising a 5' junction polynucleotide edit and a NOS::ZmUbi::PMI deletion |
| 35 | Remainder of insert, see event 5307 |
| 36 | INIR17 transgenic locus sequence comprising a 5' junction polynucleotide edit and aNOS::ZmUbi::PMI deletion |
| 37 | (Cas12a Nuclease ) (>sp|U2UMQ6|CS12A_ACISB CRISPR-associated endonuclease Cas12a OS = Acidaminococcus sp. (strain BV3L6) OX = 1111120 GN = cas12a PE = 1 SV = 1) |
| 38 | Unique 5' junction polynucleotide |
| 39 | Unique 5' junction polynucleotide |
| 40 | Unique NOS/ZmUbi/PMI deletion junction |
| 41 | 5' jxn detection primer 1 |
| 42 | 5' jxn detection primer 2 |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel).

INIR17 transgenic loci comprising modifications of a 5307 transgenic loci in a maize plant genome by directed insertion, deletion, and/or substitution of DNA within or adjacent to such 5307 transgenic loci as well as methods of making and using such INIR17 transgenic loci are provided herein. In certain embodiments, the INIR17 transgenic loci comprise the CMP promoter, the eCry3.1Ab coding region which is operably linked to said promoter, and the $2^{nd}$ nopaline synthase terminator element of a 5307 transgenic locus which is operably linked to the eCry3.1Ab coding region, wherein DNA of said 5307 transgenic locus comprising the $1^{st}$ NOS terminator element, the ZmUbiInt promoter and the operably linked phosphomannose isomerase (pmi) coding region is absent. Such INIR17 transgenic loci can thus comprise an eCry3.1Ab expression cassette and a single NOS terminator element (i.e., the $2^{nd}$ NOS terminator) while lacking non-essential DNA elements (e.g., the $1^{st}$ NOS terminator, the ZmUbiInt promoter, and the pmi selectable marker gene which is operably linked thereto) such as in the non-limiting examples illustrated in FIGS. 4 and 5. In certain embodiments, the INIR17 transgenic loci can comprise a cognate guide RNA recognition site (CgRRS) or can comprise both a CgRRS and lack non-essential DNA elements (e.g., the $1^{st}$ NOS terminator, the ZmUbiInt promoter, and the pmi selectable marker gene which is operably linked thereto) such as in the non-limiting example illustrated in FIG. 5.

In certain embodiments, INIR17 transgenic loci provided herein can thus comprise deletions of selectable marker genes and/or repetitive sequences. In its unmodified form (in certain embodiments, the "unmodified form" is the "original form," "original transgenic locus," etc.) a 5307 transgenic locus comprises a phosphomannose isomerase (pmi)-encoding selectable marker gene which confers the ability to grow on mannose as a carbon source. In embodiments provided herein, the selectable marker gene which is deleted comprises, consists essentially of, or consists of a DNA molecule encoding: (i) the phosphomannose isomerase (pmi) of a 5307 transgenic locus and the ZmUbi promoter that is operably linked thereto; or (ii) the $1^{st}$ NOS terminator, the ZmUbi promoter, and the phosphomannose isomerase (pmi) selectable marker gene of a 5307 transgenic locus. In certain embodiments, DNA elements comprising the $1^{st}$ NOS terminator, the ZmUbi promoter, and the phosphomannose isomerase (pmi) selectable marker gene of a 5307 transgenic locus of SEQ ID NO:1 can be absent from an INIR17 locus. In certain embodiments, the INIR17 locus comprising a deletion of DNA encoding the $1^{st}$ NOS terminator, the ZmUbi promoter, and the phosphomannose isomerase (pmi) selectable marker gene of a 5307 transgenic locus is set forth in SEQ ID NO:32, 33, or 36. In certain embodiments, the DNA comprising the $1^{st}$ NOS terminator, the ZmUbi promoter, and the phosphomannose isomerase (pmi) selectable marker gene to be deleted is flanked by operably linked protospacer adjacent motif (PAM) sites in a 5307 transgenic locus which are recognized by an RNA dependent DNA endonuclease (RdDe); for example, a class 2 type II or class 2 type V RdDe. In certain embodiments, the deleted selectable marker gene is replaced in an INIR17 transgenic locus by an introduced DNA sequence as discussed in further detail elsewhere herein. For example, in certain embodiments, the introduced DNA sequence comprises a trait expression cassette such as a trait expression cassette of another transgenic locus. In addition to the deletion of a selectable marker gene, in certain embodiments at least one copy of a repetitive sequence (i.e. the $1^{st}$ NOS terminator) has also been deleted with genome editing molecules from a 5307 transgenic locus. In certain embodiments, the repetitive sequence comprises, consists essentially of, or consists of the two NOS terminators which are each operably linked to either the eCry3.1Ab gene and to the pmi selectable marker gene within the 5307 transgenic locus (e.g., as depicted in FIGS. 1, 4, and 5). In certain embodiments, at least one of the repetitive sequences which comprises, consists essentially of, or consists of the $1^{st}$ NOS terminator of a 5307 transgenic locus is absent or essentially deleted from the INIR17 transgenic locus (e.g., wherein no more than about 1 or 2 to about 8 to 10 nucleotides of the $1^{st}$ NOS terminator are deleted). In certain embodiments, any of the aforementioned INIR17 transgenic loci can optionally further comprise: (i) an OgRRS and a CgRRS which are operably linked to a $1^{st}$ and a $2^{nd}$ junction sequence of the INIR17 transgenic locus; (ii) one or more signature protospacer adjacent motif (sPAM) sites which are operably linked to a $1^{st}$ and a $2^{nd}$ junction sequence of the INIR17 transgenic locus; or (iii) signature guide RNA Recognition site (sigRNAR) sites which are operably linked to a $1^{st}$ and a $2^{nd}$ junction sequence of the INIR17 transgenic locus. Also provided herein are plants comprising any of the aforementioned INIR17 transgenic loci.

In certain embodiments, an INIR17 transgenic locus can further comprise modifications of a 5' or 3' junction polynucleotide of a 5307 transgenic locus (e.g., as set forth in SEQ ID NO:1 and in FIG. 1). Such modifications of junction polynucleotides include deletions of DNA segments comprising non-essential transgenic DNA in a junction polynucleotide. In certain embodiments, such deletions of non-essential DNA of a 5' junction polynucleotide of an INIR17 transgenic locus include those set forth in SEQ ID NO:25, 26, 27, 28, 34, and 36. In certain embodiments, such deletions of non-essential DNA of a 5' junction polynucleotide of an INIR17 transgenic locus include those wherein nucleotides corresponding to nucleotides 1,350 to 1,356 of SEQ ID NO:1 are deleted and/or replaced in whole or in part by a distinct polynucleotide sequence.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR17 transgenic loci provided here are characterized by polynucleotide sequences that can facilitate as necessary the removal of the INIR17 transgenic loci from the genome. Useful applications of such INIR17 transgenic loci and related methods of making include targeted excision of a INIR17 transgenic locus or portion thereof in certain breeding lines to facilitate recovery of germplasm with subsets of transgenic traits tailored for specific geographic locations and/or grower preferences. Other useful applications of such INIR17 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR17 transgenic loci or portions thereof which can be selectively excised with one or more gRNA molecules and RdDe (RNA dependent DNA endonucleases) which form gRNA/target DNA complexes. Such selectively excisable INIR17 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA, transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. In certain embodiments such as those illustrated in the non-limiting example of FIG. 3, the OgRRS is located in non-transgenic DNA of a 5' junction polynucleotide and the CgRRS is introduced into non-transgenic DNA of a 3' junction polynucleotide. In other embodiments, the OgRRS can be located in non-transgenic DNA of a 3' junction polynucleotide and the CgRRS is introduced into non-transgenic DNA, transgenic DNA, or a combination thereof in a 5' junction polynucleotide. Examples of OgRRS polynucleotide sequences in or near a 3' junction polynucleotide in a 5307 transgenic locus include SEQ ID NO:20. OgRRS polynucleotide sequences located in a first junction polynucleotide can be introduced into the second junction polynucleotide using donor DNA templates as illustrated in FIG. 3A and as elsewhere described herein. A donor DNA template for introducing the SEQ ID NO:17 OgRRS into the 5' junction polynucleotide of a 5307 locus includes the donor DNA template of SEQ ID NO:16. Integration of the SEQ ID NO:16 donor DNA template into the 5' junction polynucleotide of a 5307 locus can provide an INIR17 locus comprising the CgRRS sequence set forth in SEQ ID NO:17. Integration of the SEQ ID NO:16 donor DNA template into the 5' junction polynucleotide of a 5307 locus can provide an INIR17 locus set forth in SEQ ID NO:29 or 30, wherein the entire phosphomannose isomerase (pmi)-encoding selectable marker gene is retained. An INIR17 transgenic locus of comprising a CgRRS sequence in its 5' junction polynucleotide and a deletion of the 1$^{st}$ NOS terminator, the ZmUbiInt promoter, and the phosphomannose isomerase coding region is illustrated in FIGS. 9A and 9B. Integration of the SEQ ID NO:16 donor DNA template into the 5' junction polynucleotide of an INIR17 transgenic locus can provide an INIR17 locus set forth in SEQ ID NO:33, wherein the 1$^{st}$ NOS terminator, the ZmUbiInt promoter, and the phosphomannose coding region are absent.

Such selectively excisable INIR17 transgenic loci can also comprise signature protospacer adjacent motif (sPAM) sites and/or signature guide RNA recognition (sigRNAR) sites, wherein the sPAM and/or sigRNAR sites are operably linked to both DNA junction polynucleotides of the INIR17 transgenic locus. Such sigRNAR sites can be recognized by RdDe and suitable guide RNAs containing crRNA complementary to heterologous DNA sequences adjacent to a PAM or sPAM site to provide for cleavage within or near the two junction polynucleotides. Such heterologous sequences which introduced at the sigRNAR site are at least 17 or 18 nucleotides in length and are complementary to the crRNA of a guide RNA. In certain embodiments, the heterologous polynucleotide of the sigRNAR is about 17 or 18 to about 24 nucleotides in length. Non-limiting features of the heterologous DNA sequences in the sigRNAR include: (i) absence of significant homology or sequence identity (e.g., less than 50% sequence identity across the entire length of the heterologous sequence) to any other endogenous or transgenic sequences present in the transgenic plant genome or in other transgenic genomes of the maize plant being edited (ii) absence of significant homology or sequence identity (e.g., less than 50% sequence identity across the entire length of the heterologous sequence) of a heterologous sequence of a first sigRNAR site to a heterologous sequence of a second or third sigRNAR site; and/or (ii) optimization of the heterologous sequence for recognition by the RdDe and guide RNA when used in conjunction with a particular PAM sequence. In certain embodiments, the sigRNAR sites which are created are recognized by the same class of RdDe (e.g., Class 2 type II or Class 2 type V) or by the same RdDe (e.g., both sPAMs or PAMs of the sigRNAR recognized by the same RdDe (e.g., Cas9 or Cas 12 RdDe). In certain embodiments, the same sigRNAR sites can be introduced in both 5' and 3' junction polynucleotides to permit excision of the INIR17 transgenic locus by a single guide RNA and a single RdDe. In certain embodiments, different sets of distinct sigRNAR sites can be introduced in the 5' and 3' junction polynucleotides of different transgenic loci to permit selective excision of any single transgenic locus by a single guide RNA and a single RdDe directed to the distinct sigRNAR sites that flank the transgenic locus. A sigRNAR site can be created in the plant genome by inserting the heterologous sequence adjacent to a pre-existing PAM sequence using genome editing molecules. A sigRNAR site can be created in the plant genome by inserting the heterologous sequence adjacent to a preexisting PAM sequence using genome editing molecules. A sigRNAR site also can be created in the plant genome by inserting both the heterologous sequence and an associated PAM or sPAM site in a junction polynucleotide. Such insertions can be made in non-transgenic plant genomic DNA of the junction polynucleotide, in the inserted transgenic DNA of the junction polynucleotide, or can span the junction comprising both non-transgenic plant genomic DNA and inserted transgenic DNA of the junction polynucleotide. Such nucleotide insertions can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion. Guide RNAs can be directed to the junction polynucleotides by using a pre-existing PAM site located within or adjacent to a junction polynucleotide of the transgenic locus.

Also provided herein are allelic variants of any of the INIR17 transgenic loci or DNA molecules provided herein. In certain embodiments, such allelic variants of INIR17 transgenic loci include sequences having at least 85%, 90%, 95%, 98%, or 99% sequence identity across the entire length or at least 20, 40, 100, 500, 1,000, 2,000, 4,000, 8,000, or 8,865 nucleotides of SEQ ID NO: 26, 27, 29, 30, 32, 33, 34, or 36. In certain embodiments, such allelic variants of INIR17 DNA molecules include sequences having at least 85%, 90%, 95%, 98%, or 99% sequence identity across the entire length of SEQ ID NO: 16, 26, 27, 28, 29, 32, 33, 34, 36, 38, 39, or 40.

Also provided are unique transgenic locus excision sites created by excision of INIR17 transgenic loci or selectively excisable INIR17 transgenic loci, DNA molecules comprising the INIR17 transgenic loci or unique fragments thereof (i.e., fragments of an INIR17 locus which are not found in a 5307 transgenic locus), INIR17 plants comprising the same, biological samples containing the DNA, nucleic acid markers adapted for detecting the DNA molecules, and related methods of identifying maize plants comprising unique INIR17 transgenic locus excision sites and unique fragments of a INIR17 transgenic locus. DNA molecules comprising unique fragments of an INIR17 transgenic locus are diagnostic for the presence of an INIR17 transgenic locus or fragments thereof in a maize plant, maize cell, maize seed, products obtained therefrom (e.g., seed meal or stover), and biological samples. DNA molecules comprising unique fragments of an INIR17 transgenic locus include DNA molecules comprising modified 5' junction polynucleotides. Unique 5' junction polynucleotides of an INIR17 transgenic locus include DNA molecules comprising SEQ ID NO:38 and 39. DNA molecules comprising unique fragments of an INIR17 transgenic locus also include DNA molecules comprising modified junction polynucleotides containing CgRRS sequences comprising insertions of OgRRS sequences (e.g., a CgRRS element comprising SEQ ID NO:17) that include SEQ ID NO:16. DNA molecules comprising unique fragments of an INIR17 transgenic locus also include DNA molecules comprising deletion junctions corresponding to residues spanning the deletion of the phosphomannose isomerase coding region and operably linked ZmUbiInt promoter in the INIR17 transgenic locus. Such deletion junctions thus comprise one or more nucleotides located between the 3' end of the eCry3.1Ab coding region and the 5' end of the 1st NOS terminator which are directly joined to (i.e., are contiguous with) nucleotides located between or at the 3' terminus of the pmi coding region and the 5' end of the 2nd NOS terminator in a 5307 locus as illustrated in FIG. 4. Examples of unique INIR17 DNA fragment comprising a such deletion include of SEQ ID NO:40. In certain embodiments, any of the aforementioned unique fragments of an INIR17 transgenic locus comprise DNA molecules of at least about 18, 20, or 24 nucleotides to about 30, 50, 100, or 200 nucleotides in length. Also provided herein are nucleic acid hybridization probes and primers (e.g., for SNP analysis) adapted for detection of INIR17 transgenic loci which can comprise all or part of any of the aforementioned DNA molecules and optionally a detectable label. Methods and reagents (e.g., nucleic acid markers including nucleic acid probes and/or primers) for detecting plants, edited plant genomes, and biological samples containing DNA molecules comprising the transgenic loci excision sites and/or non-essential DNA deletions are also provided herein. Detection of the DNA molecules can be achieved by any combination of nucleic acid amplification (e.g., PCR amplification), hybridization, sequencing, and/or mass-spectrometry based techniques. Methods set forth for detecting junction nucleic acids in unmodified transgenic loci set forth in US 20190136331 and U.S. Pat. No. 9,738,904, both incorporated herein by reference in their entireties, can be adapted for use in detection of the nucleic acids provided herein. In certain embodiments, such detection is achieved by amplification and/or hybridization-based detection methods using a method (e.g., selective amplification primers) and/or probe (e.g., capable of selective hybridization or generation of a specific primer extension product) which specifically recognizes the target DNA molecule (e.g., transgenic locus excision site) but does not recognize DNA from an unmodified transgenic locus. In certain embodiments, the hybridization probes can comprise detectable labels (e.g., fluorescent, radioactive, epitope, and chemiluminescent labels). In certain embodiments, a single nucleotide polymorphism detection assay can be adapted for detection of the target DNA molecule (e.g., transgenic locus excision site). Detection of any of the aforementioned unique DNA fragments comprising SEQ ID NO:16, 38, 39, or 40, and/or in a biological sample indicates that the sample contains material from a INIR17 plant or seed.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize 5307 transgenic locus. The maize 5307 transgenic locus and its transgenic junction sequences are also depicted in FIG. 1. Maize plants comprising the 5307 transgenic locus and seed thereof have been cultivated, been placed in commerce, and have been described in a variety of publications by various governmental bodies. Databases which have compiled descriptions of the 5307 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of an original 5307 transgenic locus which can be improved by the methods provided herein are set forth or otherwise provided in SEQ ID NO:1, U.S. Pat. No. 8,466,346, the sequence of the 5307 locus in the deposited seed of ATCC accession No. PTA-9561, and elsewhere in this disclosure. In certain embodiments provided herein, the 5307 transgenic locus set forth in SEQ ID NO:1 or present in the deposited seed of ATCC accession No. PTA-9561 is referred to as an original 5307 transgenic locus. The 5307 transgenic locus set forth in SEQ ID NO:1 encodes the eCry3.1Ab protein. Allelic or other variants of the sequence set forth in SEQ ID NO:1, the patent references set forth therein and incorporated herein by reference in their entireties, and elsewhere in this disclosure which may be present in certain variant 5307 transgenic plant loci (e.g., progeny of deposited seed of accession No. PTA-9561 which contain allelic variants of SEQ ID NO:1 or progeny originating from transgenic plant cells comprising the original 5307 transgenic set forth in U.S. Pat. No. 8,466,346 which contain allelic variants of SEQ ID NO:1) can also be improved by identifying sequences in the variants that correspond to the sequences of SEQ ID NO:1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, or 8,865 nucleotides of SEQ ID NO:1. Also provided are plants, plant parts including seeds, genomic DNA, and/or DNA obtained from INIR17 plants which comprise one or more modifications (e.g., via insertion of a CgRRS in a junction polynucleotide sequence) which provide for selective excision of the INIR17 transgenic locus or a portion thereof (e.g., the eCry3.1Ab coding region and operably linked promoter). Such INIR17 transgenic loci can be treated with gene editing molecules (e.g., RdDe and gRNA(s)) to obtain plants wherein a segment comprising, consisting essentially of, or consisting of the INIR17 transgenic locus or a portion thereof (e.g., the eCry3.1Ab coding region and operably linked promoter) is deleted. In certain embodiments, the 5307 transgenic loci set forth in SEQ ID NO:1 and allelic variants thereof are further modified by deletion of a segment of DNA comprising, consisting essentially of, or consisting of a selectable marker gene or portions thereof (e.g., the $1^{st}$ NOS terminator, pmi coding region and operably linked ZmUbi promoter) and/or non-essential DNA (e.g., T-DNA border sequences or anything other than the CMP::Cry3.1Ab::NOS expression cassette) to obtain INIR17 transgenic loci. In certain embodiments, the INIR17 transgenic locus comprises a deletion of the $1^{st}$ NOS terminator, phosphomannose isomerase (PMI) coding region, and ZmUbi promoter which are in a 5307 transgenic locus. Also provided herein are methods of detecting plants, genomic DNA, and/or DNA obtained from plants comprising a INIR17 transgenic locus which contains one or more of a CgRRS, deletions of selectable marker genes, deletions of non-essential DNA, and/or a transgenic locus excision site. A first junction polynucleotide of a 5307 transgenic locus can comprise either one of the junction polynucleotides found at the 5' end or the 3' end of any one of the sequences set forth in SEQ ID NO:1, allelic variants thereof, or other variants thereof. An OgRRS can be found within non-transgenic DNA, transgenic DNA, or a combination thereof in either one of the junction polynucleotides of any one of SEQ ID NO:1, allelic variants thereof, or other variants thereof. A second junction polynucleotide of a transgenic locus can comprise either one of the junction polynucleotides found at the 5' or 3' end of any one of the sequences set forth in SEQ ID NO:1, allelic variants thereof, or other variants thereof. A CgRRS can be introduced within transgenic, non-transgenic DNA, or a combination thereof of either one of the junction polynucleotides of any one of SEQ ID NO:1, allelic variants thereof, or other variants thereof to obtain an INIR17 transgenic locus. In certain embodiments, the OgRRS is found in non-transgenic DNA or transgenic DNA of the 5' junction polynucleotide of a transgenic locus of any one of SEQ ID NO:1, allelic variants thereof, or other variants thereof and the corresponding CgRRS is introduced into the transgenic DNA, non-transgenic DNA, or a combination thereof in the 3' junction polynucleotide of the 5307 transgenic locus of SEQ ID NO:1, allelic variants thereof, or other variants thereof to obtain an INIR17 transgenic locus. In other embodiments, the OgRRS is found in non-transgenic DNA or transgenic DNA of the 3' junction polynucleotide of the 5307 transgenic locus of any one of SEQ ID NO:1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO:1, allelic variants thereof, or other variants thereof to obtain an INIR17 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR17 transgenic locus, in transgenic DNA of a DNA junction polynucleotide of an INIR17 transgenic locus or can span the junction of the transgenic and non-transgenic DNA of a DNA junction polynucleotide of an INIR17 transgenic locus. An OgRRS can likewise be located in non-transgenic plant genomic DNA of a DNA junction polynucleotide of an INIR17 transgenic locus, in transgenic DNA of a DNA junction polynucleotide of an INIR17 transgenic locus or can span the junction of the transgenic and non-transgenic DNA of a DNA junction polynucleotide of an INIR17 transgenic locus.

Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR17 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g. Line A+ in FIG. 2) comprising two or more of the modified transgenic loci. This elite germplasm containing the modified transgenic loci (e.g. "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR17 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as lepidopteran insects or coleopteran insects other than *Diabrotica* spp.), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize,) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g.; plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR17 transgenic locus comprising an OgRRS in non-transgenic DNA of a $1^{st}$ junction polynucleotide sequence and a CgRRS in a $2^{nd}$ junction polynucleotide sequence is deleted with a gRNA and RdDe that recognize the OgRRS and the CgRRS to produce an INIR17 transgenic locus excision site. In certain embodiments, a segment comprising an INIR17 transgenic locus comprising a sPAM and/or a sigRNAR site in a $1^{st}$ junction polynucleotide sequence and a sPAM and/or a sigRNAR in a $2^{nd}$ junction polynucleotide sequence is deleted with at least one gRNA and RdDe that recognize the sPAM and/or a sigRNAR to produce an INIR17 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR17 transgenic loci excision sites are provided herein.

In other embodiments, a segment comprising a INIR17 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur stepwise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a 5307 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR17 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are at least partially or essentially restored.

In certain embodiments, edited transgenic plant genomes provided herein can lack one or more selectable and/or scoreable markers found in an original event (transgenic locus). Original 5307 transgenic loci (events), including those set forth in SEQ ID NO:1), U.S. Pat. No. 8,466,346, the sequence of the 5307 locus in the deposited seed of accession No. PTA-9561 and progeny thereof, contain a selectable phosphomannose isomerase (pmi) transgene marker conferring an ability to grow on mannose. Transgenes encoding a phosphomannose isomerase (pmi) can confer the ability to grow on mannose. In certain embodiments provided herein, the DNA element comprising, consisting essentially of, or consisting of the ZmUbi promoter which is operably linked to a pmi coding region of a 5307 transgenic locus is absent from an INIR17 transgenic locus. or scoreable marker transgenes can be excised from an original transgenic locus by contacting the transgenic locus with one or more gene editing molecules which introduce double stranded breaks in the transgenic locus at the 5' and 3' end of the expression cassette comprising the selectable marker transgene (e.g., an RdDe and guide RNAs directed to PAM sites located at the 5' and 3' end of the expression cassette comprising the selectable marker transgenes) and selecting for plant cells, plant parts, or plants wherein the selectable or scoreable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable or scoreable marker transgene by eliminating or reducing promoter activity, introducing a missense mutation, and/or introducing a pre-mature stop codon. In certain embodiments, the selectable and/or scoreable marker transgene can be replaced by an introduced transgene. In certain embodiments, an original transgenic locus that was contacted with gene editing molecules which introduce double stranded breaks in the transgenic locus at the 5' and 3' end of the expression cassette comprising the selectable marker and/or scoreable transgene can also be contacted with a suitable donor DNA template comprising an expression cassette flanked by DNA homologous to remaining DNA in the transgenic locus located 5' and 3' to the selectable marker excision site. In certain embodiments, a coding region of the selectable and/or scoreable marker transgene can be replaced with another coding region such that the replacement coding region is operably linked to the promoter and 3' terminator or polyadenylation site of the selectable and/or scoreable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759, 618, 7,157,281, 6,852,915, 7,705,216, 10,316,330, 8,618, 358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR17 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell, b* 163::759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature,* 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.,* 11:636-646; Mohanta et al. (2017) *Genes* vol. 8, 12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fok1. This endonuclease must dimerize to cleave DNA. Thus, cleavage by Fok1 as part of a ZFN requires two adjacent and independent binding events, which must occur in both the correct orientation and with appropriate spacing to permit dimer formation. The requirement for two DNA binding events enables more specific targeting of long and potentially unique recognition sites. Fok1 variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fok1, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e.g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor DNA template (e.g., SEQ ID NO:16). In certain embodiments, integration of the donor DNA templates can be facilitated by use of a bacteriophage lambda exonuclease, a bacteriophage lambda beta SSAP protein, and an E. coli SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e.g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor DNA template (e.g., SEQ ID NO:).

Various treatments are useful in delivery of gene editing molecules and/or other molecules to a 5307 or INIR17 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., Azobacter sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g.; herbicide tolerance, insect resistance, and/or male sterility) are introduced into a 5307 or INIR17 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the 5307 or INIR17 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol [dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the 5307 or INIR17 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the 5307 or INIR17 plant cells in used in the methods provided herein can include dividing cells. Dividing cells can include those cells found in various plant tissues including leaves, meristems, and embryos. These tissues include but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR17 plant from a INIR17 plant cell that had been subjected to the gene editing or from a regenerable plant structure obtained from that INIR17 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR17 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic maize plant cell comprising an INIR17 transgenic locus that comprises a CMP promoter, an eCry3.1Ab coding region which is operably linked to said promoter, and a nopaline synthase terminator element, wherein said cell does not contain a ZmUbiInt promoter, an operably linked phosphomannose isomerase coding region and a second NOS terminator elements, wherein the CMP promoter, the eCry3.1Ab coding region which is operably linked to said promoter, and the NOS terminator element which is operably linked to said eCry3.1Ab coding region are located in the maize plant cell genomic location of the 5307 transgenic locus.

1b. A transgenic maize plant cell comprising an INIR17 transgenic locus that comprises (i) a CMP promoter, an eCry3.1Ab coding region which is operably linked to said promoter, and a nopaline synthase terminator element; and (ii) an insertion and/or substitution of a DNA element comprising a cognate guide RNA recognition site (CgRRS) in a DNA junction polynucleotide of said INIR17 transgenic locus, wherein the CMP promoter, the eCry3.1Ab coding region which is operably linked to said promoter, and the NOS terminator element which is operably linked to said eCry3.1Ab coding region are located in the maize plant cell genomic location of the 5307 transgenic locus.

1c. A transgenic maize plant cell comprising an INIR17 transgenic locus that comprises (i) a CMP promoter, an eCry3.1Ab coding region which is operably linked to said promoter, and a nopaline synthase terminator element; and (ii) a deletion of non-essential DNA in a DNA junction polynucleotide of said INIR17 transgenic locus, wherein the CMP promoter, the eCry3.1Ab coding region which is operably linked to said promoter, and the NOS terminator element which is operably linked to said eCry3.1Ab coding region are located in the maize plant cell genomic location of the 5307 transgenic locus.

1d. A transgenic maize plant cell comprising an INIR17 transgenic locus that comprises (i) a CMP promoter, an eCry3.1Ab coding region which is operably linked to said promoter, and a nopaline synthase terminator element; (ii) an insertion and/or substitution of a DNA element comprising a cognate guide RNA recognition site (CgRRS) in a DNA junction polynucleotide of said INIR17 transgenic locus and/or (iii) a deletion of non-essential DNA in a DNA junction polynucleotide of said INIR17 transgenic locus; wherein the CMP promoter, the eCry3.1Ab coding region which is operably linked to said promoter, and the NOS terminator element which is operably linked to said eCry3.1Ab coding region are located in the maize plant cell genomic location of the 5307 transgenic locus 2. The transgenic maize plant cell of embodiment 1a, 1b, 1c, or 1d, wherein said INIR17 transgenic locus comprises DNA corresponding to at least nucleotide number 1 to 3865 of SEQ ID NO:1 or an allelic variant thereof and nucleotide number 7415 to 8865 of SEQ ID NO:1 or an allelic variant thereof, wherein nucleotides corresponding to at least 4164 to 7355 of SEQ ID NO:1 or an allelic variant thereof are absent, optionally wherein said transgenic locus comprises SEQ ID NO: 40 or an allelic variant thereof.

3. The transgenic maize plant cell of embodiment 1a, wherein said INIR17 transgenic locus comprises the DNA molecule set forth in SEQ ID NO: 32, 33, or an allelic variant thereof; or transgenic maize plant cell of embodiment 1b, wherein said INIR17 transgenic locus comprises the DNA molecule set forth in SEQ ID NO: 29, 30, 33, or an allelic variant thereof.

4. The transgenic maize plant cell of embodiment 1c or 1d, wherein said INIR17 transgenic locus comprises a 5' DNA junction polynucleotide set forth as SEQ ID NO: 38, 39, or an allelic variant thereof or optionally comprises SEQ ID NO: 26, 27, 34, 36, or an allelic variant thereof.

5. The transgenic maize plant cell of embodiment 1a, 1c, or 1d wherein said INIR17 transgenic locus further comprises an insertion and/or substitution of a DNA element comprising a cognate guide RNA recognition site (CgRRS) in a DNA junction polynucleotide of said INIR17 transgenic locus.

6. The transgenic maize plant cell of embodiment 1b, 1d, or 5, wherein said cognate guide RNA recognition site (CgRRS) comprises SEQ ID NO: 17, wherein the insertion and/or substitution is in a 5' junction polynucleotide of said INIR17 transgenic locus.

7. The transgenic maize plant cell of embodiment 6, wherein said INIR17 transgenic locus comprising the CgRRS comprises the DNA molecule set forth in SEQ ID NO: 16, 29, 30, 33, or an allelic variant thereof.

8. The transgenic maize plant cell of embodiment 1a, 1b, 1c, or 1d, wherein said 5307 transgenic locus comprises the DNA molecule set forth in SEQ ID NO:1 or is present in seed deposited at the ATCC under accession No. PTA-9561, is present in progeny thereof, is present in allelic variants thereof, or is present in other variants thereof.

9. A transgenic maize plant part comprising the maize plant cell of any one of embodiments 1a, 1b, 1c, 1d, 2, 3, 4, 5, 6, 7, or 8, wherein said maize plant part is optionally a seed.

10. A transgenic maize plant comprising the maize plant cell of any one of embodiments 1a, 1b, 1c, 1d, 2, 3, 4, 5, 6, 7, or 8.

11. A method for obtaining a bulked population of inbred seed comprising selfing the transgenic maize plant of embodiment 10 and harvesting seed comprising the INIR17 transgenic locus from the selfed maize plant.

12. A method of obtaining hybrid maize seed comprising crossing the transgenic maize plant of embodiment 10 to a second maize plant which is genetically distinct from the first maize plant and harvesting seed comprising the INIR17 transgenic locus from the cross.

13. A DNA molecule comprising SEQ ID NO: 16, 26, 27, 28, 29, 32, 33, 34, 36, 38, 39, or 40.

14. A processed transgenic maize plant product comprising the DNA molecule of embodiment 13.

15. A biological sample containing the DNA molecule of embodiment 13.

16. A nucleic acid molecule adapted for detection of genomic DNA comprising the DNA molecule of embodiment 13, wherein said nucleic acid molecule optionally comprises a detectable label.

17. A method of detecting a plant cell comprising the INIR17 transgenic locus of any one of embodiments 1a, 1b, 1c, or 1d to 8, comprising the step of detecting DNA molecule comprising SEQ ID NO: 16, 26, 27, 28, 29, 32, 33, 34, 36, 38, 39, or 40.
18. A method of excising the INIR17 transgenic locus from the genome of the maize plant cell of any one of embodiments 1b, 1d, 5, 6, 7, or 8, comprising the steps of:
   (a) contacting the edited transgenic plant genome of the plant cell of embodiment 1b, 1d, 5, 6, 7, or 8 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
   (b) selecting a transgenic plant cell, transgenic plant part, or transgenic plant wherein the INIR17 transgenic locus flanked by the OgRRS and the CgRRS has been excised.
19. The method of embodiment 18, wherein the OgRRS is located in a 3' flanking DNA junction polynucleotide and comprises SEQ ID NO: 20 and wherein the CgRRS comprises an insertion or substitution of SEQ ID NO:17 in a 5' junction polynucleotide of said INIR17 transgenic locus.
20. The method of embodiment 19, wherein the insertion and/or substitution is in a 5' junction polynucleotide of the INIR17 transgenic locus corresponding to at least one of: (i) nucleotides 1350 to 1356 of SEQ ID NO:1; or (ii) nucleotides 1336 to 1342 of SEQ ID NO: 1.
21. The method of embodiment 19, wherein the CgRRS comprises the DNA molecule set forth in SEQ ID NO:16.
20a. A method of modifying a transgenic maize plant cell comprising: obtaining a 5307 maize event plant cell, a representative sample of which was deposited at the ATCC under accession No. PTA-9561, comprising a nucleotide sequence comprising a CMP promoter, a eCry3.1Ab coding region which is operably linked to said promoter, a first nopaline synthase (NOS) terminator element which is operably linked to said eCry3.1Ab coding region, a ZmUbiInt promoter and an operably linked phosphomannose isomerase coding region, and a second NOS terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said first NOS terminator, said ZmUbiInt promoter, and said operably linked phosphomannose isomerase coding region.
20b. A method of modifying a transgenic maize plant cell comprising: obtaining a 5307 maize event plant cell, a representative sample of which was deposited at the ATCC under accession No. PTA-9561, comprising a nucleotide sequence comprising a 5' junction polynucleotide, a CMP promoter, a eCry3.1Ab coding region which is operably linked to said promoter, a first nopaline synthase (NOS) terminator element which is operably linked to said eCry3.1Ab coding region, a ZmUbiInt promoter and an operably linked phosphomannose isomerase coding region, and a second NOS terminator element; and modifying said nucleotide sequence to: (i) substantially, essentially, or completely remove said first NOS terminator, said ZmUbiInt promoter, and said operably linked phosphomannose isomerase coding region; and (ii) delete and/or substitute one or more nucleotides of said 5' junction polynucleotide, optionally wherein one or more nucleotides or a polynucleotide sequence comprising a CgRRS are inserted into said 5' junction polynucleotide.
20c. A method of making transgenic maize plant cell comprising an INIR17 transgenic locus comprising:
   (a) contacting the transgenic plant genome of a maize 5307 plant cell with: (i) a first set of gene editing molecules comprising a first site-specific nuclease which introduces at least one first double stranded DNA break in a 5' junction polynucleotide of a 5307 transgenic locus; and (ii) a second set of gene editing molecules comprising a second site-specific nuclease which introduces a second double stranded DNA break between the eCry3.1Ab coding sequence and the first nopaline synthase (NOS) terminator of said 5307 transgenic locus and a third site specific nuclease which introduces a third double stranded DNA break between the phosphomannose isomerase coding region and DNA encoding the second nopaline synthase (nos) terminator element of said 5307 transgenic locus; and
   (b) selecting a transgenic maize plant cell, transgenic maize callus, and/or a transgenic maize plant comprising an INIR17 transgenic locus wherein one or more nucleotides of said 5' junction polynucleotide have been deleted and/or substituted, wherein the CMP promoter, the eCry3.1Ab coding region which is operably linked to the CMP promoter, and the second NOS terminator element of said 5307 transgenic locus are present, and wherein DNA of said 5307 transgenic locus comprising the first NOS terminator, the ZmUbiInt promoter and the phosphomannose isomerase coding region is absent, thereby making a transgenic maize plant cell comprising an INIR17 transgenic locus.
21. The method of embodiment 20c, comprising:
   (a) contacting the transgenic plant genome of a maize 5307 plant cell with: (i) a first set of gene editing molecules comprising a first site-specific nuclease which introduces at least one first double stranded DNA break between nucleotide residues corresponding to nucleotides 1350 to 1356 of SEQ ID NO:1; and/or nucleotides 1336 to 1342 of SEQ ID NO: 1; and (ii) a second set of gene editing molecules comprising a second site-specific nuclease which introduces a second double stranded DNA break between nucleotide residues corresponding to nucleotide number 3866 to 3895 of SEQ ID NO:1 and a third site specific nuclease which introduces a third double stranded DNA break between nucleotide residues corresponding to nucleotide number 7356 to 7415 of SEQ ID NO:1; and
   (b) selecting a transgenic maize plant cell, transgenic maize plant callus, and/or a transgenic maize plant wherein one or more nucleotides corresponding to nucleotide number 1336 to 1356 of SEQ ID NO:1 have been deleted and/or substituted, wherein nucleotides corresponding to at least nucleotide number 4164 to 7355 of SEQ ID NO:1 have been deleted and/or replaced, and wherein nucleotides corresponding to at least nucleotide number 1360 to 3865 and 7415 to 8865 of SEQ ID NO:1 are retained.
22. The method of embodiment 20c or 21, further comprising contacting the transgenic plant genome of the maize 5307 plant cell with a donor DNA template comprising a cognate guide RNA recognition site (CgRRS), wherein said CgRRS optionally comprises a polynucleotide set forth in SEQ ID NO:17; and selecting a transgenic plant cell wherein said CgRRS has integrated into and/or replaced one or more nucleotides corresponding to at least one of nucleotides of SEQ ID NO:1.

23. The method of any one of embodiments 20c or 21, wherein the gene editing molecules comprise: (i) a zinc finger nuclease; (ii) a TALEN; and/or (iii) an RNA dependent DNA endonuclease (RdDe) and a guide RNA.

24. The method of embodiment 23, wherein the RNA dependent DNA endonuclease (RdDe) comprises a Cas12a RdDe and wherein the guide RNA of said first set of gene editing molecules comprises SEQ ID NO:8, 9, 10, and/or 11, the guide RNA of said second set of gene-editing molecules comprises SEQ ID NO:12, and the guide RNA of said third set of gene-editing molecules comprises SEQ ID NO:13.

25. The method of any one of embodiments 20a, b, or c to 24, further comprising the step of regenerating transgenic maize plant callus and/or a transgenic maize plant comprising the modification or the INIR17 transgenic locus from said transgenic maize plant cell selected in step (c).

26. The method of any one of embodiments 20a, b, or c to 25, further comprising the step of harvesting a transgenic maize plant seed comprising the modification or the INIR17 transgenic locus from the transgenic maize plant comprising the modification or the INIR17 transgenic locus.

27. A transgenic maize plant cell comprising a modification or an INIR17 transgenic locus made by the method of any one of embodiments 20a, b, or c to 25.

28. Transgenic maize plant callus comprising a modification or an INIR17 transgenic locus made by the method of any one of embodiments 20a, b, or c to 25.

29. A transgenic maize plant comprising a modification or an INIR17 transgenic locus made by the method of any one of embodiments 20a, b, or c to 25.

30. A transgenic maize plant seed comprising a modification or an INIR17 transgenic locus made by the method of embodiment 26.

EXAMPLES

Example 1. Application of a Cas12a and Guide RNAs to Change or Excise the 5'-T-DNA Junction Sequence in the 5307 Event Maize Event 5307 5'-junction sequence shown in FIG. 6A an 6B has 4 Cas12a recognition sequences close by, gRNA-1 (SEQ ID NO:8; tttcccgccttcagtttaaactatcag), gRNA-2 (SEQ ID NO:9; tttaaactatcagttcgtgagttgaat), gRNA-3 (SEQ ID NO:10; tttagaggcacaccggacagcgtatcg), and gRNA-4 (SEQ ID NO:11; tttaaactgaaggcgggaaacgacaat) that can be used to modify some of the 5' junction sequence or eliminate most of it. There are a few possible iterations of this approach. Two depend on gRNA-1 and gRNA-2 alone to disrupt Maize Event 5307 5'-junction sequence. Two others combine gRNA-3 with either gRNA-1 or gRNA-4 to eliminate most of Maize Event 5307 junction sequence. In certain instances, gRNA-1 (SEQ ID NO:8) is used to modify the 5' DNA junction polynucleotide and obtain a modified 5' junction polynucleotide comprising SEQ ID NO:34. In certain instances, gRNA-2 (SEQ ID NO:9) is used to modify the 5' DNA junction polynucleotide and obtain a modified 5' junction polynucleotide comprising SEQ ID NO:28.

The Cas12a nuclease and the single or combined gRNAs are introduced into Maize Event 5307. This can be accomplished in different ways. The first is to encode expression of the Cas12a nuclease and gRNA(s) on a T-DNA and insert it into Maize Event 5307 via *Agrobacterium*-mediated transformation. Alternatively, the T-DNA can be transformed into any convenient maize line, and then crossed with Maize Event 5307 to combine the Cas12a ribonucleoprotein expressing T-DNA with Maize Event 5307. The Cas12a nuclease and gRNAs can also be assembled in vitro then delivered to Maize Event 5307 explants as ribonucleoprotein complexes using a biolistic approach (Svitashev et al., 2016; doi: 10.1038/ncomms13274). Also, a plasmid encoding a Cas12a nuclease and the gRNA(s) can be delivered to Maize Event 5307 explants using a biolistic approach. This will produce plant cells that have a high likelihood of incurring mutations that disrupt Maize Event 5307 5'-junction sequence. To use the *Agrobacterium* approach a binary vector that contains a strong constitutive expression cassette like the ZmUbi1 promoter::ZmUbi1 terminator driving Cas12a, a PolII or PolIII gene cassette driving the Cas12a gRNA(s) and a CaMV 35S:PAT:NOS or other suitable plant selectable marker is constructed. An expression cassette driving a fluorescent protein like mScarlet may also be useful to the plant transformation process. Constructs are transformed into *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produce callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remain on Pre-Regeneration media for 7 days. Calli beginning to initiate shoots are transferred to Regeneration medium with 7.5 mg/L PPT in Phytatrays and cultured in light at 27-28° C. Shoots that reach the top of the Phytatray with intact roots are transferred to Shoot Elongation medium prior to transplant into soil and gradual acclimatization to greenhouse conditions.

When a sufficient amount of viable tissue is obtained, it can be screened for mutations at Maize Event 5307 5'-junction sequence, using a PCR-based approach. One way to screen is to design DNA oligonucleotide primers that flank and amplify Maize Event 5307 junction plus surrounding sequence. For example, the primers (5'-tgctgcg-catgggcgcaccggacag-3'; SEQ ID NO:41) and (5'-caattcctgcagcgttgcggttctg-3'; SEQ ID NO:42) will produce a ~293 bp product that can be analyzed for edits at the target site. The size of this product will vary based on the nature of the edit. Amplicons can be sequenced directly using an amplicon sequencing approach or ligated to a convenient plasmid vector for Sanger sequencing. Those plants in which Maize Event 5307 5'-junction sequence is disrupted are selected and grown to maturity. The DNA encoding the Cas12a reagents can be segregated away from the modified junction sequence in a subsequent generation.

Example 2. Insertion of a CgRRS Element in the 5'-Junction of the 5307 Event

This example describes the construction of plant expression vectors for *Agrobacterium* mediated maize transformation. Two plant gene expression vectors are prepared. Plant expression cassettes for expressing a Bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO:135, SEQ ID NO:134, and SEQ ID NO:133 of US Patent Application Publication 20200407754, respectively, and incorporated herein by reference in their entireties. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A donor DNA template sequence (SEQ ID NO:16) that targets the 5'-T-DNA junction of Maize Event 5307 for insertion of a 27 base pair heterologous sequence, that is identical to a Cas12a recognition site at the 3'-junction of the Maize Event 5307 T-DNA insert, by HDR is constructed. The donor DNA template sequence includes a replacement template with desired insertion region (27 base pair long sequence of SEQ ID NO: 17; TTTACAC-CACAATATAccctcttccct) flanked on both sides by homology arms about 550 bp in length. The homology arms match (i.e., are homologous to) gDNA (genomic DNA) regions flanking the target gDNA insertion site. The replacement template region comprising the donor DNA template is flanked at each end by DNA sequences identical to Maize Event 5307 5' polynucleotide sequence recognized by an RNA-guided nuclease and one or more gRNA(s) (e.g. gRNAs comprising SEQ ID NO:8 or 9). In certain cases, a deletion is made in the targeted Maize Event 5307 5' polynucleotide sequence (e.g., using gRNAs comprising SEQ ID NO:10 (gRNA-3) and SEQ ID NO: 8 in combination or by using gRNAs comprising SEQ ID NO:10 (gRNA-3) and SEQ ID NO: 11 (gRNA-4) in combination).

A plant expression cassette that provides for expression of the RNA-guided sequence-specific Cas12a endonuclease is constructed. A plant expression cassette that provides for expression of a guide RNA complementary to sequences adjacent to the insertion site (e.g. gRNAs comprising SEQ ID NO:8 or 9) is constructed. An *Agrobacterium* superbinary plasmid transformation vector containing a cassette that provides for the expression of the phosphinothricin N-acetyltransferasesynthase (PAT) protein is constructed. Once the cassettes, donor sequence and *Agrobacterium* superbinary plasmid transformation vector are constructed, they were combined to generate two maize transformation plasmids.

A maize transformation plasmid is constructed with the PAT cassette, the RNA-guided sequence-specific endonuclease cassette, the guide RNA cassette, and Maize Event 5307 5'-junction polynucleotide donor DNA template sequence into the *Agrobacterium* superbinary plasmid transformation vector (the control vector).

A maize transformation plasmid is constructed with the PAT cassette, the RNA-guided sequence-specific endonuclease cassette, the guide RNA cassette, the SSB cassette, the lambda beta SSAP cassette, the Exo cassette, and the Maize Event 5307 5'-junction polynucleotide donor DNA template into the *Agrobacterium* superbinary plasmid transformation vector (the lambda red vector).

All constructs are delivered from superbinary vectors in *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remained on Pre-Regeneration media for 7 days. Calli beginning to initiate shoots are transferred to Regeneration medium with 7.5 mg/L PPT in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the Maize Event 5307 junction sequence, using a PCR-based approach. The PCR primer on the 5'-end can be 5'-aagcaaggthagaagactcctcca-3' (SEQ ID NO:18) and the PCR primer on the 3'-end is 5'-gggaagcccaccacgcccagcaggt-3' (SEQ ID NO:19). These primers that flank donor DNA homology arms are used to amplify the Maize Event 5307 5'-junction sequence. The correct donor sequence insertion will produce a 1398 bp product. Amplicons can be sequenced directly using an amplicon sequencing approach or ligated to a convenient plasmid vector for Sanger sequencing. Those plants in which the Maize Event 5307 5' junction polynucleotide sequence now contains the intended CgRRS (e.g., Cas12a recognition sequence in SEQ ID NO:17) are selected and grown to maturity. The T-DNA encoding the Cas12a reagents can be segregated away from the modified junction sequence in a subsequent generation. The resultant INIR12 transgenic locus comprising the CgRRS and OgRRS (e.g. which each comprise SEQ ID NO:20 and an operably linked PAM site) can be excised using Cas12a and a suitable gRNA which hybridizes to DNA comprising SEQ ID NO:20 at both the OgRRS and the CgRRS. An example of an INIR12 locus comprising the intended CgRRS in SEQ ID NO:17 is provided as SEQ ID NO:29. Another example of an INIR12 locus comprising the intended CgRRS in SEQ ID NO:17 is provided as SEQ ID NO:30.

Example 3. Deletion of the 5307 PMI Gene Cassette

The ZmUbi1::PMI coding sequence in Maize Event 5307 transgenic maize performs no useful function with respect to field productivity. It can be removed using a Cas12a-mediated genomic DNA deletion approach. The procedure calls for creating an *Agrobacterium* transformation vector encoding the Cas12a nuclease, the Maize Event 5307 PMI 5' guide RNA encoded by 5'-tttccccgatcgttcaaacatttggca-3' (SEQ ID NO:12), the Maize Event 5307 PMI 3' guide RNA encoded by 5'-tttacaacaagctgtaagagcttactg-3'; (SEQ ID NO:13), and a plant selectable marker gene.

A binary vector that contains a strong constitutive expression cassette like the ZmUbi1 promoter::ZmUbi1 terminator driving Cas12a, a PolII or PolIII gene cassette driving the Cas12a gRNAs and a CaMV 35S:PAT:NOS or other suitable plant selectable marker is constructed. An expression cassette driving a fluorescent protein like mScarlet may also be useful to the plant transformation process and included in the binary vector.

The aforementioned binary vector is transformed into maize using the procedure essentially as outlined in Example 1. The regenerated plants can be screened with the primer set below to identify individuals that have lost the first NOS::ZmUbi1::PMI fragment. The primers span 4097 bases in the intact insert. If both cuts occur and the ends are ligated together, this will produce a ~652 bp amplicon. This is verified by DNA sequence analysis. The primer set includes 5307-PMI-ampseq-5' (5'-gagttcgtgcccgccgaggtgacct-3'; SEQ ID NO:23) and 5307-PMI-ampseq-3' (5'-tgtccggtgcaccctttgccagtgg-3'; SEQ ID NO:24).

Example 4. Introduction of a CgRRS into an INIR17 Maize Plant Comprising a Deletion of the 5307 ZmUbi1::PMI Fragment Maize plants comprising Maize plants comprising the deletion of the Maize Event 5307 NOS::ZmUbi1::PMI fragment are subjected to the procedures for integration of the SEQ ID NO:16 donor DNA template set forth in Example 2 to provide for a resultant INIR12 transgenic locus comprising the CgRRS and OgRRS (e.g. which each comprise SEQ ID NO:20 and an operably linked PAM site) where the NOS::ZmUbi1::PMI fragment is absent. This resultant INIR12 transgenic locus can be excised using Cas12a and a suitable gRNA which hybridizes to DNA comprising SEQ ID NO:27 at both the OgRRS and the CgRRS. An example of a INIR12 transgenic locus comprising the deletion of the Maize Event 5307 NOS::ZmUbi1::PMI fragment, the CgRRS sequence, and the OgRRS sequence (e.g. which each comprise SEQ ID NO:20 and an operably linked PAM site) is set forth in SEQ ID NO:33.

The breadth and scope of the present disclosure should not be limited by any of the above-described embodiments.

---

What is claimed is:

1. A transgenic maize plant cell comprising an INIR17 transgenic locus comprising a cognate guide RNA recognition site (CgRRS) in a 5' junction polynucleotide of a 5307 maize event transgenic locus, an originator guide RNA recognition site (OgRRS) in a 3' junction polynucleotide of the 5307 maize event transgenic locus, and a deletion of the $1^{st}$ NOS terminator, the ZmUbiInt promoter, and the phosphomannose isomerase coding region of the 5307 maize event transgenic locus, wherein said INIR17 transgenic locus comprises the DNA molecule set forth as SEQ ID NO: 33 or an allelic variant thereof.

2. The transgenic maize cell of claim 1, wherein the INIR17 transgenic locus comprises the DNA molecule of SEQ ID NO: 33.

3. A transgenic maize plant part comprising the maize plant cell of claim 1.

4. The transgenic maize plant part of claim 3, wherein said part is a seed.

5. A transgenic maize plant comprising the maize plant cell of claim 1.

6. A method for obtaining a bulked population of inbred seed comprising selfing the transgenic maize plant of claim 5 and harvesting seed comprising the INIR17 transgenic locus from the selfed maize plant.

7. A method of obtaining hybrid maize seed comprising crossing the transgenic maize plant of claim 5 to a second maize plant which is genetically distinct from the first maize plant and harvesting seed comprising the INIR17 transgenic locus from the cross.

8. A DNA molecule comprising SEQ ID NO: 33.

9. A processed transgenic maize plant product comprising the DNA molecule of claim 8.

10. A biological sample containing the DNA molecule of claim 8.

11. A method of detecting a maize plant cell comprising the transgenic locus of claim 1, comprising the step of detecting a DNA molecule comprising SEQ ID NO: 16 or 40.

12. A method of excising the INIR17 transgenic locus comprising a DNA molecule of SEQ ID NO: 33 or an allelic variant thereof from the genome of the maize plant cell of claim 1, comprising the steps of:
  (a) contacting the genome of the maize plant cell with: (i) a Cas12 RNA dependent DNA endonuclease (RdDe); and (ii) a guide RNA (gRNA) capable of hybridizing to the guide RNA hybridization site of the originator guide RNA recognition site (OgRRS) and the cognate guide RNA recognition site (CgRRS) of the transgenic locus; wherein the Cas12 RdDe recognizes a OgRRS/gRNA and a CgRRS/gRNA hybridization complex; and,
  (b) selecting a transgenic plant cell, transgenic plant part, or transgenic plant wherein the transgenic locus flanked by the OgRRS and the CgRRS has been excised.

* * * * *

SEQUENCE LISTING

```
Sequence total quantity: 42
SEQ ID NO: 1           moltype = DNA  length = 8865
FEATURE                Location/Qualifiers
source                 1..8865
                       mol_type = other DNA
                       organism = synthetic construct
SEQUENCE: 1
tacaagaata ttgagacgtg agtacatagc attggcattt tcattagcaa gcatttcaaa   60
agaatttaat tttctcatag caatgtgata tctctcctca cgctcaattc tagttccttc  120
atgtagagca catatgtcca tccacaaatc atgacaattt ttatggtttc taactctatt  180
aaacacatct ttgcaaaggc ctctaaaaag ggtgtttttg gccttagcat tccatttctc  240
atagttcaac tcttcaccta caagatttgt gggatctcta ggttcgggga atctttgtgt  300
ggcggctttg tagacaccaa tgtctatagc ctctaaatat gcttccatac gaattttcca  360
atatggaaaa tcgtcaccat aaaaaacggg agaaggtcca tccccaccgg acatcgttac  420
tctagcggtt aagctaatct aagagcaaca aggctcttat accaattgaa aggatcacga  480
tgcccaagag gggggttga attgggcttt tctaaaaatc aacactaact aaaatctaag  540
caagagccca acttcacccc gacaactagc actaagagaa taatactaga aatacaacaa  600
tgctaagata atacttcaaa tacttgctaa acaaatacac aatgtaaaat acttgaatta  660
agtgcggaat gtaaagcaag gtttagaaga ctcctccaat ttttctagag gtatcaaaga  720
gtcggcactc tcccctagtc ctcgttggag cacctgccta agggtatcgc tctcccttgg  780
tcatcgcaag aaccaagtgc tcacaacgag atgatccttt gccactccgg cgcggtggat  840
ccctcacgac cgcttacaaa cttgagtcgg gtcaccaaca agatctccac ggtgatcacc  900
gagctcccaa cgccaccaag ccgtctaggt gatgccgatc accaagagta ataagccata  960
gactttcact tgaccaagag aagcctaatg catgcggtgt gtgctctagg tggctctcgc 1020
tagcgttaat gaggtccaaa tgcgggatta agattctcaa gtcacctcac taggctttgt 1080
ggtgcttgca atgctctacc aatgtgtagg agtaaatgtg ggcagcaaga ccatcaatat 1140
ggtaggtgga tggggtataa atagccctca cccaccaact agccattacc aggaatctgc 1200
tgcgcatggg cgcaccggac agtccggtgt gccaccggtg cgccaacggt cgactcaaac 1260
ggctagttct gacagctage cgttggacag atggcatacc ggacagtccg atacgctgtc 1320
cggtgtgcct ctaaaattca actcacgaac tgatagttta aactgaaggc gggaaacgac 1380
aatctgatca tgagcggaga attaagggag tcacgttatg accccgccg atgacgcggg 1440
acaagccgtt ttacgtttgg aactgacaga accgcaacgc tgcaggaatt ggccgcagct 1500
gccatttaaa tcaattgggc gcgccgaatt cgagctcggt acaagcttct ggcagacaaa 1560
gtggcagaca tactgtccca caaatgaaga tggaatctgt aaaagaaaac gcgtgaaata 1620
```

-continued

```
atgcgtctga caaaggttag gtcggctgcc tttaatcaat accaaagtgg tccctaccac 1680
gatgaaaaa ctgtgcagtc ggtttggctt tttctgacga acaaataaga ttcgtggccg 1740
acaggtgggg gtccaccatg tgaaggcatc ttcagactcc aataatggag caatgacgta 1800
agggcttacg aaataagtaa gggtagtttg ggaaatgtcc actcacccgt cagtctataa 1860
atacttagcc cctccctcat tgttaaggga gcaaggatcc accatgacta gtaacggccg 1920
ccagtgtgct ggtattcgcc cttatgacgg ccgacaacaa caccgaggcc tggacagcag 1980
caccaccaag gacgtgatcc agaagggcat cagcgtggtg ggcgacctgc tgggcgtggt 2040
gggcttcccc ttcggcggcg ccctggtgag cttctacacc aacttcctga acaccatctg 2100
gcccagcgag gacccctgga aggccttcat ggagcaggtg gaggccctga tggaccagaa 2160
gatcgccgac tacgccaaga acaaggcact ggccgagcta cagggcctcc agaacaacgt 2220
ggaggactat gtgagcgccc tgagcagctg gcagaagaac cccgctgcac cgttccgcaa 2280
cccccacagc cagggccgca tccgcgagct gttcagccag gccgagagcc acttccgcaa 2340
cagcatgccc agcttcgcca tcagcggcta cgaggtgctg ttcctgacca cctacgccca 2400
ggccgccaac acccacctgt tcctgctgaa ggacgcccaa atctacggag aggagtgggg 2460
ctacgaagaag gaggacatcg ccgagttcta caagcgccac ctgaagctga cccaggagta 2520
caccgaccac tgcgtgaagt ggtacaacgt gggtctagac aagctccgcg gcagcagcta 2580
cgagagctgg gtgaacttca accgctaccg ccgcgagatg accctgaccg tgctggacct 2640
gatcgccctg ttccccctgt acgacgtgcg cctgtacccc aaggaggtga agaccgagct 2700
gacccgcgac gtgctgaccg accccatcgt gggcgtgaac aacctgcgcg gctacgcac 2760
cacctttcagc aacatcgaga actacatccg caagccccac ctgttcgact acctgcaccg 2820
catccagttc cacacgcgtt tccagcccgg ctactacggc aacgacagct tcaactactg 2880
gagcgccaac tacgtgagca cccgcccag catcggcagc aacatca tcaccagccc 2940
cttctacggc aacaagagca gcgagcccgt gcagaacctt gagttcaacg gcgagaaggt 3000
gtaccgcgcc gtggctaaca ccaacctggc cgtgtggccc tctgcagtgt acagcggcgt 3060
gaccaaggtg gagttcagcc agtacaacga ccagaccgac gaggccagca cccagaccta 3120
cgacagcaag cgcaacgtgg gcgccgtgag ctgggacagc atgaccagc tgccccccga 3180
gaccaccgac gagcccctgg agaagggcta cagccaccag ctgaactacg tgatgtgctt 3240
cctgatgcag ggcagccgcg gcaccatccc cgtgctgacc tggacccaca gagcgtcga 3300
cttcttcaac atgatcgaca gcaagaagat cacccagctg cccctgacca agagcaccaa 3360
cctgggcgac ggcaccacgc tggtgaaggg ccccggcttc accggcggcg acatcctgcg 3420
ccgcaccagc cccggccaga tcagcaccct cgcgtgaac atcaccgccc cctgagcca 3480
gcgctaccgc gtccgcatcc gctacgccag caccaccaac ctgcagtcc acaccagcat 3540
cgacggccgc cccatcaacc agggcaactt cagcgccacc atgagcagcg gcagcaacct 3600
gcagagcggc agcttccgca ccgtgggctt caccaccccc ttcaacttca gcaacggcag 3660
cagcgtgttc accctgagcg cccacgtgtt caacagcggc aacgaggtgt acatcgaccg 3720
catcgagttc gtgcccgccg aggtgaccctt cgaggccgag tacgacctgg agagggctca 3780
gaaggccgtg aacgagctgt tcaccagcag caaccagatc ggcctgaaga ccgacgtgac 3840
cgactaccac atcgatcagg tgtaggagct gagctctaga tccccgaatt tccccgatcg 3900
ttcaaacatt tggcaataaa gtttcttaag attgaatcct gttgccggtc ttgcgatgat 3960
tatcatataa tttctgttga attacgttaa gcatgtaata attaacatgt aatgcatgac 4020
gttatttatg agatgggttt ttatgattag agtcccgcaa ttatacattt aatacgcgat 4080
agaaaacaaa atatagcgcg caaactagga taaattatcg cgcgcggtgt catctatgtt 4140
actagatcgg gaattgggta ccagctgca tgcctgcagg gcagcgtgac ccggtcgtgc 4200
ccctctctag agataatgag cattgcatgt ctaagttata aaaaattacc acatatttt 4260
tttgtcacac ttgtttgaag tgcagttat ctatctttat acatatttt aaactttact 4320
ctacgaataa tataatctat agtactacaa taatatcagt gttttagaga atcatataaa 4380
tgaacagtta gacatggtct aaaggacaat tgagtatttt gacaacagga ctctacagtt 4440
ttatctttttt agtgtgcatg tgttctcctt ttttttttgca aatagcttca cctatataat 4500
acttcatcca ttttattagt acatccattt agggtttagg gttaatggtt tttatagact 4560
aatttttta gtacatctat tttattctat tttagcctct aaattaagaa aactaaaact 4620
ctattttagt ttttttattt aataatttag atataaaata gaataaaata aagtgactaa 4680
aaattaaaca aatacccttt aagaaattaa aaaaactaag gaaacatttt tcttgtttcg 4740
agtagataat gccagcctgt taaacgccgt cgacgagtct aacggacacc aaccagcgaa 4800
ccagcagcgt cgcgtcgggc caagcgaagc agacggcacg gcatctctgt cgctgcctct 4860
ggaccccctct cgagagttcc gctccaccgt tggacttgct ccgctgtcgg catccagaaa 4920
ttgcgtggcg gagcggcaga cgtgagccgg cacggcaggc ggcctcctcc tcctctcacg 4980
gcaccggcag ctacggggga ttcctttccc accgctcctt cgcttttcct tcctcgcccg 5040
ccgtaataaa tagacacccc ctccacaccc tctttcccca acctcgtgtt gttcggagcg 5100
cacacacaca caaccagatc tcccccaaat ccacccgtcg cgacctccgc ttcaaggtac 5160
gccgctcgtc ctcccccccc ccccctctct accttctcta gatcggcgtt ccggtccatg 5220
gttagggccc ggtagttcta cttctgttca tgtttgtgtt agatccgtgt ttgtgttaga 5280
tccgtgctgc tagcgttcgt acacggatgc gacctgtacg tcagcacgt tctgattgct 5340
aacttgccag tgtttctctt tggggaatcc tgggatggct ctagccgttc cgcagacggg 5400
atcgatttca tgatttttt tgtttcgttg cataggggtt ggttgccct tttccttat 5460
ttcaatatat gccgtgcact tgtttgtcgg gtcatctttt catgcttttt tttgtcttgg 5520
ttgtgatgat gtggtctggt ggggcggtcg ttctagatcg gagtagaatt ctgtttcaaa 5580
ctacctggtg gatttattaa ttttggatct gtatgtgtgt gccatacata ttcatagtta 5640
cgaattgaag atgatggatg gaaatatcga tctaggatag gtatacatgt tgatgcgggt 5700
tttactgatg catatacaga gatgctttt gttcgcttgg ttgtgatgat gtggtgtggt 5760
tgggcggtcg ttcattcgtt ctagatcgga gtagaatact gtttcaaact acctggtgta 5820
tttattaatt ttggaactgt atgtgtgtgt catacatctt catagttacg agtttaagat 5880
ggatggaaat atcgatctag gataggtata catgttgatg tgggttttac tgatgcatat 5940
acatgatggc atatgcagca tctattcata tgctctaacc ttgagtacct atctattata 6000
ataaacaagt atgttttata attatttga tcttgataa cttggatgat ggcatatgca 6060
gcagctatat gtggattttt ttagcccgtc cttcatacgc tatttatttg cttggtactg 6120
tttctttttgt cgatgctcac cctgttgttt ggtgttactt ctgcagggat ccccgatcat 6180
gcaaaaactc attaactcag tgcaaaacta tgcctgggc agcaaaacgg cgttgactga 6240
actttatggt atggaaaatc cgtccagcca gccgatggcc gagctgtgga tgggcgcaca 6300
tccgaaaagc agttcacgag tgcagaatgc cgccggagat atcgtttcac tgcgtgatgt 6360
```

```
gattgagagt gataaatcga ctctgctcgg agaggccgtt gccaaacgct ttggcgaact   6420
gcctttcctg ttcaaagtat tatgcgcagc acagccactc tccattcagg ttcatccaaa   6480
caaacacaat tctgaaatcg gttttgccaa agaaaatgcc gcaggtatcc cgatggatgc   6540
cgccgagcgt aactataaag atcctaacca caagccggag ctggttttg cgctgacgcc    6600
tttccttgcg atgaacgcgt ttcgtgaatt ttccgagatt gtctccctac tccagccggt   6660
cgcaggtgca catccggcga ttgctcactt tttacaacag cctgatgccg aacgtttaag    6720
cgaactgttc gccagcctgt tgaatatgca gggtgaagaa aaatcccgcg cgctggcgat    6780
tttaaaatcg gccctcgata gccagcaggg tgaaccgtgg caaacgattc gtttaatttc    6840
tgaattttac ccggaagaca gcggtctgtt ctcccccgta ttgctgaatg tggtgaaatt    6900
gaaccctggc gaagcgatgt tcctgttcgc tgaaacaccg cacgcttacc tgcaaggcgt    6960
ggcgctggaa gtgatggcaa actccgataa cgtgctgcgt gcgggtctga cgcctaaata    7020
cattgatatt ccggaactgg ttgccaatgt gaaattcgaa gccaaacggg ctaaccagtt    7080
gttgacccag ccggtgaaac aaggtgcaga actggacttc ccgattccag tggatgattt    7140
tgccttctcg ctgcatgacc ttagtgataa agaaaccacc attagccagc agagtgccgc    7200
catttttgttc tgcgtcgaag gcgatgcaac gttgtggaaa ggttctcagc agttacagct    7260
taaaccgggt gaatcagcgt ttattgccgc caacgaatca ccggtgactg tcaaaggcca    7320
cggccgttta gcgcgtgttt acaacaagct gtaagagctt actgaaaaaa ttaacatctc    7380
ttgctaagct gggagctcga tccgtcgacc tgcagatcgt tcaaacattt ggcaataaag    7440
tttcttaaga ttgaatcctg ttgccggtct tgcgatgatt atcatataat ttctgttgaa    7500
ttacgttaag catgtaataa ttaacatgta atgcatgacg ttatttatga tgggtttt      7560
tatgattaga gtcccgcaat tatacattta atacgcgata gaaaacaaaa tatagcgcgc    7620
aaactaggat aaattatcgc gcgcggtgtc atctatgtta ctagatctgc tagccctgca    7680
ggaaatttac cggtgcccgg gcggccagca tggccgtatc cgcaatgtgt tattaagttg    7740
tctaagcgtc aatttgttta caccacaata taccctcttc cctgggccag gctgggccca    7800
ctggcaaagg gtgcaccgga cagtccggtg ccccaaagcc agaaaccctg cgttctgttt    7860
tgtgctgttt tttcaatttg gttttgttc taacttgtga gtatgttcta gagttacacc     7920
tagcactata tgtgagtgtg aatatgcacc aacactacac tagaactctt ttggtcaaac    7980
tacttatcga caaccctct ttatagtacg gctaaaacaa aataaagac ctaactatat      8040
cacgagtgtc cgcaactcct tgacactcgg aatacgaaca ccttcacttt ttgtttcgtc    8100
gctttagccg ttgcttcaag ttttttatctc cgggattgtt ttcaccattg tagtacatct    8160
acctgtaatg cgacctaact taccattgc ctctgcaaaa cacatgttag tcacatataa      8220
aattacgttg tcattaatca ctaaaaccaa ccaggggcct agatgctttc tagtttaaat    8280
ccccaacaag tcaaaattct ttctattttt ttttgcaagt tccaattgac atctgaaagg    8340
ttgtaaggta cacgtttggc tctcattgat aacgggggaa agatacagtg caaaccacca    8400
tataatgacc cacttctaat cgaatggacc tgtaacgacg aaataccctg tgagaactat    8460
ggttcactca tgttaattca ttgaaattgt tgtagtgaat tgacatggtt gggagcctgc    8520
ttagagagta tagattgtca cttttttttg gaccgcaact tattttttaaa agatattgcg    8580
atcgcttgtt tagtagctgt ttcaggcccc aatgcagttt ctatcgtgat ccatttaagt    8640
cactcaacat tctcatactt ctcatttttgc attaattcat tccaatctcc actactataa    8700
aatactagct tcgatggtcg tcatacgcca tgcacgaagc atgtagatca atccgcatac    8760
cagtgggcat ctatagatag gctgtgaaaa ccacccaaat ccctactagt ggacatttta    8820
tctatagatg gaccgtgaga aaccacacaa gtctaacacg acagg                    8865

SEQ ID NO: 2             moltype = DNA   length = 1093
FEATURE                  Location/Qualifiers
source                   1..1093
                         mol_type = other DNA
                         organism = synthetic construct
SEQUENCE: 2
ccctcttccc tgggccaggc tgggcccact ggcaaagggt gcaccggaca gtccggtgcc     60
ccaaagccag aaaccctagc ttctgttttt tgctgttttt tcaatttggt ttttgttcta   120
acttgtgagt atgttctaga gttcaccta gcactatatg tgagtgtgaa tatgcaccaa    180
cactacacta gaactctttt ggtcaaacta cttatcgaca ccctctcttt atagtacgg    240
taaaacaaaa taaagacct aactatatca cgagtgtccg caactccttg acactcggaa     300
tacgaagacc ttcactttt tgtttcgtcg ctttagccgt gcttcaagtt tttatctccg    360
ggattgtttt caccattgta gtacatctac ctgtaatgcg acctaactta ccatttgcct    420
ctgcaaaaca catgttagtc acatataaaa ttacgttgtc attaatcact aaaaccaacc    480
aggggcctag atgctttcta gttttaaatcc ccaacaagtc aaaattcttt ctatttttttt   540
ttgcaagttc caattgacat ctgaaaggtt gtaaggtaca cgtttggctc tcattgataa    600
cgggggaaag atacagtgca aaccaccata taatgaccca cttctaatcg aatggaccta    660
taacgacgaa ataccctgtg agaactatgt tcactcatgt taattcatt gaaattgttg     720
tagtgaattg acatggttgg gagcctgctt agagagtata gattgtcact tttttttgga    780
ccgcaactta ttttttaaaag atattgcgat cgcttgttta gtagctgttt caggcccca    840
tgcagtttct atcgtgatcc atttaagtca ctcaacattc tcatacttct cattttgcat    900
taattcattc caatctccac tactataaaa tactagcttc gatggtcgtc atacgccatg    960
cacgaagcat gtagatcaat ccgcataca gtgggcatct atagataggc tgtgaaaacc    1020
acccaaatcc ctactagtgg acattttatc tatagatgga ccgtgagaaa ccacacaagt   1080
ctaacacgac agg                                                      1093

SEQ ID NO: 3             moltype = DNA   length = 20
FEATURE                  Location/Qualifiers
source                   1..20
                         mol_type = other DNA
                         organism = synthetic construct
SEQUENCE: 3
ccacaatata ccctcttccc                                                 20
```

```
SEQ ID NO: 4            moltype = DNA   length = 58
FEATURE                 Location/Qualifiers
source                  1..58
                        mol_type = other DNA
                        organism = synthetic construct
SEQUENCE: 4
aagcgtcaat ttgtttacac cacaatatac cctcttccct gggccaggct gggcccac       58

SEQ ID NO: 5            moltype = DNA   length = 20
FEATURE                 Location/Qualifiers
source                  1..20
                        mol_type = other DNA
                        organism = synthetic construct
SEQUENCE: 5
caactcacga actgatagtt                                                 20

SEQ ID NO: 6            moltype = DNA   length = 60
FEATURE                 Location/Qualifiers
source                  1..60
                        mol_type = other DNA
                        organism = synthetic construct
SEQUENCE: 6
tccggtgtgc ctctaaaatt caactcacga actgatagtt taaactgaag gcgggaaacg     60

SEQ ID NO: 7            moltype = DNA   length = 1348
FEATURE                 Location/Qualifiers
source                  1..1348
                        mol_type = other DNA
                        organism = synthetic construct
SEQUENCE: 7
tacaagaata ttgagacgtg agtacatagc attggcattt tcattagcaa gcatttcaaa     60
agaatttaat tttctcatag caatgtgata tctctcctca cgctcaattc tagttccttc    120
atgtagagca catatgtcca tccacaaatc atgacaattt ttatggtttc taactctatt    180
aaacacatct ttgcaaaggc ctctaaaaag ggtgttttg gccttagcat tccatttctc     240
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag ggggggttga attgggcttt tctaaaaatc aacactaact aaaatctaag    540
caagagccca acttcacccc gacaactagc actaagagaa taatactaga aatacaacaa    600
tgctaagata atacttcaaa tacttgctaa acaaatacac aatgtaaaat acttgaatta    660
agtgcggaat gtaaagcaag gtttagaaga ctcctccaat tttctagag gtatcaaaga     720
gtcggcactc tccccagtc ctcgttggag cacctgcgta agggtatcgc tctcccttgg     780
tcatcgcaag aaccaagtgc tcacaacgag atgatccttt gccactccgg cgcggtggat    840
cccctcacgac cgcttacaaa cttgagtcgg gtcaccaaca agatctccac ggtgatcacc   900
gagctcccaa cgccaccaag ccgtctaggt gatgccgatc accaagagta ataagccata    960
gactttcact tgaccaagag aagcctaatg catgcggtgt gtgctctagg tggctctcgc   1020
tagcgttaat gaggtccaaa tgcgggatta agattctcaa gtcacctcac taggctttgt   1080
ggtgcttgca atgctctacc aatgtgtagg agtaaatgtg ggcagcaaga ccatcaatat   1140
ggtaggtgga tgggtataa atagcccctca cccaccaact agccattacc aggaatctga   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacga                                       1348

SEQ ID NO: 8            moltype = DNA   length = 27
FEATURE                 Location/Qualifiers
source                  1..27
                        mol_type = other DNA
                        organism = synthetic construct
SEQUENCE: 8
tttcccgcct tcagttttaaa ctatcag                                        27

SEQ ID NO: 9            moltype = DNA   length = 27
FEATURE                 Location/Qualifiers
source                  1..27
                        mol_type = other DNA
                        organism = synthetic construct
SEQUENCE: 9
tttaaactat cagttcgtga gttgaat                                         27

SEQ ID NO: 10           moltype = DNA   length = 27
FEATURE                 Location/Qualifiers
source                  1..27
                        mol_type = other DNA
                        organism = synthetic construct
SEQUENCE: 10
tttagaggca caccggacag cgtatcg                                         27
```

```
SEQ ID NO: 11            moltype = DNA  length = 27
FEATURE                  Location/Qualifiers
source                   1..27
                         mol_type = other DNA
                         organism = synthetic construct
SEQUENCE: 11
tttaaactga aggcgggaaa cgacaat                                          27

SEQ ID NO: 12            moltype = DNA  length = 27
FEATURE                  Location/Qualifiers
source                   1..27
                         mol_type = other DNA
                         organism = synthetic construct
SEQUENCE: 12
tttccccgat cgttcaaaca tttggca                                          27

SEQ ID NO: 13            moltype = DNA  length = 27
FEATURE                  Location/Qualifiers
source                   1..27
                         mol_type = other DNA
                         organism = synthetic construct
SEQUENCE: 13
tttacaacaa gctgtaagag cttactg                                          27

SEQ ID NO: 14            moltype = DNA  length = 25
FEATURE                  Location/Qualifiers
source                   1..25
                         mol_type = other DNA
                         organism = synthetic construct
SEQUENCE: 14
tgctgcgcat gggcgcaccg gacag                                            25

SEQ ID NO: 15            moltype = DNA  length = 25
FEATURE                  Location/Qualifiers
source                   1..25
                         mol_type = other DNA
                         organism = synthetic construct
SEQUENCE: 15
caattcctgc agcgttgcgg ttctg                                            25

SEQ ID NO: 16            moltype = DNA  length = 1127
FEATURE                  Location/Qualifiers
source                   1..1127
                         mol_type = other DNA
                         organism = synthetic construct
SEQUENCE: 16
ctcacaacga gatgatcctt tgccactccg gcgcggtgga tccctcacga ccgcttacaa      60
acttgagtcg ggtcaccaac aagatctcca cggtgatcac cgagctccca acgccaccaa     120
gccgtctagg tgatgccgat caccaagagt aataagccat agactttcac ttgaccaaga     180
gaagcctaat gcatgcggtg tgtgctctag gtggctctcg ctagcgttaa tgaggtccaa     240
atgcgggatt aagattctca agtcacctca ctaggctttg tggtgcttgc aatgctctac     300
caatgtgtag gagtaaatgt gggcagcaag accatcaata tggtaggtgg atggggtata     360
aatagccctc acccaccaac tagccattac caggaatctg ctgcgcatgg gcgcaccgga     420
cagtccggtc tgccaccggt gcgccaacgg tcgactcaaa cggctagttc tgacagctag     480
ccgttggaca gatggcatac cggacagtcc gatacgctgt ccggtgtgcc tctaaaattc     540
aactcacgaa tttacaccac aatatacct cttcccttag tttaaactga aggcgggaaa     600
cgacaatctg atcatgagcg gagaattaag ggagtcacgt tatgaccccc gccgatgacg     660
cgggacaagc cgttttacgt ttggaactga cagaaccgca acgctgcagg aattggccgc     720
agctgccatt taaatcaatt gggcgcgccg aattcgagct cggtacaagc ttctggcaga     780
caaagtggca gacatactgt cccacaaatg aagatggaat ctgtaaaaga aaacgcgtga     840
aataatgcgt ctgacaaagg ttaggtcggt tgcctttaat caataccaaa gtggtcccta     900
ccacgatgga aaaactgtgc agtcggtttg ctttttctg acgaacaaat aagattcgtg     960
gccgacaggt gggggtccac catgtgaagg catcttcaga ctccaataat ggagcaatga    1020
cgtaagggct tacgaaataa gtaagggtag tttgggaaat gtccactcac ccgtcagtct    1080
ataaatactt agccctcc tcattgttaa gggagcaagg atccacc                   1127

SEQ ID NO: 17            moltype = DNA  length = 27
FEATURE                  Location/Qualifiers
source                   1..27
                         mol_type = other DNA
                         organism = synthetic construct
SEQUENCE: 17
tttacaccac aatatacct cttccct                                          27

SEQ ID NO: 18            moltype = DNA  length = 25
FEATURE                  Location/Qualifiers
source                   1..25
                         mol_type = other DNA
                         organism = synthetic construct
```

```
SEQUENCE: 18
aagcaaggtt tagaagactc ctcca                                           25

SEQ ID NO: 19           moltype = DNA  length = 25
FEATURE                 Location/Qualifiers
source                  1..25
                        mol_type = other DNA
                        organism = synthetic construct
SEQUENCE: 19
gggaagccca ccacgcccag caggt                                           25

SEQ ID NO: 20           moltype = DNA  length = 23
FEATURE                 Location/Qualifiers
source                  1..23
                        mol_type = other DNA
                        organism = synthetic construct
SEQUENCE: 20
caccacaata taccctcttc cct                                             23

SEQ ID NO: 21           moltype = DNA  length = 1399
FEATURE                 Location/Qualifiers
source                  1..1399
                        mol_type = other DNA
                        organism = synthetic construct
SEQUENCE: 21
aagcaaggtt tagaagactc ctccaatttt tctagaggta tcaaagagtc ggcactctcc     60
cctagtcctc gttggagcac ctgcgtaagg gtatcgctct cccttggtca tcgcaagaac    120
caagtgctca aacgagatg atcctttgcc actccggcgc ggtggatccc tcacgaccgc     180
ttacaaactt gagtcgggtc accaacaaga tctccacggt gatcaccgag ctcccaacgc    240
caccagccg tctaggtgat gccgatcacc aagagtaata agccatagac tttcacttga     300
ccaagagaag cctaatgcat gcggtgtgtg ctctaggtgg ctctcgctag cgttaatgag    360
gtccaaatgc gggattaaga ttctcaagtc acctcactag gctttgtggt gcttgcaatg    420
ctctaccaat gtgtaggagt aaatgtgggc agcaagacca tcaatatggt aggtggatgg    480
ggtataaata gccctcaccc accaactagc cattaccagg aatctgctgc gcatgggcgc    540
accggacagt ccggtgtgcc accggtgcgc caacggtcga ctcaaacggc tagttctgac    600
agctagccgt tggacagatg gcataccgga cagtccgata cgctgtccgg tgtgcctcta    660
aaattcaact cacgaattta caccacaata taccctcttc ccttagttta aactgaaggc    720
gggaaacgac aatctgatca tgagcggaga attaagggag tcacgttatg accccgccg     780
atgacgcgg acaagccgtt ttacgtttgg aactgacaga accgcaacgc tgcaggaatt     840
ggccgcagct gccatttaaa tcaattgggc gcgccgaatt cgagctcggt acaagcttct    900
ggcagacaaa gtggcagaca tactgtccca caaatgaaga gcaagatcgt aaaagaaaac    960
gcgtgaaata atgcgtctga caaaggttag gtcggctgcc tttaatcaat accaaagtgg   1020
tccctaccac gatggaaaaa ctgtgcagtc ggtttggctt tttctgacga acaaataaga   1080
ttcgtggccg acaggtgggg gtccaccatg tgaaggcatc ttcagactcc aataatgag    1140
caatgacgta agggcttacg aaataagtaa gggtagtttg gaaatgtcc actcacccgt    1200
cagtctataa atacttagcc cctccctcat tgttaaggga gcaaggatcc accatgacta   1260
gtaacggccg ccagtgtgct ggtattcgc cttatgacgg ccgacaacaa caccgaggcc    1320
tggacagcag caccaccaag gacgtgatcc agaagggcat cagcgtggtg ggcgacctgc   1380
tgggcgtggt gggcttccc                                                1399

SEQ ID NO: 22           moltype = DNA  length = 1396
FEATURE                 Location/Qualifiers
source                  1..1396
                        mol_type = other DNA
                        organism = synthetic construct
SEQUENCE: 22
aagcaaggtt tagaagactc ctccaatttt tctagaggta tcaaagagtc ggcactctcc     60
cctagtcctc gttggagcac ctgcgtaagg gtatcgctct cccttggtca tcgcaagaac    120
caagtgctca aacgagatg atcctttgcc actccggcgc ggtggatccc tcacgaccgc     180
ttacaaactt gagtcgggtc accaacaaga tctccacggt gatcaccgag ctcccaacgc    240
caccagccg tctaggtgat gccgatcacc aagagtaata agccatagac tttcacttga     300
ccaagagaag cctaatgcat gcggtgtgtg ctctaggtgg ctctcgctag cgttaatgag    360
gtccaaatgc gggattaaga ttctcaagtc acctcactag gctttgtggt gcttgcaatg    420
ctctaccaat gtgtaggagt aaatgtgggc agcaagacca tcaatatggt aggtggatgg    480
ggtataaata gccctcaccc accaactagc cattaccagg aatctgctgc gcatgggcgc    540
accggacagt ccggtgtgcc accggtgcgc caacggtcga ctcaaacggc tagttctgac    600
agctagccgt tggacagatg gcataccgga cagtccgata cgctgtccgg tgtgcctcta    660
aatttacacc acaatatacc ctcttcccct cacgaactga tagtttaaac tgaaggcggg    720
aaacgacaat ctgatcatga gcggagaatt aagggagtca cgttatgacc ccgccgatg    780
acgcgggaca agccgttta cgtttggaac tgacagaacc gcaacgctgc aggaattggc     840
cgcagctgcc atttaaatca attgggcgcg ccgaattcga gctcggtaca agcttctggc    900
agacaaagtg gcagacatac tgtcccacaa atgaagatcg taaaagaaaacg             960
tgaaataatg cgtctgacaa aggttaggtc ggctgccttt aatcaatacc aaagtggtcc   1020
ctaccacgat ggaaaaactg tgcagtcggt ttggcttttt ctgacgaaca aataagattc   1080
gtggccgaca ggtgggggtc caccatgtga aggcatcttc agactccaat aatgagcaa    1140
tgacgtaagg gcttacgaaa taagtaaggg tagtttggga aatgtccact cacccgtcag   1200
tctataaata cttagcccct ccctcattgt taagggagca aggatccacc atgactagta   1260
```

```
acggccgcca gtgtgctggt attcgccctt atgacggccg acaacaacac cgaggcctgg    1320
acagcagcac caccaaggac gtgatccaga aagggcatcag cgtggtgggc gacctgctgg   1380
gcgtggtggg cttccc                                                    1396

SEQ ID NO: 23         moltype = DNA  length = 25
FEATURE               Location/Qualifiers
source                1..25
                      mol_type = other DNA
                      organism = synthetic construct
SEQUENCE: 23
gagttcgtgc ccgccgaggt gacct                                          25

SEQ ID NO: 24         moltype = DNA  length = 25
FEATURE               Location/Qualifiers
source                1..25
                      mol_type = other DNA
                      organism = synthetic construct
SEQUENCE: 24
tgtccggtgc accctttgcc agtgg                                          25

SEQ ID NO: 25         moltype = DNA  length = 8858
FEATURE               Location/Qualifiers
source                1..8858
                      mol_type = other DNA
                      organism = synthetic construct
SEQUENCE: 25
tacaagaata ttgagacgtg agtacatagc attggcattt tcattagcaa gcatttcaaa    60
agaatttaat tttctcatag caatgtgata tctctcctca cgctcaattc tagttccttc    120
atgtagagca catatgtcca tccacaaatc atgacaattt ttatggtttc taactctatt   180
aaacacatct ttgcaaaggc ctctaaaaag ggtgttttg gcttagcat tccattctc      240
atagttcaac tcttcaccta caagatttgt gggatctcta ggttcgggga atctttgtgt   300
ggcggctttg tagacaccaa tgtctatagc ctctaaatat gcttccatac gaattttcca   360
atatggaaaa tcgtcaccat aaaaaacggg agaaggtcca tccccaccgg acatcgttac   420
tctagcggtt aagctaatct aagagcaaca aggctcttat accaattgaa aggatcacga    480
tgcccaagag gggggggttga attgggcttt tctaaaaatc aacactaact aaaatctaag   540
caagagccca acttcacccc gacaactagc actaagagaa taatactaga aatacaacaa   600
tgctaagata atacttcaaa tacttgctaa acaaatacac aatgtaaaat acttgaatta   660
agtgcggaat gtaaagcaag gtttagaaga ctcctccaat ttttctagag gtatcaaaga   720
gtcggcactc tccccctagtc ctcgttggaa cacctgcgta agggtatcgc tctccctttg   780
tcatcgcaag aaccaagtgc tcacaacgag atgatccttt gccactccgg cgcggtggat   840
ccctcacgac cgcttacaaa cttgagtcgg gtcaccaaca agatctccac ggtgatcacc   900
gagctcccaa cgccaccaag ccgtctaggt gatgccgatc accaagagta ataagccata   960
gactttcact tgaccaagag aagcctaatg catgcggtgt gtgctctagg tggctctcgc  1020
tagcgttaat gaggtccaaa tgcgggatta agattctcaa gtcacctcac taggctttgt  1080
ggtgcttgca atgctctacc aatgtgtagg agtaaatgtg ggcagcaaga ccatcaatat  1140
ggtaggtgga tgggggtataa atagccctca cccaccaact agccattacc aggaatctgc  1200
tgcgcatggg cgcaccggac agtccggtgt gccaccggtg cgccaacggt cgactcaaac  1260
ggctagttct gacagctagc cgttggacag atggcatacc ggacagtccg atacgctgtc  1320
cggtgtgcct ctaaaattca actcacgaat ttaaactgaa ggcgggaaac gacaatctga  1380
tcatgagcgg agaattaagg gagtcacgtt atgaccccg ccgatgacgc gggacaagcc    1440
gttttacgtt tggaactgac agaaccgcaa cgctgcagga attggccgca gctgccattt  1500
aaatcaattg ggcgcgccga attcgagctc ggtacaagct tctggcagac aaagtggcag  1560
acatactgtc ccacaaatga agatggaatc tgtaaaagaa aacgcgtgaa ataatgcgtc  1620
tgacaaaggt taggtcggct gcctttaatc aataccaaag tggtcccta cacgatgaa    1680
aaactgtgca gtcggtttgg ctttttctga cgaacaaata agattcgtgg ccgacaggtg  1740
ggggtccacc atgtgaaggg atcttcagac tccaataatg gagcaatgca gtaagggctt  1800
acgaaataag taagggtagt ttgggaaatg tccactcacc cgtcagtcta taaatactta  1860
gcccctccct cattgttaag ggagcaagga tccaccatga ctagtaacgg ccgccagtgt  1920
gctggtattc gcccttatga cggccgacaa caacaccgag gcctggacag cagcaccacc  1980
aaggacgtga tccagaaggg catcagcgtg gtgggcgacc tgctgggcgt ggtgggcttc  2040
cccttcggcg cgcccctggt gagcttctac accaacttcc tgaacaccat ctggcccagc  2100
gaggaccct ggaaggcctt catggagcag gtggaggccc tgatgaccca aagatcgcc    2160
gactacgcca gaacaaggc actggccgag ctacaggggc tccagaacaa cgtggaggac  2220
tatgtgagcg ccctgagcag ctggcagaag aaccccgctg caccgttccg caacccctca  2280
agccagggcc gcatccgcga gctgttcagc caggccgaga gccacttccg caacagcatg  2340
cccagcttcg ccatcagcgg ctacgaggtg ctgttcctga ccacctacgc ccaggccgcc  2400
aacaccccac tgttcctgct gaaggacgcc caaatctacg agaggagtg gggctacgag  2460
aaggaggaca tcgccgagtt ctacaagcgc agctgtgaagc tgaccagga gtacaccgac  2520
cactgctgga agtggtacaa cgtgggtcta gacaagctcc gcggcagcag ctacgagagc  2580
tgggtgaact tcaaccgcta ccgccgcgag atgaccctga ccgtgctgga cctgatcgcc  2640
ctgttccccc tgtacgacgt cgcgcctac cccaaggagg tgaagaccga gctgaccgc   2700
gacgtgctga ccgaccccat cgtgggcgtg aacaacctgc gcggctacgg caccaccttc  2760
agcaacatcg agaactacat ccgcaagccc caccgtgttcg actacctgca ccgcatcag  2820
ttccacacgc gtttcgacgc cggctactac gcttcaacta ctggagccgc                2880
aactacgtga gcaccgccc cagcatcggc agcaacgaca tcatcaccag ccccttctac  2940
ggcaacaaga gcagcagcc cgtgcagaac cttgagttca acggcgagaa ggtgtaccgc  3000
gccgtggcta caccaacct ggccgtgtgg ccctctgcag tgtacagcgg cgtgaccaag  3060
gtggagttca ccagtacaa cgaccagacc gacgaggcca gcacccagac ctacgacagc  3120
aagcgcaacg tgggcgccgt gagctgggac agcatcgacc agctgcccccc cgagaccacc  3180
```

```
gacgagcccc tggagaaggg ctacagccac cagctgaact acgtgatgtg cttcctgatg   3240
cagggcagcc gcggcaccat ccccgtgctg acctggaccc acaagagcgt cgacttcttc   3300
aacatgatcg acagcaagaa gatcacccag ctgcccctga ccaagagcac caacctgggc   3360
agcggcacca gcgtggtgaa gggccccggc ttcaccggcg cgacatcct gcgccgcacc    3420
agcccggcc agatcagcac cctgcgcgtg aacatcacca cccccctgg ccagcgctac    3480
cgcgtccgca tccgctacgc cagcaccacc aacctgcagt tccacaccag catcgacggc   3540
cgccccatca accagggcaa cttcagcgcc accatgagca gcggcagcaa cctgcagagc   3600
ggcagcttcc gcaccgtggg cttcaccacc cccttcaact tcagcaacgg cagcagcgtg   3660
ttcaccctga gcgcccacgt gttcaacagc ggcaacgagg tgtacatcga ccgcatcgag   3720
ttcgtgcccg ccgaggtgac cttcgaggcc gagtacgacc tggagaggc tcagaaggcc    3780
gtgaacgagc tgttcaccag cagcaaccag atcggcctga agaccgacgt gaccgactac   3840
cacatcgatc aggtgtagga gctgagctct agatccccga atttccccga tcgttcaaac   3900
atttggcaat aaagtttctt aagattgaat cctgttgccg tcttgcgat gattatcata    3960
taatttctgt tgaattacgt taagcatgta ataattaaca tgtaatgcat gacgttattt   4020
atgagatggg ttttttatgat tagagtcccg caattataca tttaatacgc gatagaaaac   4080
aaaatatagc gcgcaaacta ggataaatta tcgcgcgcgg tgtcatctat gttactagat   4140
cgggaattgg gtaccagctt gcatgcctgc agtgcagcgt gacccggtcg tgcccctctc   4200
tagagataat gagcattgca tgtctaagtt ataaaaaatt accacatatt ttttttgtca    4260
cacttgtttg aagtgcagtt tatctatctt tatacatata tttaaacttt actctacgaa   4320
taatataatc tatagtacta caataatatc agtgttttag agaatcatat aaatgaacag   4380
ttagacatgg tctaaaggac aattgagtat tttgacaaca ggactctaca gttttatctt   4440
tttagtgtgc atgtgttctc ctttttttt gcaaatagct tcacctatat aatacttcat    4500
ccattttatt agtacatcca tttagggttt agggttaatg gttttatag actaattttt    4560
ttagtacatc tatttttattc tattttagcc tctaaattaa gaaaactaaa actctatttt   4620
agtttttta tttaataatt tagatataaa atagaataaa ataagtgac taaaaattaa    4680
acaaataccc tttaagaaat taaaaaaact aaggaaaat ttttcttgtt tcgagtagat    4740
aatgccagcc tgttaaacgc cgtcgacgag tctaacggac accaaccagc gaaccagcag   4800
cgtcgcgtcg ggcaagcga agcagacggc acggcatctc tgtcgctgcc tctgaccccc    4860
tctcgagagt tccgctccac cgttggactt gctccgctgt cggcatccag aaattgcgtg   4920
gcggagcgg agacgtgagc cggcacggca ggcggcctcc tcctcctctc acggcaccgg   4980
cagctacggg ggattccttt cccaccgctc cttcgctttc ccttcctcgc cgccgtaat    5040
aaatagacac cccctccaca ccctctttcc ccaacctcgt gttgttcgga gcgcacacac   5100
acacaaccag atctccccca aatccacccg tcggcacctc cgcttcaagg tacgccgctc   5160
gtcctcccc cccccctc tctaccttct ctagatcggc gttccggtcc atggttaggg    5220
cccggtagtt ctacttctgt tcatgtttgt gttagatccg tgtttgtgtt agatccgttg   5280
tgctagcgtt cgtacacgga tgcgacctgt acgtcagaca cgttctgatt gctaacttgc   5340
cagtgttcc ctttgggaa tcctgggatg gctctagccg ttccgcagac gggatcgatt    5400
tcatgatttt tttttgtttcg ttgcataggg tttggtttgc cctttttcctt tatttcaata   5460
tatgccgtgc acttgtttgt cgggtcatct tttcatgctt tttttttgtct tggttgtgat   5520
gatgtggtct ggttgggcgg tcgttctaga tcggagtaga attctgtttc aaactacctg   5580
gtggatttat taattttgga tctgtatgtg tgtgccatac atattcatag ttacgaattg   5640
aagatgatgg atgaaatat cgatctagga taggtataca tgttgatgcg ggttttactg    5700
atgcatatac agagatgctt tttgttcgct tggttgtgat gatgtggtgt ggttgggcgg   5760
tcgttcattc gttctagatc ggagtagaat actgtttcaa actacctggt gtatttatta   5820
attttggaac tgtatgtgtg tgtcatacat cttcatagtt acgagtttaa gatggatgga   5880
aatatcgatc taggataggt atacatgttg atgtgggttt tactgatgca tatacatgat   5940
ggcatatgca gcatctattc atatgctcta accttgacta cctatctatt ataataaaca   6000
agtatgtttt ataattattt tgatcttgat atacttggat gatggcatat gcagcagcta   6060
tatgtggatt tttttagccc tgccttcata cgctatttat ttgcttggta ctgtttcttt   6120
tgtcgatgct caccctgttg tttggtgtta cttctgcagg gatccccgat catgcaaaaa   6180
ctcattaact cagtgcaaaa ctatgcctgg ggcagcaaaa cggcgttgac tgaactttat   6240
ggtatgaaa atccgtccag ccagccgatg gccgagctgt ggatgggcgc acatccgaaa   6300
agcagttcac gagtgcagaa tgccgccgga gatatcgttt cactgcgtga tgtgattgag   6360
agtgataaat cgactctgct cggagaggcc gttgccaaac gctttggcga actgcctttc   6420
ctgttcaaag tattatgcgc agcacagcca ctctccattc aggttcatcc aaacaaacac    6480
aattctgaaa tcggttttgc caaagaaaat gccgcaggta tcccgatgga tgccgccgaa   6540
cgtaactata aagatcctaa ccacaagccg gagctggttt ttgcgctgac gccttttctt   6600
gcgatgaacg cgtttcgtga attttccgag attgtctccc tactccagcc ggtcgcaggt   6660
gcacatccgg cgattgctca ctttttacaa cagcctgatg ccgaacgttt aagcgaactg   6720
ttcgccagcc tgttgaatat gcagggtgaa gaaaaatccc gcgcgctggc gattttaaaa   6780
tcggccctcg atagccagca gggtgaaccg tggcaaacga ttcgtttaat ttctgaatt    6840
tacccggaag acagcggtct gttctccccg ctattgctga atgtggtgaa attgaaccct   6900
ggcgaagcga tgttcctgtt cgctgaaaca ccgcacgctt acctgcaagg cgtggcgctg   6960
gaagtgatgg caaactccga taacgtgctg cgtgcggtc tgacgcctaa atacattgat   7020
attccggaac tggttgccaa tgtgaaattc gaagccaaac cggctaacca gttgttgacc   7080
cagccggtga aacaaggtgc agaactggac ttcccgattc cagtggatga ttttgccttc   7140
tcgctgcatg accttagtga taaagaaacc accattagcc agcagagtgc cgccattttg   7200
ttctgcgtcg aaggcgatgc aacgttgtgg aaaggttctc agcagttaca gcttaaaccg   7260
ggtgaatcag cgtttattgc cgccaacgaa tcaccggtga ctgtcaaagg ccacggccgt   7320
ttagcgcgtg tttacaacaa gctgtaagag cttactgaaa aaattaacat ctcttgctaa   7380
gctgggagct cgatccgtcg acctgcagat cgttcaaaca tttggcaata aagtttctta   7440
agattgaatc ctgttgccgg tcttgcgatg attatcatat aatttctgtt gaattacgtt   7500
aagcatgtaa taattaacat gtaatgcatg acgttattta tgagatgggt ttttatgatt   7560
agagtcccgc aattatacat ttaatacgcg atagaaaaca aaatatagcg cgcaaactag   7620
gataaattat cgcgcgcggt gtcatctatg ttactagatc tgctagccct gcaggaaatt   7680
taccggtgcc cgggcggcca gcatggccgt atccgcaatg tgttattaag ttgtctaagc   7740
gtcaatttgt ttacaccaca atatacccto ttccctgggc caggctgggc ccactggcaa   7800
agggtgcacc ggacagtccg gtgccccaaa gccagaaacc ctagcttctg tttttgtgctg   7860
ttttttcaat ttggtttttg ttctaacttg tgagtatgtt ctagagttac acctagcact   7920
```

```
atatgtgagt gtgaatatgc accaacacta cactagaact cttttggtca aactacttat 7980
cgacaacccc tctttatagt acggctaaaa caaaataaaa gacctaacta tatcacgagt 8040
gtccgcaact ccttgacact cggaatacga agaccttcac ttttttgttc gtcgctttag 8100
ccgttgcttc aagtttttat ctccgggatt gttttcacca ttgtagtaca tctacctgta 8160
atgcgaccta acttaccatt tgcctctgca aaacacatgt tagtcacata taaaattacg 8220
ttgtcattaa tcactaaaac caaccagggg cctagatgct ttctagttta aatccccaac 8280
aagtcaaaat tctttctatt ttttttttgca agttccaatt gacatctgaa aggttgtaag 8340
gtacacgttt ggctctcatt gataacgggg gaaagataca gtgcaaacca ccatataatg 8400
acccacttct aatcgaatgg acctgtaacg acgaaataec ctgtgagaac tatggtttcac 8460
tcatgttaat tcattgaaat tgttgtagtg aattgacatg gttgggagcc tgcttagaga 8520
gtatagattg tcactttttt ttggaccgca acttattttt aaaagatatt gcgatcgctt 8580
gtttagtagc tgtttcaggc cccaatgcag tttctatcgt gatccattta agtcactcaa 8640
cattctcata cttctcattt tgcattaatt cattccaatc tccactacta taaaactacta 8700
gcttcgatgg tcgtcatacg ccatgcacga agcatgtaga tcaatccgca taccagtggg 8760
catctataga taggctgtga aaaccaccca aatccctact agtggacatt ttatctatag 8820
atggaccgtg agaaaccaca caagtctaac acgacagg 8858

SEQ ID NO: 26          moltype = DNA   length = 1541
FEATURE                Location/Qualifiers
source                 1..1541
                       mol_type = other DNA
                       organism = synthetic construct
SEQUENCE: 26
tacaagaata ttgagacgtg agtcatagc attggcattt tcattagcaa gcatttcaaa 60
agaatttaat tttctcatag caatgtgata tctctcctca cgctcaattc tagttccttc 120
atgtagagca catatgtcca tccacaaatc atgacaattt ttatggtttc taactctatt 180
aaacacatct ttgcaaaggc ctctaaaaag ggtgtttttg gccttagcat tccatttctc 240
atagttcaac tcttcaccta caagatttgt gggatctcta ggttcgggga atctttgtgt 300
ggcggctttg tagacaccaa tgtctatagc ctctaaatat gcttccatac gaattttcca 360
atatggaaaa tcgtcaccat aaaaaacggg agaaggtcca tccccaccgg acatcgttac 420
tctagcggtt aagctaatct aagagcaaca aggctcttat accaattgaa aggatcacga 480
tgcccaagag ggggggttga attgggcttt tctaaaaatc aacactaact aaaatctaag 540
caagagccca acttcacccc gacaactagc actaagagaa taatactaga aatacaacaa 600
tgctaagata atacttcaaa tacttgctaa acaaatacac aatgtaaaat acttgaatta 660
agtgcggaat gtaaagcaag gtttagaaga ctcctccaat ttttctagag gtatcaaaga 720
gtcggcactc tcccctagtc ctcgttggag cacctgcgta agggtatcgc tctcccttgg 780
tcatcgcaag aaccaagtgc tcacaacgag atgatccttt gccactccgg cgcggtggat 840
ccctcacgac cgcttacaaa cttgagtcgg gtcaccaaca agatctccac ggtgatcacc 900
gagctcccaa cgccaccaag ccgtctaggt gatgccgatc accaagagta ataagccata 960
gactttcact tgaccaagag aagcctaatg catgcggtgt gtgctctagg tggctctcgc 1020
tagcgttaat gaggtccaaa tgcgggatta agattctcaa gtcacctcac taggctttgt 1080
ggtgcttgca atgctctacc aatgtgtagg agtaaatgtg ggcagcaaga ccatcaatat 1140
ggtaggtgga tggggtataa atagccctca cccaccaact agccattacc aggaatctgc 1200
tgcgcatggg cgcaccggac agtccggtgt gccaccggtg cgccaacggt cgactcaaac 1260
ggctagttct gacagctagc cgttggacag atggcatacc ggacagtccg atacgctgtc 1320
cggtgtgcct ctaaaattca actcacgaat ttaaactgaa ggcgggaaac gacaatctga 1380
tcatgagcgg agaattaagg gagtcacgtt atgacccccg ccgatgacgc gggacaagcc 1440
gttttacgtt tggaactgac agaaccgcaa cgctgcagga attggccgca gctgccattt 1500
aaatcaattg ggcgcgccga attcgagctc ggtacaagct t 1541

SEQ ID NO: 27          moltype = DNA   length = 8857
FEATURE                Location/Qualifiers
source                 1..8857
                       mol_type = other DNA
                       organism = synthetic construct
SEQUENCE: 27
tacaagaata ttgagacgtg agtcatagc attggcattt tcattagcaa gcatttcaaa 60
agaatttaat tttctcatag caatgtgata tctctcctca cgctcaattc tagttccttc 120
atgtagagca catatgtcca tccacaaatc atgacaattt ttatggtttc taactctatt 180
aaacacatct ttgcaaaggc ctctaaaaag ggtgtttttg gccttagcat tccatttctc 240
atagttcaac tcttcaccta caagatttgt gggatctcta ggttcgggga atctttgtgt 300
ggcggctttg tagacaccaa tgtctatagc ctctaaatat gcttccatac gaattttcca 360
atatggaaaa tcgtcaccat aaaaaacggg agaaggtcca tccccaccgg acatcgttac 420
tctagcggtt aagctaatct aagagcaaca aggctcttat accaattgaa aggatcacga 480
tgcccaagag ggggggttga attgggcttt tctaaaaatc aacactaact aaaatctaag 540
caagagccca acttcacccc gacaactagc actaagagaa taatactaga aatacaacaa 600
tgctaagata atacttcaaa tacttgctaa acaaatacac aatgtaaaat acttgaatta 660
agtgcggaat gtaaagcaag gtttagaaga ctcctccaat ttttctagag gtatcaaaga 720
gtcggcactc tcccctagtc ctcgttggag cacctgcgta agggtatcgc tctcccttgg 780
tcatcgcaag aaccaagtgc tcacaacgag atgatccttt gccactccgg cgcggtggat 840
ccctcacgac cgcttacaaa cttgagtcgg gtcaccaaca agatctccac ggtgatcacc 900
gagctcccaa cgccaccaag ccgtctaggt gatgccgatc accaagagta ataagccata 960
gactttcact tgaccaagag aagcctaatg catgcggtgt gtgctctagg tggctctcgc 1020
tagcgttaat gaggtccaaa tgcgggatta agattctcaa gtcacctcac taggctttgt 1080
ggtgcttgca atgctctacc aatgtgtagg agtaaatgtg ggcagcaaga ccatcaatat 1140
ggtaggtgga tggggtataa atagccctca cccaccaact agccattacc aggaatctgc 1200
tgcgcatggg cgcaccggac agtccggtgt gccaccggtg cgccaacggt cgactcaaac 1260
ggctagttct gacagctagc cgttggacag atggcatacc ggacagtccg atacgctgtc 1320
cggtgtgcct ctaaacacga actgatagtt taaactgaag gcgggaaacg acaatctgat 1380
```

```
catgagcgga gaattaaggg agtcacgtta tgacccccgc cgatgacgcg ggacaagccg    1440
ttttacgttt ggaactgaca gaaccgcaac gctgcaggaa ttggccgcag ctgccattta    1500
aatcaattgg gcgcgccgaa ttcgagctcg gtacaagctt ctggcagaca aagtggcaga    1560
catactgtcc cacaaatgaa gatggaatct gtaaaagaaa acgcgtgaaa taatgcgtct    1620
gacaaaggtt aggtcggctg cctttaatca ataccaaagt ggtccctacc acgatggaaa    1680
aactgtgcag tcggtttggc ttttttctgac gaacaaataa gattcgtggc cgacaggtgg    1740
gggtccacca tgtgaaggca tcttcagact ccaataatgg agcaatgacg taagggctta    1800
cgaaataagt aagggtagtt tgggaaatgt ccactcaccc gtcagtctat aaatacttag    1860
cccctccctc attgttaagg gagcaaggat ccaccatgac tagtaacggc cgccagtgtg    1920
ctggtattcg ccccttatgac ggccgcaaac aacaccgagg cctggacagc agcaccaca    1980
aggacgtgat ccagaagggc atcagcgtgg tgggcgacct gctgggcgtg gtgggcttcc    2040
ccttcggcgg cgccctggtg agcttctaca ccaacttcct gaacaccatc tggcccagcg    2100
aggacccctg gaaggccttc atggagcagg tggaggccct gatggaccag aagatcgccg    2160
actacgccaa gaacaaggca ctggccgagc tacagggcct ccagaacaac gtggaggact    2220
atgtgagcgc cctgagcagc tggcagaaga cccgctgc accgttccgc aacccccaca    2280
gccagggccg catccgcgag ctgttcagcc aggccgagag ccacttccgc aacagcatgc    2340
ccagcttcgc catcagcggc tacgaggtgc tgttcctgac cacctacgcc caggccgcca    2400
acacccacct gttcctgctg aaggacgccc aaatctacgg agaggagtgg ggctacgaga    2460
aggaggacat cgccgagttc tacaagcgcc agctgaagct gacccaggag tacaccgacc    2520
actgcgtgaa gtggtacaac gtgggtctag acaagctccg cggcagcagc tacgagagct    2580
gggtgaactt caaccgctac cgccgcgaga tgaccctgac cgtgctggac ctgatcgccc    2640
tgttcccccct gtacgacgtg cgcctgtacc ccaaggaggt gaagaccgag ctgaccgcg    2700
acgtgctgac cgaccccatc gtgggcgtga acaacctgcg cggctacggc accaccttca    2760
gcaacatcga gaactacatc cgcaagcccc acctgttcga ctacctgcac cgcatccagt    2820
ccacacgcg tttccagccc ggctactacg caacgacag cttcaactac tggagcggca    2880
actacgtgag caccgcccc agcatcggca gcaagcacat catcaccagc cccttctacg    2940
gcaacaagag cagcgagccc gtgcagaacc ttgagttcaa cggcgagaag gtgtaccacc    3000
ccgtggctaa caccaacctg gccgtgtggc cctctgcagt gtacagcggc gtgaccaagg    3060
tggagttcag ccagtacaac gaccagaccg acgaggccag cacccagacc tacgacagca    3120
agcgcaacgt gggcgccgtg agctgggaca gcatcgacca gctgccccc gagaccaccg    3180
acgagcccct ggagaagggc tacagccacc agctgaacta cgtgatgtgc ttcctgatgc    3240
agggcagccg cggccacatc cccgtgctga cctggaccca aagagcgtc gacttcttca    3300
acatgatcga cagcaagaag atcacccagc tgccctgac caagagcacc aacctgggca    3360
gcggcaccag cgtggtgaag ggccccggct tcaccggcgg cgacatcctg cgccgccaca    3420
gccccggcca gatcagcacc ctgcgcgtga acatcaccgc ccccctgagc cagcgctacc    3480
gcgtccgcat ccgctacgcc agcaccacca acctgcagtt ccacaccagc atcgacggcc    3540
gccccatcaa ccagggcaac ttcagcgcca ccatgagcag cggcagcaac ctgcagagcg    3600
gcagcttccg caccgtgggc ttcaccaccc ccttcaactt cagcaacggc agcagcgtgt    3660
tcacccctgag cgccccacgtg ttcaacagcg gcaacgaggt gtacatcgac cgcatcgagt    3720
tcgtgcccgc cgaggtgacc ttcgaggccg agtacgacct ggagagggct cagaaggccg    3780
tgaacgagct gttcaccagc agcaaccaga tcggcctgaa gaccgacgtg accgactacc    3840
acatcgatca ggtgtaggag ctgagctcta gatccccgaa tttccccgat cgttcaaaca    3900
tttggcaata aagtttctta agattgaatc ctgttgccgg tcttgcgatg attatcatat    3960
aatttctgtt gaattacgtt aagcatgtaa taattaacat gtaatgcatg acgttattta    4020
tgagatgggt tttttatgatt agagtcccgc aattatacat ttaatacgcg atagaaaaca    4080
aaatatagcg cgcaaactag gataaattat cgcgcgcggt gtcatctatg ttactagatc    4140
gggaattggg taccagcttg catgcctgca gtgcagcgtg acccggtcgt gcccctctct    4200
agagataatg agcattgcat gtctaagtta taaaaaatta ccacatattt ttttttgtcac    4260
acttgtttga agtgcagttt atctatcttt atacatatat ttaaacttta ctctacgaat    4320
aatataatct atagtactac aataaatatca gtgttttaga gaatcatata aatgaacagt    4380
tagacatggt ctaaaggaca attgagtatt ttgacaacag gactctacag ttttatcttt    4440
ttagtgtgca tgtgttctcc tttttttttg caaatagctt cacctatata atacttcatc    4500
cattttatta gtacatccat ttagggttta gggttaatgg ttttttataga ctaatttttt    4560
tagtacatct attttattct attttagcct ctaaattaag aaaactaaaa ctctattta    4620
gtttttttat ttaataattt agatataaaa tagaataaaa taaagtgact aaaaattaaa    4680
caaatacccct ttaagaaatt aaaaaaacta aggaaacatt tttcttgttt cgagtagata    4740
atgccagcct gttaaacgcc gtcgacgagt taacggacca ccaaccagcg aaccagcagc    4800
gtcgcgtcgg gccaagcgaa gcagacggca cggcatctct gtcgctgcct ctggacccct    4860
ctcgagagtt ccgctccacc gttggacttg ctccgctgtc ggcatccaga aattgcgtgg    4920
cggagcggca gacgtgagcc ggcacggcag gcggcctcct cctcctctca cggcaccggc    4980
agctacgggg gattccttc ccaccgctcc ttcgctttcc cttcctcgcc cgccgtaata    5040
aatagacacc ccctccacac cctctttccc caacctcgtg ttgttcggag cgcacacaca    5100
cacaaccaga tctcccccaa atccaccccgt cggcacctcc gcttcaaggt acgccgctcg    5160
tcctccccgc cccccccctct ccacttctc tagatcggcg ttccgtcca tggttagggc    5220
ccggtagttc tacttctgtt catgtttgtg ttagatccgt gtttgtgtta gatccgtgct    5280
gctagcgttc gtacacggat gcgacctgta cgtcagacac gttctgattg ctaacttgcc    5340
agtgtttctc tttggggaat cctgggatgg ctctagccgt tccgcagacg ggatcgattt    5400
catgattttt ttttgtttcgt tgcataggtt ttggtttgcc cttttcctttt atttcaatat    5460
atgccgtgca cttgttgtc gggtcatctt ttcatgctt tttttgtctt ggttgtgatg    5520
atgtggtctg gttgggcggt cgttctagat cggagtagaa ttctgtttca aactacctgg    5580
tggatttatt aattttggat ctgtatgtgt gtgccataca tattcatagt tacgaattga    5640
agatgatgga tggaaaatatc gatctaggat aggtatacat gttgatgcgg gtttactga    5700
tgcatataca gagatgcttt ttgttcgctt ggttgtgatg atgtggtgtg gtggggcggt    5760
cgttcattcg ttctagatcg gagtagaata ctgtttcaaa ctacctggtg tattattaa    5820
ttttggaact gtatgtgtgt gtcatacatc ttcatagtta cgagtttaag atggatgaa    5880
atatcgatct aggataggta tacatgttga tgggtttt actgatgcat atacatgatg    5940
gcatatgcag catctattca tatgctctaa ccttgagtac ctatctatta taataaacaa    6000
gtatgtttta taattatttt gatcttgata tacttggatg atggcatatg cagcagctat    6060
atgtggatt ttttagccct gccttcatac gctatttatt gcttggtac tgtttctttt    6120
```

```
gtcgatgctc accctgttgt ttggtgttac ttctgcaggg atccccgatc atgcaaaaac   6180
tcattaactc agtgcaaaac tatgcctggg gcagcaaaac ggcgttgact gaactttatg   6240
gtatggaaaa tccgtccagc cagccgatgg ccgagctgtg gatgggcgca catccgaaaa   6300
gcagttcacg agtgcagaat gccgccgag  atatcgtttc actgcgtgat gtgattgaga   6360
gtgataaatc gactctgctc ggagaggccg ttgccaaacg ctttggcgaa ctgcctttcc   6420
tgttcaaagt attatgcgca gcacagccac tctccattca ggttcatcca aacaaacaca   6480
attctgaaat cggttttgcc aaagaaaatg ccgcaggtat cccgatggat gccgccgagc   6540
gtaactataa agatcctaac cacaagccgg agctggtttt tgcgctgacg cctttccttg   6600
cgatgaacgc gtttcgtgaa ttttccgaga ttgtctccct actccagccg gtcgcaggtg   6660
cacatccggc gattgctcac tttttacaac agcctgatgc cgaacgttta agcgaactgt   6720
tcgccagcct gttgaatatg cagggtgaag aaaaatcccg cgcctggcg  attttaaaat   6780
cggccctcga tagccagcag ggtgaaccgt ggcaaacgat tcgtttaatt tctgaatttt   6840
acccggaaga cagcggtctg ttctcccgc  tattgctgaa tgtggtgaaa ttgaaccctg   6900
gcgaagcgat gttcctgttc gctgaaacac cgcacgctta cctgcaaggc gtggcgctgg   6960
aagtgatggc aaactccgat aacgtgctgc gtgcgggtct gacgcctaaa tacattgata   7020
ttccggaact ggttgccaat gtgaaattcg aagccaaacc ggctaaccag ttgttgaccc   7080
agccggtgaa acaaggtgca gaactggact tcccgattcc agtggatgat tttgccttct   7140
cgctgcatga ccttagtgat aaagaaacca ccattagcca gcagagtgcc gccattttgt   7200
tctgcgtcga aggcgatgca acgttgtgga aaggttctca gcagttacag cttaaaccgg   7260
gtgaatcagc gtttattgcc gccaacgaat caccggtgac tgtcaaaggc cacggccgtt   7320
tagcgcgtgt ttacaacaag ctgtaagagc ttactgaaaa aattaacatc tcttgctaag   7380
ctgggagctc gatccgtcga cctgcagatc gttcaaacat ttggcaataa agtttcttaa   7440
gattgaatcc tgttgccggt cttgcgatga ttatcatata atttctgttg aattacgtta   7500
agcatgtaat aattaacatg taatgcatga cgttatttat gagatggtt  tttatgatta   7560
gagtcccgca attatacatt taatacgcga tagaaaacaa aatatagcgc gcaaactagg   7620
ataaattatc gcgcgcggtg tcatctatgt tactagatct gctagccctg caggaaattt   7680
accggtgccc gggcggccag catgccgta  tccgcaatgt gttattaagt tgtctaagcg   7740
tcaatttgtt tacaccacaa tatccctct  tccctgggcc aggctgggcc cactggcaaa   7800
gggtgcaccg gacagtccgg tgccccaaag ccagaaaccc tagcttctgt tttgtgctgt   7860
ttttcaatt  tggtttttgt tctaacttgt gagtatgttc tagagttaca cctagcacta   7920
tatgtgagtg tgaatatgca ccaacactac actagaactc ttttggtcaa actacttatc   7980
gacaacccct ctttatagta cggctaaaac aaaataaaag acctaactat atcacgagtg   8040
tccgcaactc cttgacactc ggaatacgaa gaccttcact ttttgtttcg tcgctttagc   8100
cgttgcttca agtttttatc tccgggattg ttttccaccat tgtagtacat ctacctgtaa   8160
tgcgacctaa cttaccatttt gcctctgcaa aacacatgt  agtcacatat aaaattacgt   8220
tgtcattaat cactaaaacc aaccagggc  ctagatgctt tctagtttaa atccccaaca   8280
agtcaaaatt ctttctattt ttttttgcaa gttccaattg acatctgaaa ggttgtaagg   8340
tacacgtttg gctctcattg ataacggggg aaagatacag tgcaaaccac catataatga   8400
cccacttcta atcgaatgga cctgtaacga cgaaatacct tgtgagaact atggttcact   8460
catgttaatt cattgaaatt gttgtagtga attgacatgg ttgggagcct gcttagagag   8520
tatagattgt cactttttt  tggaccgcaa cttatttttta aaagatattg cgatcgcttg   8580
tttagtagct gtttcaggcc ccaatgcagt ttcatcgtg  atcccattta agtcactcaac   8640
attctcatac ttctcatttt gcattaattc attccaatct ccactactat aaaatactag   8700
cttcgatggt cgtcatacgc catgcacgaa gcatgtagat caatccgcat accagtgggc   8760
atctatagat aggctgtgaa aaccacccaa atccctacta gtggacattt tatctataga   8820
tggaccgtga gaaaccacac aagtctaaca cgacagg                            8857
```

| SEQ ID NO: 28 | moltype = DNA  length = 1540 |
|---|---|
| FEATURE | Location/Qualifiers |
| source | 1..1540 |
|  | mol_type = other DNA |
|  | organism = synthetic construct |

SEQUENCE: 28
```
tacaagaata ttgagacgtg agtacatagc attggcattt tcattagcaa gcatttcaaa     60
agaattttaat tttctcatag caatgtgata tctctcctca cgctcaattc tagttccttc    120
atgtagagca catatgtcca tccacaaatc atgacaattt ttatggtttc taactctatt    180
aaacacatct ttgcaaaggc ctctaaaaag ggtgtttttg gccttagcat tccatttctc    240
atagttcaac tcttcaccta caagatttgt gggatctcta ggttcgggga tctttgtgtt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag ggggggttga attgggcttt tctaaaaatc aacactaact aaaatctaag    540
caagagccca acttcaccc  gacaactagc actaagagaa taatactaga aatcaacaa    600
tgctaagata atacttcaaa tacttgctaa acaaatacac aatgtaaaat acttgaatta    660
agtgcggaat gtaaagcaag gtttagaaga ctcctccaat ttttctagag gtatcaaaga    720
gtcggcactc tcccctagtc ctcgttggag cacctgcgta agggtatcgc tctcccttgg    780
tcatcgcaag aaccaagtgc tcacaacgag atgatccttt gccactccgg cgcggtggat    840
ccctcacgac cgcttacaaa cttgagtcgg gtcaccaaca agatctccac ggtgatcacc    900
gagctcccaa cgccaccaag ccgtcctaggt gatgccgatc accaagagta ataagccatt    960
gactttcact tgaccaagag aagcctaatg catgcggtgt gtgctctagg tggctctcgc   1020
tagcgttaat gaggtccaaa tcgggattga agattctcaa gtcacctcac taggctttgt   1080
ggtgcttgca atgctctacc aatgtgtagg agtaaatgtg ggcagcaaga ccatcaatat   1140
ggtaggtgga tggggtataa atagccctca cccaccaact agccattacc aggaatctgc   1200
tgcgcatggg cgcaccggac acccggtgt  gccacggtg  cgccaacggt cgactcaaac   1260
ggctagttct gacagctagc cgttggacag atggcatacc ggacagtccg atacgctgtc   1320
cggtgtgcct ctaaacacga actgatagtt taaactgaag gcgggaaacg acaatctgat   1380
catgagcgga gaattaaggg agtcacgtta tgaccccgc  cgatgacgcg ggacaagccg   1440
ttttacgttt ggaactgaca gaaccgcaac gctgcaggaa ttggccgcag ctgccattta   1500
aatcaattgg gcgcgccgaa ttcgagctcg gtacaagctt                         1540
```

| SEQ ID NO: 29 | moltype = DNA   length = 8888 |
|---|---|
| FEATURE | Location/Qualifiers |
| source | 1..8888 |
| | mol_type = other DNA |
| | organism = synthetic construct |

SEQUENCE: 29

```
tacaagaata ttgagacgtg agtacatagc attggcattt tcattagcaa gcatttcaaa    60
agaatttaat tttctcatag caatgtgata tctctcctca cgctcaattc tagttccttc   120
atgtagagca catatgtcca tccacaaatc atgacaattt ttatggtttc taactctatt   180
aaacacatct ttgcaaaggc ctctaaaaag ggtgttttg gccttagcat tccatttctc    240
atagttcaac tcttcaccta caagatttgt gggatctcta ggttcgggga atctttgtgt   300
ggcggctttg tagacaccaa tgtctatagc ctctaaaatat gcttccatac gaattttcca   360
atatggaaaa tcgtcaccat aaaaaacggg agaaggtcca tccccaccgg acatcgttac   420
tctagcggtt aagctaatct aagagcaaca aggctcttat accaattgaa aggatcacga   480
tgcccaagag gggggttga attgggcttt tctaaaaatc aacactaact aaaatctaag    540
caagagccca acttcacccc gacaactagc actaagagaa taatactaga aatcaacaa    600
tgctaagata atacttcaaa tacttgctaa acaaatacac aatgtaaaat acttgaatta   660
agtgcggaat gtaaagcaag gtttagaaga ctcctccaat ttttctagag gtatcaaaga   720
gtcggcactc tccccagtc ctcgttggag cacctgcgta agggtatcgc tctcccttgg    780
tcatcgcaag aaccaagtgc tcacaacgag atgatccttt gccactccgg cgcggtggat   840
ccctcacgac cgcttacaaa cttgagtcgg gtcaccaaca agatctccac ggtgatcacc   900
gagctcccaa cgccaccaag ccgtctaggt gatgccgatc accaagagta ataagccata   960
gactttcact tgaccaagag aagcctaatg catgcgtgt gtgctctagg tggctctcgc    1020
tagcgttaat gaggtccaaa tgcgggatta agattctcaa gtcacctcac taggctttgt   1080
ggtgcttgca atgctctacc aatgtgtagg agtaaatgtg ggcagcaaga ccatcaaat   1140
ggtaggtgga tggggtataa atagccctca cccaccaact agccattacc aggaatctgc   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacgaat ttacaccaca atataccctc ttcccttagt   1380
ttaaactgaa ggcgggaaac gacaatctga tcatgagcgg agaattaagg gagtcacgtt   1440
atgaccccg ccgatgacgc gggacaagcc gttttacgtt tggaactgac agaaccgcaa    1500
cgctgcagga attggccgca gctgccattt aaatcaattg ggcgcgcga attcgagctc    1560
ggtacaagct tctggcagac aaagtggcag acatactgtc ccacaaatga atgatgaatc   1620
tgtaaagaa aacgcgtgaa ataatgcgtc tgacaaaggt taggtcggct gcctttaatc    1680
aataccaaag tggtccctac cacgatgaaa aaactgtgca gtcggtttgg cttttttctga   1740
cgaacaaata agattcgtgg ccgacaggtg ggggtccacc atgtgaaggc atcttcagac   1800
tccaataatg gagcaatgac gtaagggctt acgaaataag taagggtagt ttgggaaatg   1860
tccactcacc cgtcagtcta taaatactta gcccctccct cattgttaag ggagcaagga   1920
tccaccatga ctagtaacgg ccgccagtgt gctggtattc gcccttatga cggccgacaa   1980
caacaccgag gcctggacag cagcaccacc aaggacgtga tccagaaggg catcagcgtg   2040
gtgggcgacc tgctgggcgt ggtgggcttc cccttcggcg cgccctggt gagcttctac    2100
accaacttcc tgaacaccat ctggcccagc gaggaccct ggaaggcctt catggagcag    2160
gtggaggccc tgatgaccaa gaagatcgcc gactaccca agaacaaggc actggccgag   2220
ctacagggcc tccagaacaa cgtggaggac tatgtgagcg ccctgagcag ctggcagaag   2280
aaccccgctg caccgttccg caacccccac agccagggcc gcatccgcga gctgttcagc   2340
caggccgaga gccacttccg caacagcatg ccagcttcg tcatcagcgtg ctacgaggtg    2400
ctgttcctga ccacctacgc ccaggccgcc aacacccacc tgttcctgct gaaggacgcc   2460
caaatctacg agaggagtgg ggctacgag aagaggaca tcgccgagtt ctacaagcgc    2520
cagctgaagc tgacccagga gtacaccgac cactgcgtga agtggtacaa cgtgggtcta   2580
gacaagctcc gcggcagcag ctacgagagc tgggtgaact tcaaccgcta ccgccgcgac   2640
atgaccctga ccgtgctgga cctgatcgcc ctgttccccc tgtacacgt gcgcctgtac    2700
cccaaggagt gaagaccga gctgaccccg gacgtgctga ccgacccat cgtgggcgtg    2760
aacaacctgc gcggctacgg caccaccttc agcaacatcg agaactacat ccgcaagccc   2820
cacctgttcg actacctgca ccgcatccag ttccacacag gtttccagcc cggctactac   2880
ggcaacgaca gcttcaacta ctggagcggc aactacgtga gcaccgccc cagcatcggc   2940
agcaacgaca tcatcaccag ccccttctac ggcaacaaga gcagcgagcc cgtgcagaac   3000
cttgagttca acggcgagaa ggtgtaccgc gccgtggcta acaccaacct ggccgtgtgg   3060
ccctctgcag tgtacacgcg gcgtgaccaag gtggagttca gcagtacaa cgaccagacc   3120
gacgaggcca gcacccagac ctacgacagc aagcgcaacg tgggcgccgt gagctgggac   3180
agcatcgacc agctgccccc cgagaccacc gacgagcccc tggagaaggg ctacagccac   3240
cagctgaact acgtgatgtg cttcctgatg cagggcagcc gcggcaccat ccccgtgctg   3300
acctggaccc acaagagcgt cgacttcttc aacatgatcg acagcaagaa gatcacccag   3360
ctgccctga ccaagagcac caacctgggc agcggccaca gtggtgaa gggccccgag    3420
ttcaccggcg gcgacatcct gcgccgcacc agcccggcc agatcagcac cctgcgcgtg   3480
aacatcaccg cccccctgag ccagcgctac cgcgtccgca tccgctacgc cagcaccacc   3540
aacctgcagt tccacaccag catcgacggc cgccccatca ccagggcaa cttcagcgcc   3600
accatgagca gcggcagcaa cctgcagagc ggcagcttcc gcaccgtggg cttcaccacc   3660
cccttcaact tcagcaacgg cagcagcgtg ttcaccctga gcgcccacgt gttcaacagc   3720
ggcaacgagg tgtacatcga ccgcatcgag ttcgtgcccg ccgaggtgac cttcgaggcc   3780
gagtacgacc tggagagggc tcagaaggcc gtgaacgagc tgttcaccag cagcaaccag   3840
atcggcctga gaccgacgt gaccgactac cacatcgatc aggtgtagga gctgagctct   3900
agatccccga atttccccga tcgttcaaac atttggcaat aaagtttctt aagattgaat   3960
cctgttgccg gtcttgcgat gattatcata taatttctgt tgaattacgt taagcatgta   4020
ataattaaca tgtaatgcat gacgttattt atgagatggg tttttatgat tagagtcccg   4080
caattataca tttaatacgc gatagaaaac aaaatatagc gcgcaaacta ggataaatta   4140
tcgcgcgcgg tgtcatctat gttactagat cgggaattgg gtaccagctt gcatgcctgc   4200
agtgcagcgt gacccggtcg tgcccctctc tagagataat gagcattgca tgtctaagtt   4260
ataaaaaatt accacatatt tttttgtca cacttgtttg aagtgcagtt tatctatctt   4320
```

-continued

```
tatacatata tttaaacttt actctacgaa taatataatc tatagtacta caataatatc  4380
agtgttttag agaatcatat aaatgaacag ttagacatgg tctaaaggac aattgagtat  4440
tttgacaaca ggactctaca gttttatctt tttagtgtgc atgtgttctc cttttttttt  4500
gcaaatagct tcacctatat aatacttcat ccatttatt agtacatcca tttagggttt   4560
agggttaatg gttttttatag actaattttt ttagtacatc tattttattc tattttagcc  4620
tctaaattaa gaaaactaaa actctatttt agtttttta tttaataatt tagatataaa   4680
atagaataaa ataaagtgac taaaaattaa acaaataccc tttaagaaat taaaaaaact  4740
aaggaaacat ttttcttgtt tcgagtagat aatgccagcc tgttaaacgc cgtcgacgag  4800
tctaacggac accaaccagc gaaccagcag cgtcgcgtcg ggccaagcga agcagacggc  4860
acggcatctc tgtcgctgcc tctggaccc tctcgagagt tccgctccac cgttggactt   4920
gctccgctgt cggcatccag aaattgcgtg gcggagcggc agacgtgagc cggcacggca  4980
ggcggcctcc tcctcctctc acggcaccgg cagctacggg ggattccttt cccaccgctc  5040
cttcgctttc ccttcctcgc ccgccgtaat aaatagacac cccctccaca ccctctttcc  5100
ccaacctcgt gttgttcgga gcgcacacac acacaaccag atctccccca aatccacccg  5160
tcggcacctc cgcttcaagg tacgccgctc gtcctccccc cccccccctc tctaccttct  5220
ctagatcggc gttccggtcc atggttaggg cccggtagtt ctacttctgt tcatgtttgt  5280
gttagatccg tgtttgtgtt agatccgtgc tgctagcgtt cgtacacgga tgcgacctgt  5340
acgtcagaca cgttctgatt gctaacttgc cagtgttttc ctttggggaa tcctgggatg  5400
gctctagccg ttccgcagac gggatcgatt tcatgatttt ttttgtttcg ttgcataggg  5460
tttggtttgc ccttttcctt tatttcaata tatgccgtgc acttgtttgt cgggtcatct  5520
tttcatgctt ttttttgtct tggttgtgat gatgtggtct ggttgggcgg tcgttctaga  5580
tcggagtaga attctgtttc aaactacctg gtggatttat taattttgga tctgtatgtg  5640
tgtgccatac atattcatag ttacgaattg aagatgatgg atggaaatat cgatctagga  5700
taggtataca tgttgatgcg ggttttactg atgcatatac agagatgctt tttgttcgct  5760
tggttgtgat gatgtggtgt ggttgggcgg tcgttcattc gttctagatc ggagtagaat  5820
actgttttcaa actacctggt gtatttatta attttggaac tgtatgtgtg tgtcatacat  5880
cttcatagtt acgagtttaa gatggatgga aatatcgatc taggataggt atacatgttg  5940
atgtgggttt tactgatgca tatacatgat ggcatatgca gcatctattc atatgctcta  6000
accttgagta cctatctatt ataataaaca agtatgtttt ataattattt tgatcttgat  6060
atacttggat gatggcatat gcagcagcta tatgtgatt tttttagccc tgccttcata  6120
cgctatttat ttgcttggta ctgtttcttt tgtcgatgct cacctgttg tttggtgtta   6180
cttctgcagg gatccccgat catgcaaaaa ctcattaact cagtgcaaaa ctatgcctgg  6240
ggcagcaaaa cggcgttgac tgaactttat ggtatgaaaa atccgtccag ccagccgatg  6300
gccgagctgt ggatgggcgc acatccgaaa agcagttcac gagtgcagaa tgccgccgga  6360
gatatcgttt cactgcgtga tgtgattgag agtgataaat cgactctgct cggagaggcc  6420
gttgccaaac gctttggcga actgcctttc ctgttcaaag tattatgcgc agcacagcca  6480
ctctccattc aggttcatcc aaacaaacac aattctgaaa tcggttttgc caaagaaaat  6540
gccgcaggta tcccgatgga tgccgccgag cgtaactata aagatcctaa ccacaagccg  6600
gagctggttt ttgcgctgac gccttttcctt gcgatgaacg cgtttcgtga attttccgag  6660
attgtctccc tactccagcc ggtcgcaggt gcacatccgg cgattgctca cttttttacaa  6720
cagcctgatg ccgaacgttt aagcgaactg ttcgccagcc tgttgaatat gcagggtgaa  6780
gaaaaatccc gcgcgctggc gattttaaaa tcgccctcg atagccagca gggtgaaccg  6840
tggcaaacga ttcgtttaat ttctgaattt tacccggaag acagcggtct gttctccccg  6900
ctattgctga atgtggtgaa attgaaccct ggcgaagcga tgttcctgtt cgctgaaaca  6960
ccgcacgctt acctgcaagg cgtggcgctg gaagtgatgg caaactccga taacgtgctg  7020
cgtgcgggtc tgacgcctaa atacattgat attccggaac tggttgccaa tgtgaaattc  7080
gaagccaaac cggctaacca gttgttgacc cagccggtga aacaaggtgc agaactggac  7140
ttcccgattc cagtggatga ttttgccttc tcgctgcatg accttagtga taaagaaacc  7200
accattagcc agcagagtgc cgccattttg ttctgcgtcg aaggcgatgc aacgttgtgg  7260
aaaggttctc agcagttaca gcttaaaccg ggtgaatcag cgtttattgc cgccaacgaa  7320
tcaccggtca ctgtcaaagg ccacggccgt ttagcgcgta tttacaacaa gctgtaagga  7380
cttactgaaa aaattaacat ctcttgctaa gctgggagct cgatccgtcg acctgcagat  7440
cgttcaaaca tttggcaata aagtttctta agattgaatc ctgttgccgg tcttgcgatg  7500
attatcatat aatttctgtt gaattacgtt aagcatgtaa taattaacat gtaatgcatg  7560
acgttattta tgagatgggt ttttatgatt agagtcccgc aattatacat ttaatacgcg  7620
atagaaaaca aaatatagcg cgcaaactag gataaattat cgcgcgcggt gtcatctatg  7680
ttactagatc tgctagccct gcaggaaatt taccggtgcc cggcggcca catggccgt    7740
atccgcaatg tgttattaag ttgtctaagc gtcaatttgt ttacaccaca atataccctc  7800
ttccctgggc caggctgggc ccactggcaa agggtgcacc ggacagtccg gtgccccaaa  7860
gccagaaacc ctagcttctg ttttgtgctg tttttcaat ttggttttttg ttctaacttg   7920
tgagtatgtt ctagagttac acctagcact atatgtgagt gtgaatatgc accaacacta  7980
cactagaact cttttggtca aactacttat cgacaacccc tctttatagt acggctaaaa  8040
caaaataaaa gacctaacta tatcacgagt gtccgcaact ccttgacact cggaatacga  8100
agaccttcac tttttgtttc gtcgtttag ccgttgcttc aagttttat ctccgggatt    8160
gttttcacca ttgtagtaca tctacctgta atgcgaccta acttaccatt tgcctctgca  8220
aaacacatgt tagtcacata taaaattacg ttgtcattaa tcactaaaac caaccagggg  8280
cctagatgct ttctagttta aatcccaac aagtcaaaat tctttctatt ttttttttgg   8340
agttccaatt gacatctgaa aggttgtaag gtacacgttt ggctctcatt gataacgggg  8400
gaaagataca gtgcaaacca ccatataatg acccacttct aatcgaatgg acctgtaacg  8460
acgaaatacc ctgtgagaac tatggttcac tcatgttaat tcattgaaat tgttgtagtg  8520
aattgacatg gttgggagcc tgcttagaga gtatagattg tcacttttttt ttggaccgca  8580
acttattttt aaaagatatt gcgatcgctt gtttagtagc tgtttcaggc cccaatgcag  8640
tttctatcgt gatccatttta agtcactcaa cattctcata cttctcattt tgcattaatt  8700
cattccaatc tccactacta taaaatacta gcttcgatgg tcgtcatacg ccatgcacga  8760
agcatgtaga tcaatccgca taccagtggg catctatga taggctgtga aaaccaccca    8820
aatccctact agtggacatt ttatctatag atggaccgtg agaaaccaca caagtctaac  8880
acgacagg                                                            8888
```

SEQ ID NO: 30    moltype = DNA  length = 8885
FEATURE          Location/Qualifiers
source           1..8885
                 mol_type = other DNA
                 organism = synthetic construct
SEQUENCE: 30

```
tacaagaata ttgagacgtg agtacatagc attggcattt tcattagcaa gcatttcaaa    60
agaatttaat tttctcatag caatgtgata tctctcctca cgctcaattc tagttccttc   120
atgtagagca catatgtcca tccacaaatc atgacaattt ttatggtttc taactctatt   180
aaacacatct ttgcaaaggc ctctaaaaag ggtgttttg gccttagcat tccatttctc    240
atagttcaac tcttcaccta caagatttgt gggatctcta ggttcgggga atctttgtgt   300
ggcggctttg tagacaccaa tgtctatagc ctctaaaatat gcttccatac gaattttcca  360
atatggaaaa tcgtcaccat aaaaaacggg agaaggtcca tccccaccgg acatcgttac   420
tctagcggtt aagctaatct aagagcaaca aggctcttat accaattgaa aggatcacga   480
tgcccaagag gggggttga attgggcttt tctaaaaatc aacactaact aaaatctaag    540
caagagccca acttcacccc gacaactagc actaagagaa taatactaga aatcaacaa    600
tgctaagata atacttcaaa tacttgctaa acaaatacaa atgtaaaat acttgaatta    660
agtgcggaat gtaaagcaag gtttagaaga ctcctccaat ttttctagag gtatcaaaga   720
gtcggcactc tccccctagtc ctcgttggag cacctgcgta agggtatcgc tctcccttgg  780
tcatcgcaag aaccaagtgc tcacaacgag atgatccttt gccactccgg cgcggtggat   840
ccctcacgac cgcttacaaa cttgagtcgg gtcaccaaca agatctccac ggtgatcacc   900
gagctcccaa cgccaccaag ccgtctaggt gatgccgatc accaagagta ataagccata   960
gactttcact tgaccaagag aagcctaatg catgcgtgt gtgctctagg tggctctcgc   1020
tagcgttaat gaggtccaaa tgcgggatta agattctcaa gtcacctcac taggctttgt  1080
ggtgcttgca atgctctacc aatgtgtagg agtaaatgtg gcagcaaga ccatcaatat   1140
ggtaggtgga tggggtataa atagccctca cccaccaact agccattacc aggaatctgc  1200
tgcgcatggg cgcaccggac agtccggtgt gccaccggtg cgccaacggt cgactcaaac  1260
ggctagttct gacagctagc cgttggacag atggcatacc ggacagtccg atacgctgtc  1320
cggtgtgcct ctaaatttac accacaatat accctcttcc cttcacgaac tgatagttta  1380
aactgaaggc gggaaacgac aatctgatca tgagcggaga attaagggag tcacgttatg  1440
accccccgccg atgacgcggg acaagccgtt tacgtttgg aactgacaga accgcaacgc   1500
tgcaggaatt ggccgcagct gccatttaaa tcaattgggc gcgccgaatt cgagctcggt  1560
acaagcttct ggcagacaaa gtggcagaca tactgtccca caaatgaaga tggaatctgt  1620
aaaagaaaac gcgtgaaata atgcgtctga caaaggttag gtcggctgcc tttaatcaat  1680
accaaagtgg tccctaccac gatggaaaaa ctgtgcagtc ggtttggctt ttctgacga    1740
acaaataaga ttcgtggccg acaggtgggg gtccaccatg tgaaggcatc ttcagactcc  1800
aataatggag caatgacgta agggcttacg aaataagtaa gggtagtttg ggaaatgtcc  1860
actcaccgt cagtctataa atacttagcc cctccctcat tgttaaggga gcaaggatcc   1920
accatgacta gtaacggccg ccagtgtgct ggtattcgcc cttatgacgg ccgacaacaa  1980
caccgaggcc tggacagcag caccaccaag gacgtgatcc agaagggcat cagcgtggtg  2040
ggcgacctgc tgggcgtggt gggcttcccc ttcggcggcg ccctggtgag cttctacacc  2100
aacttcctga acaccatctg gcccagcgag gaccccctgga aggccttcat ggagcaggtg 2160
gaggccctga tggaccagaa gatcgccgac tacgccaaga acaaggcact ggccgagcta  2220
cagggcctcc agaacaacgt ggaggactat gtgagcgccc tgagcagctg gcagaagaac  2280
cccgctgcac cgttccgcaa cccccacagc cagggccgca tccgcgagct gttcagccag  2340
gccgagagcc acttccgcaa cagcatgccc agcttccgca tcagcggca cgaggtgctg  2400
ttcctgacca cctacgccca ggccgccaac acccacctgt tcctgctgaa ggacgcccaa  2460
atctacggag aggagtgggg ctacgagaag gaggacatcg ccgagttcta caagcgccag  2520
ctgaagctga cccaggagta caccgaccac tgcgtgaagt ggtacaacgt gggtctagac  2580
aagctcgcgc gcagcagcta cgagagctgg gtgaactca accgctaccg ccgcgagatg  2640
accctgaccg tgctggacct gatcgccctg ttcccctgt acgacgtgcg cctgtacccc  2700
aaggaggtga gaccgagct gaccgcgac gtgctgaccg acccccatcgt gggcgtgaac  2760
aacctgcgcg gctacggcac caccttcagc aacatcgaga actacatccg caagcccac   2820
ctgttcgact acctgcaccg catccagttc cacacgcgtt tccagcccg ctactacgg   2880
aacgacagct tcaactactg gagcggcaac tacgtgagca cccgcccag catcggcagc  2940
aacgacatca tcaccagccc cttctacggc aacaagagca gcgagcccgt gcagaacctt  3000
gagttcaacg gcgagaaggt gtaccgcgcc gtggctaaca ccaacctggc cgtgtggccc  3060
tctgcagtgt acagcggcgt gaccaaggtg gagttcagcc agtacaacga ccagaccgac  3120
gaggccagca cccagaccct cgacagcaag cgcgcgtgag ctgggacagc ctgggacagc  3180
atcgaccagc tgccccccga gaccaccgac gagccctgg agaagggcta cagccaccag  3240
ctgaactacg tgatgtgctt cctgatgcag ggcagccgcg gcaccatccc cgtgctgacc  3300
tggacccaca gagcgtcga cttcttcaac atgatcgaca gcaagaagat cacccagctg  3360
ccctgacca agagccaacca cctgggcagc ggcaccaaggg tggtgaaggg ccccgggcttc 3420
accgccgcg acatcctgcg cgcaccagc cccggccaga tcagcaccct gcgcgtgaac  3480
atcaccgccc cctgagcca gcgctaccgc gtccgcatcc gctacgccag caccaccaac  3540
ctgcagttcc acaccagcat cgacggccgc cccatcaacc agggcaactt cagcgccacc  3600
atgagcagcg gcagcaacct gcagagcggc agcttccgca ccgtgggctt caccacccc   3660
ttcaacttca gcaacggcag cagcgtgttc acctgagcc cacgtgacctt cgaggccgag  3720
aacgaggtgt acatcgaccg catcgagttc gtgccccgcc aggtgaccgc cagccgagc   3780
tacgacctgg agaggctca aaggccgtg aacgagctgt caccagcag caccagatc     3840
ggcctgaaga ccgacgtgac cgactaccac atcgatcagg gtaggagct gagctctaga  3900
tccccgaatt tccccgatcg ttcaaacatt tggcaataaa gtttcttaag attgaatcct  3960
gttgccggtc ttgcgatgat tatcatataa tttctgttga attacgttaa gcatgtaata  4020
attaacatgt aatgcatgac gttattttatg agatgggttt ttatgattag agtcccgcaa  4080
ttatacattt aatacgcgat agaaaacaaa atatagcgcg caaactagga taaattatcg  4140
cgcgcggtgt catctatgtt actagatcgg gaattgggta ccagcttgca tgcctgcagt  4200
gcagcgtgac ccggtcgtgc ccctctctag agataatgag cattgcatgt ctaagttata  4260
aaaaattacc acatattttt tttgtcacac ttgtttgaag tgcagtttat ctatctttat  4320
```

```
acatatattt aaactttact ctacgaataa tataatctat agtactacaa taatatcagt  4380
gttttagaga atcatataaa tgaacagtta gacatggtct aaaggacaat tgagtatttt  4440
gacaacagga ctctacagtt ttatcttttt agtgtgcatg tgttctcctt tttttttgca  4500
aatagcttca cctatataat acttcatcca ttttattagt acatccattt agggtttagg  4560
gttaatggtt tttatagact aatttttttta gtacatctat tttattctat tttagcctct  4620
aaattaagaa aactaaaact ctattttagt ttttttattt aataatttag atataaaata  4680
gaataaaata aagtgactaa aaattaaaca aatacccttt aagaaattaa aaaaactaag  4740
gaaacatttt tcttgtttcg agtagataat gccagcctgt taaacgccgt cgacgagtct  4800
aacggacacc aaccagcgaa ccagcagcgt cgcgtcgggc caagcgaagc agacggcacg  4860
gcatctctgt cgctgcctct ggaccnnctct cgagagttcc gctccaccgt tggacttgct  4920
ccgctgtcgg catccagaaa ttgcgtggcg gagcggcaga cgtgagccgg cacggcaggc  4980
ggcctcctcc tcctctcacg gcaccggcag ctacgggga ttccttttccc accgctcctt  5040
cgcttttccct tcctcgcccg ccgtaataaa tagacaccc ctccacaccc tctttcccca  5100
acctcgtgtt gttcggagcg cacacacaca caaccagatc tcccccaaat ccaccgtcg  5160
gcacctccgc ttcaaggtac gccgctcgtc ctccccccccc ccccctctct accttctcta  5220
gatcggcgtt ccggtccatg gttagggccc ggtagttcta cttctgttca tgtttgtgtt  5280
agatccgtgt ttgtgttaga tccgtgctgc tagcgttcgt acacggatgc gacctgtacg  5340
tcagacacgt tctgattgct aacttgccag tgtttctctt tggggaatcc tgggatggct  5400
ctagccgttc cgcagacggg atcgatttca tgatttttttt tgtttcgttg catagggttt  5460
ggtttgccct tttcctttat ttcaatatat gccgtgcact tgtttgtcgg gtcatctttt  5520
catgcttttt tttgtcttgg ttgtgatgat gtggtctggt tgggcggtcg ttctagatcg  5580
gagtagaatt ctgtttcaaa ctacctggtg gatttattaa tttggatct gtatgtgtgt  5640
gccatacata ttcatagtta cgaattgaag atgatggatg gaaatatcga tctaggatag  5700
gtacacatgt tgatgcgggt tttactgatg catatacaga gatgctttt gttcgcttgg  5760
ttgtgatgat gtggtgtggt tgggcggtcg ttcattcgtt ctagatcgga gtagaatact  5820
gtttcaaact acctggtgta tttattaatt ttggaactgt atgtgtgtgt catacatctt  5880
catagttacg agtttaagat ggatggaaat atcgatctag gataggtata catgttgatg  5940
tgggttttac tgatgcatat acatgatggc atatgcagca tctattcata tgctctaacc  6000
ttgagtacct atctattata ataaacaagt atgttttata attatttga tcttgatata  6060
cttggatgat ggcatatgca gcagctatat gtggatttt ttagccctgc cttcatacgc  6120
tatttatttg cttggtactg tttctttgt cgatgctcac cctgttgttt ggtgttactt  6180
ctgcagggat ccccgatcat gcaaaaactc attaactcag tgcaaaacta tgcctggggc  6240
agcaaaacgg cgttgactga actttatggt atggaaaatc cgtccagcca gccgatggcc  6300
gagctgtgga tgggcgcaca tccgaaaagc agttcacgag tgcagaatgc cgccggagat  6360
atcgttcac tgcgtgatgt gattgagagt gataaatcga ctctgctcgg agaggccgt  6420
gccaaacgct ttggcgaact gccttttcctg ttcaaagtat tatgcgcagc acagccactc  6480
tccattcagg ttcatccaaa caaacacaat tctgaaatcg gttttgccaa agaaaatgcc  6540
gcaggtatcc cgatggatgc cgccgagcgt aactataaag atcctaacca caagccggag  6600
ctggttttttg cgctgacgcc tttccttgcg atgaacgcgt ttcgtgaatt ttccgagatt  6660
gtctccctac tccagccggt cgcaggtgca catccggcga ttgctcactt tttacaacag  6720
cctgatgccg aacgtttaag cgaactgttc gccagcgtcgt tgaatatgca gggtgaagaa  6780
aaatcccgcg cgctggcgat tttaaaatcg gccctcgata gccagcaggg tgaaccgtgg  6840
caaacgattc gtttaatttc tgaattttac ccggaagaca gcggtctgtt ctccccgcta  6900
ttgctgaatg tggtgaaatt gaaccctggc gaagcgatgt tcctgttcgc tgaaacaccg  6960
cacgcttacc tgcaaggcgt ggcgctggaa gtgatggcaa actccgataa cgtgctgcgt  7020
gcgggtctga cgcctaaata cattgatatt ccggaactgg ttgccaatgt gaaattcgaa  7080
gccaaaccgg ctaaccagtt gttgacccag ccggtgaaac aaggtgcaga actgactttc  7140
ccgattccag tggatgattt tgccttctcg ctgcatgacc ttagtgataa agaaaccacc  7200
attagccagc agagtgccgc cattttgttc tgcgtcgaag gcgatgcaac gttgtggaaa  7260
ggttctcagc agttacagct taaaccgggt gaatcagcgt ttattgccgc caacgaatca  7320
ccggtgactg tcaaaggcca cggccgtttta gcgcgtgttt acaacaagct gtaagagctt  7380
actgaaaaaa ttaacatctc ttgctaagct gggagctcga tccgtcgacc tgcagatcgt  7440
tcaaacattt ggcaataaag tttcttaaga ttgaatcctg ttgccggtct tgcgatgatt  7500
atcatataat ttctgttgaa ttacgttaag catgtaataa ttaacatgta atgcatgacg  7560
ttatttatga gatgggtttt tatgattaga gtcccgcaat tatacattta atacgcgata  7620
gaaaacaaaa tatagcgcgc aaactaggat aaattatcgc gcgcggtgtc atctatgtta  7680
ctagatctgc tagccctgca ggaaatttac cggtgcccgg gcggccagca tggccgtatc  7740
cgcaatgtgt tattaagttg tctaagcgtc aatttgttta caccacaata taccctcttc  7800
cctgggccag ctgggcccca ctggcaaagg gtgcaccgga cagtccggtg ccccaaagcc  7860
agaaacccta gcttctgttt tgtgctgttt tttcaattttg gttttgttc taacttgtga  7920
gtatgttcta gagttacacc tagcactata tgtgagtgta aatatgcacc aacactacac  7980
tagaactctt ttggtcaaac tacttatcga caaccctct ttatagtacg gctaaaacaa  8040
aataaaagac ctaactatat cacgagtgtc cgcaactcct tgacactcgg aatacgaaga  8100
ccttcacttt tgtttcgtc gctttagccg ttgcttcaag tttttatctc cgggattgtt  8160
ttcaccattg tagtacatct acctgtaatg cgacctaact taccatttgc ctctgcaaaa  8220
cacatgttag tcacatataa aattacgttg tcattaatca ctaaaaccaa ccagggggcct  8280
agatgctttc tagtttaaat ccccaacaag tcaaaattct ttctatttt tttttgcaagt  8340
tccaattgac atctgaaagg ttgtaaggta cacgttggc tctcattgat aacgggggaa  8400
agatacagtg caaaccacca tataatgacc cacttctaat cgaatggacc tgtaacgacg  8460
aaatcccctg tgagaactat ggttcactca tgttaattca ttgaaattgt tgtagtgaat  8520
tgacatggtt gggagcctgc ttagagagta tagattgtca cttttttttg gaccgcaact  8580
tatttttaaa agatattgcg atcgcttgtt tggtagctgt ttcaggcccc aatgcagttt  8640
ctatcgtgat ccatttaagt cactcaacat tctcatactt ctcatttgc attaattcat  8700
tccaatctcc actactataa aatactagct tcgatggtcg tcatacgcca tgcacgaagc  8760
atgtagatca atccgcatac cagtgggcat ctatagatag gctgtgaaaa ccacccaat  8820
ccctactagt ggacattttta tctatagatg gaccgtgaga aaccacacaa gtctaacacg  8880
acagg                                                                8885
```

```
SEQ ID NO: 31            moltype = DNA   length = 23
FEATURE                  Location/Qualifiers
source                   1..23
                         mol_type = other DNA
                         organism = synthetic construct
SEQUENCE: 31
ccgccttcag tttaaactat cag                                          23

SEQ ID NO: 32            moltype = DNA   length = 5403
FEATURE                  Location/Qualifiers
source                   1..5403
                         mol_type = other DNA
                         organism = synthetic construct
SEQUENCE: 32
tacaagaata ttgagacgtg agtacatagc attggcattt tcattagcaa gcatttcaaa   60
agaatttaat tttctcatag caatgtgata tctctcctca cgctcaattc tagttccttc  120
atgtagagca catatgtcca tccacaaatc atgacaattt ttatggtttc taactctatt  180
aaacacatct ttgcaaaggc ctctaaaaag ggtgttttg  gccttagcat tccatttctc  240
atagttcaac tcttcaccta caagatttgt gggatctcta ggttcgggga atctttgtgt  300
ggcggctttg tagacaccaa tgtctatagc ctctaaatat gcttccatac gaattttcca  360
atatggaaaa tcgtcaccat aaaaaacggg agaaggtcca tccccaccgg acatcgttac  420
tctagcggtt aagctaatct aagagcaaca aggctcttat accaattgaa aggatcacga  480
tgcccaagag gggggttga  attgggcttt tctaaaaatc aacactaact aaaatctaag  540
caagagccca acttcacccc gacaactagc actaagagaa taatactaga aatacaacaa  600
tgctaagata atacttcaaa tacttgctaa acaaatacaa aatgtaaaat acttgaatta  660
agtgcggaat gtaaagcaag gtttagaaga ctcctccaat tttctagag  gtatcaaaga  720
gtcggcactc tcccctagtc ctcgttggag cacctgcgta agggtatcgc tctcccttgg  780
tcatcgcaag aaccaagtgc tcacaacgag atgatccttt gccactccgg cgcggtggat  840
ccctcacgac cgcttacaaa cttgagtcgg gtcaccaaca agatctccac ggtgatcacc  900
gagctcccaa cgccaccaag ccgtctaggt gatgccgatc accaagagta ataagccata  960
gactttcact tgaccaagag aagcctaatg catgcgtgt  gtgctctagg tggctctcgc 1020
tagcgttaat gaggtccaaa tgcgggatta agattctcaa gtcacctcac taggctttgt 1080
ggtgcttgca atgctctacc aatgtgtagg agtaaatgtg ggcagcaaga ccatcaatat 1140
ggtaggtga  tggggtataa atagccctca cccaccaact agccattacc aggaatctgc 1200
tgcgcatggg cgcaccggac agtccggtgt gccaccggtg cgccaacggt cgactcaaac 1260
ggctagttct gacagctagc cgttggacag atggcatacc ggacagtccg atacgctgtc 1320
cggtgtgcct ctaaaattca actcacgaac tgatagttta aactgaaggc gggaaacgag 1380
aatctgatca tgagcggaga attaaggag  tcacgttatg accccgccg  atgacgcggg 1440
acaagccgtt ttacgtttgg aactgacaga accgcaacgc tgcaggaatt ggccgcagct 1500
gccatttaaa tcaattgggc gcgccgaatt cgagctcggt acaagcttct ggcagacaaa 1560
gtggcagaca tactgtccca caaatgaaga tggaatctga aaagaaaac  gcgtgaaata 1620
atgcgtctga caaggttag gtcggctgcc tttaatcaat accaaagtgg tccctaccac 1680
gatgaaaaa  ctgtgcagtc ggtttggctt tttctgacga acaaataaga ttcgtggccg 1740
acaggtgggg gtccaccatg tgaaggcatc ttcagactcc aataatggag caatgacgta 1800
agggcttacg aaataagtaa gggtagtttg ggaaatgtcc actcacccgt cagtctataa 1860
atacttagcc cctccctcat tgttaaggga gcaaggatcc accatgacta gtaacggcca 1920
ccagtgtgct ggtattcgcc cttatgacgg ccgacaacaa caccgaggcc tggacagcag 1980
caccaccaag gacgtgatcc agaagggcat cagcgtggtg ggcgacctgc tgggcgtggt 2040
gggcttcccc ttcggcggcg ccctggtgag cttctacacc aacttcctga acaccatctg 2100
gcccaccgag gaccccctgga aggccttcat ggagcaggta gaggccctga tggaccagaa 2160
gatcgccgac tacgccaaga caaggcact  ggccgagcta cagggcctcc agaacaacgt 2220
ggaggactat gtgagcgccc tgagcagctg cagaagaac ccgctgcac  cgttccgcaa 2280
cccccacagc cagggccgca tccgcgagct gttcagccag gccgagagcc acttccgcaa 2340
cagcatgccc agcttcgcca tcagcgccta cgaggtgctg ttcctgacca cctacgccca 2400
ggccgccaac acccacctgt tcctgctgaa ggacgcccaa atctacgag  aggagtgggg 2460
ctacgagaag gaggacatcg ccgagttcta caagcgccag ctgaagctga cccaggagta 2520
caccgaccac tgcgtgaagt ggtacaacgt gggtctagac aagctccgcg gcagcagcta 2580
cgagagctgg gtgaacttca accgctaccg ccgcgagatg accctgaccg tgctggacct 2640
gatcgccctg ttccccctgt acgacgtgcg cctgtacccc aaggaggtga gaccgagct  2700
gacccgcgac gtgctgaccg accccatcgt gggcgtgaac aacctgcgcg gctacgcac  2760
caccttcagc aacatcgaga actacatccg caagccccac ctgttcgact acctgcaccg 2820
catccagttc cacacgcgtt tccagcccgg ctactacgcc aacgacagct caactactg  2880
gagcggcaac tacgtgagca cccgccccag catcggcagc tcaccagccc 2940
cttctacggc aacaagagca gcgagcccgt gcagaacctt gagttcaacg gcgagaaggt 3000
gtaccgcgcc gtggctaaca ccaacctggc cgtgtggccc tctgcagtgt acagcggcgt 3060
gaccaaggtg gagttcagcc agtacaacga ccagaccgac gaggccagca ccagacccta 3120
cgacagcaag cgcaacgtgg cgccgtgag ctgggacagc atcgaccagc tgcccccga  3180
gaccaccgac gagcccctgg agaagggcta cagccaccag ctgaactacg tgatgtgctt 3240
cctgatgcag ggcagccgcg gcaccatccc cgtgctgacc tggacccaca gagcgtcga  3300
cttcttcaac atgatcgaca gcaagaagat cacccagctg cccctgacca agagcaccaa 3360
cctgggcagc ggcaccagcg tggtgaaggg ccccggcttc accggcggcg acatcctgcg 3420
ccgcaccagc ccggccaga  tcagcaccct gcgcgtgaac atcaccgccc cctgagccc  3480
gcgctaccgc gtccgcatcc gctacgccag caccaccaac ctgcagttcc acaccagcat 3540
cgacggccgc cccatcaacc agggcaactt cagcgccacc atgagcagcg gcagcaacct 3600
gcagagcggc agcttccgca ccgtgggctt caccacccc  ttcaacttca gcaacggcag 3660
cagcgtgttc accctgagcg cccacgtgtt caacagcggc aacgaggtgt acatcgaccg 3720
catcgagttc gtgcccgccg aggtgaccgt cgaggccgag tacgacctgg agagggctca 3780
gaaggccgtg aacgagctgt tcaccagcag caaccagatc ggcctgaaga ccgacgtgac 3840
```

```
cgactaccac atcgatcagg tgtaggagct gagctctaga tccccgaatt tccccgatcg   3900
ttcaaacatt aacatctctt gctaagctgg gagctcgatc cgtcgacctg cagatcgttc   3960
aaacatttgg caataaagtt tcttaagatt gaatcctgtt gccggtcttg cgatgattat   4020
catataaattt ctgttgaatt acgttaagca tgtaataatt aacatgtaat gcatgacgtt   4080
atttatgaga tgggttttta tgattagagt cccgcaatta tacatttaat acgcgataga   4140
aaacaaaata tagcgcgcaa actaggataa attatcgcgc gcggtgtcat ctatgttact   4200
agatctgcta gccctgcagg aaatttaccg gtgcccgggc ggccagcatg gccgtatccg   4260
caatgtgtta ttaagttgtc taagcgtcaa tttgtttaca ccacaatata ccctcttccc   4320
tgggccaggc tgggcccact ggcaaagggt gcaccggaca gtccggtgcc ccaaagccag   4380
aaaccctagc ttctgttttg tgctgttttt tcaatttggt ttttgttcta acttgtgagt   4440
atgttctaga gttacaccta gcactatatg tgagtgtgaa tatgcaccaa cactacacta   4500
gaactctttt ggtcaaacta cttatcgaca acccctcttt atagtacggc taaaacaaaa   4560
taaaagacct aactatatca cgagtgtccg caactccttg cacactcggaa tacgaagacc   4620
ttcactttt gtttcgtcgc tttagccgtt gcttcaagtt tttatctccg ggattgtttt   4680
caccattgta gtacatctac ctgtaatgcg acctaactta ccatttgcct ctgcaaaaca   4740
catgttagtc acatataaaa ttacgttgtc attaatcact aaaaccaacc aggggcctag   4800
atgctttcta gtttaaatcc ccaacaagtc aaaattcttt ctattttttt ttgcaagttc   4860
caattgacat ctgaaaggtt gtaaggtaca cgtttggctc tcattgataa cggggggaaag   4920
atacagtgca aaccaccata taatgaccca cttctaatcg aatggacctg taacgacgaa   4980
ataccctgtg agaactatgg ttcactcatg ttaaattcatt gaaattgttg tagtgaattg   5040
acatggttgg gagcctgctt agagagtata gattgtcact tttttttgga ccgcaactta   5100
tttttaaaag atattgcgat cgcttgttta gtagctgttt caggccccaa tgcagtttct   5160
atcgtgatcc atttaagtca ctcaacattc tcatacttct cattttgcat taattcattc   5220
caatctccac tactataaaa tactagcttc gatggtcgtc atacgccatg cacgaagcat   5280
gtagatcaat ccgcatacca gtgggcatct atagataggc tgtgaaaacc acccaaatcc   5340
ctactagtgg acattttatc tatagatgga ccgtgagaaa ccacacaagt ctaacacgac   5400
agg                                                                 5403

SEQ ID NO: 33         moltype = DNA   length = 5426
FEATURE               Location/Qualifiers
source                1..5426
                      mol_type = other DNA
                      organism = synthetic construct
SEQUENCE: 33
tacaagaata ttgagacgtg agtacatagc attggcattt tcattagcaa gcatttcaaa    60
agaatttaat tttctcatag caatgtgata tctctcctca cgctcaattc tagttccttc   120
atgtagagca catatgtcca tccacaaatc atgacaattt ttatggtttc taactctatt   180
aaacacatct ttgcaaaggc ctctaaaaag ggtgttttg gccttagcat tccatttctc   240
atagttcaac tcttcaccta caagatttgt gggatctcta ggtcgggga atctttgtgt   300
ggcggctttg tagacaccaa tgtctatagc ctctaaatat gcttccatac gaatttttcca   360
atatggaaaa tcgtcaccat aaaaaacggg agaaggtcca tccccaccgg acatcgttac   420
tctagccggtt aagctaatct aagagcaaca aggctcttat accaattgaa aggatcacga   480
tgcccaagag gggggttga attgggcttt tctaaaaatc aacactaact aaaatctaag   540
caagagccca acttcacccc gacaactagc actaagagaa taatactaga aatacaacaa   600
tgctaagata atacttcaaa tacttgctaa acaaatacac aatgtaaaat acttgaatta   660
agtgcggaat gtaaagcaag gtttagaaga ctcctccaat ttttctagag gtatcaaaga   720
gtcggcactc tcccctagtc ctcgttggag cacctgcgta agggtatcgc tctcccttgg   780
tcatcgcaag aaccaagtgc tcacaacgag atgatccttt gccactccgg cgcggtggat   840
cccctcacga cgcttacaaa cttgagtcgg gtcaccaaca agatccccac ggtgatcacc   900
gagctcccaa cgccaccaag ccgtctaggt gatgccgatc accaagagta ataagccata   960
gactttcact tgaccaagag aagcctaatg catgcggtgt gtgctctaga tggctctcga  1020
tagcgttaat gaggtccaaa tgcgggatta agattctcaa gtcacctcac taggctttgt  1080
ggtgcttgca atgctctacc aatgtgtagg agtaaatgtg ggcagcaaga ccatcaatat  1140
ggtaggtgga tgggggtataa atagccctca cccaccaact agccattacc aggaatctgc  1200
tgcgcatggg cgcaccggac agtccggtgt gccaccggtc cgccaacggt cgactcaaac  1260
ggctagttct gacagctagc cgttggacag atggcatacc ggacagtccg atacgctgtc  1320
cggtgtgcct ctaaaattca actcacgaat ttacaccaca atataccctc ttcccttagt  1380
ttaaactgaa ggcgggaaac gacaatctga tcatgagcgg agaattaagg gagtcacgtt  1440
atgaccccg ccgatgacgc gggacaagcc gttttacgtt tggaactgac agaaccgcaa  1500
cgctgcagga attggccgca gctgccattt aaatcaattg ggcgcgccga attcgagctc  1560
ggtacaagct tctggcagac aaagtggcag acatactgtc ccacaaatga agatggaatc  1620
tgtaaaagaa aacgcgtgaa ataatgcgtc tgacaaaggt taggtcggct gcctttaatc  1680
aataccaaag tggtccctac cacgatggaa aaactgtgca gtcggtttgg cttttctga   1740
cgaacaaata agattcgtgg ccgacaggtg gggtccacc atgtgaaggc atcttcagac  1800
tccaataatg gagcaatgac gtaagggctt acgaaataag taagggtagt ttgggaaatg  1860
tccactcacc cgtcagtcta taaatactta gcccctccct cattgttaag ggagcaagga  1920
tccaccatga ctagtaacgg ccgccagtgt gctggtattc gcccttatga cggccgacaa  1980
caacaccgag gcctggacag cagcaccacc aaggacgtga tccagaaggg catcagcgtg  2040
gtgggcgacc tgctgggcgt ggtgggcttc cccttcgtgc gcgccctgtt gagcttctac  2100
accaacttcc tgaacaccat ctggcccagc gaggacccct ggaaggcctt catggagcag  2160
gtggaggccc tgatgaccca agatcgccc gactacgcca agaacaaggc actggccgag  2220
ctacagggcc tccagaacaa cgtggaggac tatgtgagcg ccctgagcag ctggcagaag  2280
aacccgctg caccgttccg caaccccac agccagggcc gcatccgcga gctgttcagc  2340
caggcggca gccacttccg caacagcatg cccatcagcg ccatcagggtg  2400
ctgttcctga ccacctacgc ccaggccgcc aacaccacc tgttcctgct gaaggacgcc  2460
caaatctacg gagaggagtg gggctacgag aaggaggaca cgccgagtt ctacaagcgc  2520
cagctgaagc tgacccagga gtacaccgac cactgcgtga gtggtacaa cgtgggctc  2580
gacaagctcc gcgcagcag ctacgagagc tgggtgaact tcaaccgcta ccgccgcgag  2640
atgaccctga ccgtgctgga cctgatcgcc ctgttccccc tgtacgacgt gcgcctgtac  2700
```

```
cccaaggagg tgaagaccga gctgacccgc gacgtgctga ccgacccat cgtgggcgtg   2760
aacaacctgc gcggctacgg caccaccttc agcaacatcg agaactacat ccgcaagccc   2820
cacctgttcg actacctgca ccgcatccag ttccacacgc gtttccagcc cggctactac   2880
ggcaacgaca gcttcaacta ctggagcggc aactacgtga gcacccgccc cagcatcggc   2940
agcaacgaca tcatcaccag ccccttctac ggcaacaaga gcagcgagcc cgtgcagaac   3000
cttgagttca acggcgagaa ggtgtaccgc gccgtggcta acaccaacct ggccgtgtgg   3060
ccctctgcag tgtacagcgg cgtgaccaag gtggagttca gccagtacaa cgaccagacc   3120
gacgaggcca gcacccagac ctacgacagc aagcgcaacg tgggcgccgt gagctgggac   3180
agcatcgacc agctgccccc cgagaccacc gacgagcccc tggagaaggg ctacagccac   3240
cagctgaact acgtgatgtg cttcctgatg cagggcagcc gcggcaccat ccccgtgctg   3300
acctggaccc acaagagcgt cgacttcttc aacatgatcg acagcaagaa gatcacccag   3360
ctgccctga ccaagagcac caacctgggc agcggcacca gcgtggtgaa gggccccggc   3420
ttcaccggcg gcgacatcct gcgccgcacc agccccggcc agatcagcac cctgcgcgtg   3480
aacatcaccg cccccctgag ccagcgctac cgcgtccgca tccgctacgc cagcaccacc   3540
aacctgcagt tccacaccag catcgacggc cgcccccatca accagggcaa cttcagcgcc   3600
accatgagca gcggcagcaa cctgcagagc ggcagcttcc gcaccgtggg cttcaccacc   3660
cccttcaact tcagcaacgg cagcagcgtg ttcaccctga cgcccacgt gttcaacagc   3720
ggcaacgagg tgtacatcga ccgcatcgag ttcgtgcccg ccgaggtgac cttcgaggcc   3780
gagtacgacc tggagagggc tcagaaggcc gtgaacgagc tgttcaccag cagcaaccag   3840
atcggcctga agaccgacgt gaccgactac cacatcgatc aggtgtagga gctgagctct   3900
agatccccga atttccccga tcgttcaaac attaacatct cttgctaagc tgggagctcg   3960
atccgtcgac ctgcagatcg ttcaaacatt tggcaataaa gtttcttaag attgaatcct   4020
gttgccggtc ttgcgatgat tatcatataa tttctgttga attacgttaa gcatgtaata   4080
attaacatgt aatgcatgac gttatttatg agatgggttt ttatgattag agtcccgcaa   4140
ttatacattt aatacgcgat agaaaacaaa atatagcgcg caaactagga taaattatcg   4200
cgcgcggtgt catctatgtt actagatctg ctagcccctg aggaaattta ccggtgcccg   4260
ggcggccagc atggccgtat ccgcaatgtg ttattaagtt gtctaagcgt caatttgttt   4320
acaccacaat atccctctt ccctgggcca ggctgggccc actggcaaag ggtgcaccgg   4380
acagtccggt gccccaaagc cagaaaccct agcttctgtt ttgtgctgtt ttttcaattt   4440
ggttttttgtt ctaacttgtg agtatgttct agagttacac ctagcactat atgtgagtgt   4500
gaatatgcac caacactaca ctagaactct tttggtcaaa ctacttatcg acaacccctc   4560
tttatagtac ggctaaaaca aaataaaaga cctaactata tcacgagtgt ccgcaactcc   4620
ttgacactcg gaatacgaag accttcactt tttgtttcgt cgctttagcc gttgcttcaa   4680
gttttatct ccgggattgt tttcaccatt gtagtacatc tacctgtaat gcgacctaac   4740
ttaccatttg cctctgcaaa acacatgtta gtcacatata aaattacgtt gtcattaatc   4800
actaaaacca accaggggcc tagatgcttt ctagtttaaa tccccaacaa gtcaaaattc   4860
tttctatttt tttttgcaag ttccaattga catctgaaag gttgtaaggt acacgtttgg   4920
ctctcattga taacggggga aagatacagt gcaaaccacc atataatgac ccactttctaa   4980
tcgaatggac ctgtaacgac gaaatacccct gtgagaacta tggttcactc atgttaattc   5040
attgaaattg ttgtagtgaa ttgacatggt tgggagcctg cttagagagt atagattgtc   5100
actttttttt ggaccgcaac ttatttttaa aagatattgc gatcgcttgt ttagtagctg   5160
tttcaggccc caatgcagtt tctatcgtga tccatttaag tcactcaaca ttctcatact   5220
tctcattttg cattaattca ttccaatctc cactactata aaatactagc ttcgatggtc   5280
gtcatacgcc atgcacgaag catgtagatc aatccgcata ccagtgggca tctatagata   5340
ggctgtgaaa accacccaaa tccctactag tggacatttt atctatagat ggaccgtgag   5400
aaaccacaca agtctaacac gacagg                                       5426

SEQ ID NO: 34          moltype = DNA   length = 7747
FEATURE                Location/Qualifiers
source                 1..7747
                       mol_type = other DNA
                       organism = synthetic construct
SEQUENCE: 34
tacaagaata ttgagacgtg agtcatagc attggcattt tcattagcaa gcatttcaaa     60
agaattttaat tttctcatag caatgtgata tctctcctca cgctcaattc tagttccttc    120
atgtagagca catatgtcca tccacaaatc atgacaattt ttatggtttc taactctatt    180
aaacacatct ttgcaaaggc ctctaaaaag ggtgtttttg gccttagcat tccatttctc    240
atagttcaac tcttcaccta caagatttgt gggatctcta ggttcgggga tctttgtgt     300
ggcggctttg tagacaccaa tgtctatagc ctctaaatat gcttccatac gaattttcca    360
atatggaaaa tcgtcaccat aaaaacgggg agaaggtcca tccccaccgg acatcgttac    420
tctagcggtt aagctaatct aagagcaaca aggctcttat accaattgaa aggatcacga    480
tgcccaagag gggggttga attgggcttt tctaaaaatc aacactaact aaaatctaag    540
caagagccca acttcaccc gacaactagc actaagagaa taatactaga aatacaacaa    600
tgctaagata atacttcaaa tacttgctaa acaaatacac aatgtaaaat acttgaatta    660
agtgcgaat gtaaagcaag gttagaagaa ctcctccaat tttctagag gtatcaaaga     720
gtcggcactc tccccctagtc ctcgttggag cacctgcgta agggtatcgc tctcccttgg    780
tcatcgcaag aaccaagtgc tcacaacgag atgatccttt gccactccgg cgcggtggat    840
ccctcacgac cgcttacaaa cttgagtcgg gtcaccaaca agatctccac ggtgatcacc    900
gagctcccaa cgccaccaag ccgtctaggt gatgccgatc accaagagta ataagccata    960
gactttcact tgaccaagag aagcctaatg catgcggtgt gtgctctagg tggctctcgc   1020
tagcgttaat gaggtccaaa tgcgggatta agattctcaa gtcacctcac taggctttgt   1080
ggtgcttgca atgctctacc aatgtgtagg agtaaatgtg ggcagcaaga ccatcaatat   1140
ggtaggtgga tggggtataa atagccctca cccaccaact agccattacc aggaatctgc   1200
tgggagtggg tgcaccggac cacggtgt gccacggtg ccgcaacggt cgactcaaac   1260
ggctagttct gacagctagc cgttggacag atggcatacc ggacagtccg atacgctgtc   1320
cggtgtgcct ctaaaattca actcacgaat ttaaactgaa ggcgggaaac gacaatctga   1380
tcatgagcgg agaattaagg gagtcacgtt atgacccccg ccgatgacgc gggacaagcc   1440
gttttacgtt tggaactgac agaaccgcaa cgctgcagga attggccgca gctgcctttt   1500
aaatcaattg ggcgcgccga attcgagctc ggtacaagct tctggcagac aaagtggcag   1560
```

```
acatactgtc ccacaaatga agatggaatc tgtaaaagaa aacgcgtgaa ataatgcgtc   1620
tgacaaaggt taggtcggct gcctttaatc aataccaaag tggtcccctac cacgatggaa  1680
aaactgtgca gtcggtttgg cttttctga cgaacaaata agattcgtgg ccgacaggtg   1740
ggggtccacc atgtgaaggc atcttcagac tccaataatg gagcaatgac gtaagggctt  1800
acgaaataag taagggtagt ttgggaaatg tccactcacc cgtcagtcta taaatactta  1860
gccctccct cattgttaag ggagcaagga tccaccatga ctagtaacgg ccgccagtgt   1920
gctggtattc gcccttatga cggccgacaa caacaccgag gcctggacag cagcaccacc  1980
aaggacgtga tccagaaggg catcagcgtg gtgggcgacc tgctgggcgt ggtgggcttc  2040
ccctcggcg gcgccctggt gagcttctac accaacttcc tgaacaccat ctggcccaac  2100
gaggacccct ggaaggcctt catggagcag gtggaggccc tgatggacca gaagatcgcc  2160
gactacgcca agaacaaggc actggccgag ctacagggcc tccagaacaa cgtggaggac  2220
tatgtgagcg ccctgagcag ctggcagaag aaccccgctg caccgttccg caaccccac   2280
agccagggcc gcatccgcga gctgttcagc caggccgaga gccacttccg caacagcatg  2340
cccagcttcg ccatcagcgg ctacgaggtg ctgttcctga ccacctacgc ccaggccgcc  2400
aacacccacc tgttcctgct gaaggacgcc caaatctacg agaggagtg gggctacgag   2460
aaggaggaca tcgccgagtt ctacaagcgc cagctgaagc tgacccagga gtacaccgac  2520
cactgcgtga agtggtacaa cgtgggtcta gacaagctcc gcggcagcag ctacgagagc  2580
tgggtgaact tcaaccgcta ccgccgcgag atgacccgca ccgtgctggg cctgatcgcc  2640
ctgttccccc tgtacgacgt gcgcctgtac cccaaggagg tgaagaccga gctgaccgc   2700
gacgtgctga ccgaccccat cgtgggcgtg aacaacctgc gcggctacgg caccaccttc  2760
agcaacatcg agaactacat ccgcaagccc cacctgttcg actacctgca ccgcatccag  2820
ttccacacgc gtttccagcc cggctactac ggcaacgaca gcttcaacta ctggagcggc  2880
aactacgtga gcaccgcc cagcatcgg agcaacgaca tcatcaccag ccccttctac   2940
ggcaacaaga gcagcgagcc cgtgcagaac cttgagttca acggcgagaa ggtgtaccgc  3000
gccgtggcta acaccaacct ggccgtgtgg ccctctgcag tgtacagcgg cgtgaccaag  3060
gtggagttca gccagtacaa cgaccagacc gacgaggccg accacagac ctacgacgag  3120
aagcgcaacg tgggcgccgt gagctggac agcatcgacc agctgccccc cgagaccacc  3180
gacgagcccc tggagaaggg ctacagccac cagctgaact acgtgatgtg cttcctgatg  3240
cagggcagcc gcggcaccat ccccgtgctg acctggaccc acaagagcgt cgacttcttc  3300
aacatgatcg acagcaagaa gatcacccag ctgcccctga ccaagagcac caacctggcc  3360
agcggcacca gcgtggtgaa gggcccccggc ttcaccggcg gcgacatcct gcgccgcacc  3420
agccccggcc agatcagcac cctgcgcgtg aacatcaccg cccccctgag ccagcgctac  3480
cgcgtccgca tccgctacgc cagcaccacc aacctgcagt tccacaccag catcgacggc  3540
cgcccatca accagggcaa cttcagcgcc accatgagca gcggcagcaa cctgcagagc  3600
ggcagcttcc gcaccgtggg cttcaccacc ccttcaact tcagcaacgg cagcagcgtg  3660
ttcacccctga gcgccacgt gttcaacagc ggcaacgagg tgtacatcga ccgcatcgag  3720
ttcgtgcccg ccgaggtgac cttcgaggcc gagtacgacc tggagagggc tcagaaggcc  3780
gtgaacgagc tgttcaccag cagcaaccag atcggcctga agaccgacgt gaccgactac  3840
cacatcgatc aggtgtagga gctgatctct agatcccga atttccccga tcgttcaaac  3900
atttggcaat aaagtttctt aagattgaat cctgttgccg gtcttgcgat gattatcata  3960
taatttctgt tgaattacgt taagcatgta ataattaaca tgtaatgcat gacgttattt  4020
atgagatggg ttttttatgat tagagtcccg caattataca tttaatacgc gatagaaaac  4080
aaaatatagc gcgcaaacta ggataaaatta tcgcgcgcgg tgtcatctat gttactagat  4140
cgggaattgg gtaccagctt gcatgcctgc agtgcagcgt gacccggtcg tgccctctc   4200
tagagataat gagcattgca tgtctaagtt ataaaaaatt accacatatt ttttttgtca  4260
cacttgtttg aagtgcagtt tatctatctt tatacatata tttaaacttt actctacgaa  4320
taatataatc tatagtacta caataataatc agtgttttag agaatcatat aaatgaacag  4380
ttagacatgg tctaaaggac aattgagtat tttgacaaca ggactctaca gttttatctt  4440
tttagtgtgc atgtgttctc cttttttttt gcaaatagct tcacctatat aatacttcat  4500
ccattttatt agtacatcca tttagggttt agggttaatg gttttatag actaatttttt  4560
ttagtacata tattttattc tatttttagcc tctaaattaa gaaaactaaa actctatttt  4620
agtttttta tttaataatt tagatataaa atagaataaa ataaagtgac taaaaattaa  4680
acaaataccc tttaagaaat taaaaaaact aaggaaacat ttttcttgtt tcgagtagat  4740
aatgccagcc tgttaaacgc cgtcgacgag tctaacggac accaaccagc gaaccagcag  4800
cgtcgcgtcg ggcaagcga agcagacggc acggcatctc tgtcgctgcc tctgaccc   4860
tctcgagagt tccgctccac cgttggactt gctccgctgt cggcatccag aaattgcgtg  4920
gcggagcggc agacgtgagc cggcacggca ggcggcctcc tcctcctctc acggcaccgg  4980
cagctacggg ggattccttt cccaccgctc cttcgctttc ccttcctcgc ccgccgtaat  5040
aaatagacac cccctccaca ccctctttcc ccaacctcgt gttgttcgga gcgcacacac  5100
acacaaccag atctcccca aatccaccg tcggcacctc cgcttcaagg tacgccgtc   5160
gtcctccccc cccccctc tctaccttct ctagatcggc gttccggtcc atggttaggg  5220
cccggtagtt ctacttctgt tcatgttgt gttagatccg tgtttgtgtt agatccgtgc   5280
tgctagcgtt cgtacacgga tgcgacctgt acgtcagaca cgttctgatt gctaacttgc  5340
cagtgttct cttttgggaa tcctgggatg gctctagccc ttccgcagac gggatcgatt  5400
tcatgatttt ttttgtttcg ttgcataggg tttggtttgc ccttttcctt tatttcaata  5460
tatgccgtgc acttgtttgt cgggtcatct tttcatgctt tttttttgtct tggttgtgat  5520
gatgtggtct ggttgggcgg tcgttctaga tcggagtaga attctgtttc aaactacctg  5580
gtggatttat taattttgga tctgtatgtg tgtgccatac atattcatag ttacgaattg  5640
aagatgatgg atggaaatat cgatctagga taggtataca tgttgatcag ggttttactg  5700
atgcatatac agagatgctt tttgttcgct tggttgtgat gatgtggtgt ggttgggcgg  5760
tcgttcattc gttctagatc ggagtagaat actgttcaa actacctggt gtatttatta  5820
attttggaac tgtatgtgtg tgtcatacat cttcatagtt acgagtttaa gatggatgga  5880
aatatcgatc taggataggt atacatgttg atgtgggttt tactgatgca tatacatgat  5940
gtcagca gcatctattc ataatgctcta accttgtga cctatctatt ataataaaca  6000
agtatgtttt ataattattt tgatcttgat atacttggat gatggcatat gcagcagcta  6060
tatgtggatt ttttttagccc tgccttcata cgctattttat ttgcttggta ctgtttcttt  6120
tgtcgatgct caccctgttg tttggtgtta cttctgcagg gatccccgat catgcaaaaa  6180
ctcattaact cagtgcaaaa ctatgcctgg ggcagcaaaa cggcgttgac tgaacttat   6240
ggtatggaaa atccgtccag ccagccgatg gccgagctgt ggatgggcgc acatccgaaa  6300
```

```
agcagttcac gagtgcagaa tgccgccgga gatatcgttt cactgcgtga tgtgattgag   6360
agtgataaat cgactctgct cggagaggcc gttgccaaac gctttggcga actgcctttc   6420
ctgttcaaag tattatgcgc agcacagcca ctctccattc aggttcatcc aaacaaacac   6480
aattctgaaa tcggttttgc caaagaaaat gccgcaggta tcccgatgga tgccgccgag   6540
cgtaactata aagatcctaa ccacaagccg gagctgtttc ttgcgctgac gccttttcctt   6600
gcgatgaacg cgtttcgtga atttccgag attgtctccc tactccagcc ggtcgcaggt   6660
gcacatccgg cgattgctca cttttttacaa cagcctgatg ccgaacgttt aagcgaactg   6720
ttcgccagcc tgttgaatat gcagggtgaa gaaaaatccc gcgcgctggc gatttttaaa   6780
tcggccctcg atagccagca gggtgaaccg tggcaaacga ttcgtttaat ttctgaatttt   6840
tacccggaag acagcggtct gttctccccg ctattgctga atgtggtgaa attgaaccct   6900
ggcgaagcga tgttcctgtt cgctgaaaca ccgcacgctt acctgcaagg cgtggcgctg   6960
gaagtgatgg caaactccga taacgtgctg cgtgcgggtc tgacgcctaa atacattgat   7020
attccggaac tggttgccaa tgtgaaattc gaagccaaac cggctaacca gttgttgacc   7080
cagccggtga aacaaggtgc agaactggac ttcccgattc cagtggatga ttttgccttc   7140
tcgctgcatg accttagtga taaagaaacc accattagcc agcagagtgc cgccattttg   7200
ttctgcgtcg aaggcgatgc aacgttgtgg aaaggttctc agcagttaca gcttaaaccg   7260
ggtgaatcag cgtttattgc cgccaacgaa tcaccggtga ctgtcaaagg ccacggccgt   7320
ttagcggtg tttacaacaa gctgtaagag cttactgaaa aaattaacat ctcttgctaa   7380
gctgggagct cgatccgtcg acctgcagat cgttcaaaca tttggcaata agtttcctta   7440
agattgaatc ctgttgccgg tcttgcgatg attatcatat aatttctgtt gaattacgtt   7500
aagcatgtaa taattaacat gtaatgcatg acgttattta tgagatgggt ttttatgatt   7560
agagtcccgc aattatacat ttaatacgcg atagaaaaca aaatatagcg cgcaaactag   7620
gataaattat cgcgcgcggt gtcatctatg ttactagatc tgctagccct gcaggaaatt   7680
taccggtgcc cgggcggcca gcatggccgt atccgcaatg tgttattaag ttgtctaagc   7740
gtcaatt                                                             7747

SEQ ID NO: 35           moltype = DNA   length = 18
FEATURE                 Location/Qualifiers
source                  1..18
                        mol_type = other DNA
                        organism = synthetic construct
SEQUENCE: 35
tgtttacacc acaatata                                                 18

SEQ ID NO: 36           moltype = DNA   length = 8858
FEATURE                 Location/Qualifiers
source                  1..8858
                        mol_type = other DNA
                        organism = synthetic construct
SEQUENCE: 36
tacaagaata ttgagacgtg agtacatagc attggcattt tcattagcaa gcatttcaaa     60
agaatttaat tttctcatag caatgtgata tctctcctca cgctcaattc tagttccttc    120
atgtagagca catatgtcca tccacaaatc atgacaattt ttatgtttc taactctatt    180
aaacacatct ttgcaaaggc ctctaaaaag ggtgttttg gccttagcat tccatttctc    240
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag gggggttga attgggcttt tctaaaaatc aacactaact aaaatctaag    540
caagagccca acttcacccc gacaactagc actaagagaa taatactaga aatacaacaa    600
tgctaagata atacttcaaa tacttgctaa acaaatacac aatgtaaaat acttgaatta    660
agtgcggaat gtaaagcaag gtttagaaga ctcctccaat tttttctagag gtatcaaaga    720
gtcggcactc tccccctagtc ctcgttggag cacctgcgta agggtatcgc tctcccttgg    780
tcatcgcaag aaccaagtgc tcacaacgag atgatccttt gccactccgg cgcggtggat    840
ccctcacgac cgcttacaaa cttgagtcgg tcaccaaca agatctccac ggtgatcacc    900
gagctcccaa cgccaccaag ccgtctaggt gatgccgatc accaagagta ataagccata    960
gactttcact tgaccaagag aagcctaatg catgcgtgt gtgctctagg tggctctcgc   1020
tagcgttaat gaggtccaaa tgcgggatta agattctcaa gtcacctcac taggctttgt   1080
ggtgcttgca atgctctacc aatgtgtagg agtaaatgtg ggcagcaaga ccatcaatat   1140
ggtaggtgga tgggtataaa atagccctca cccaccaact agcattacc aggaatctgc   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacgaat ttaaactgaa ggcgggaaac gacaatctga   1380
tcatgacgcg agaattaagg gagtcacgtt atgaccccg ccgatgacgc gggacaagcc    1440
gttttacgtt tggaactgac agaaccgcaa cgctgcagga attggccgca gctgccattt   1500
aaatcaattg ggcgcgccga attcgagctc ggtacaagct tctggcagac aaagtggcag   1560
acatactgtc ccacaaatga agatggaatc tgtaaaagaa aacgcgtgaa ataatgcgtc   1620
tgacaaaggt taggtcggct gcctttaatc aataccaaa tggtccctac cacgatggaa   1680
aaactgtgca gtcggtttgg cttttttctga cgaacaaata agattcgtgg ccgacaggtg   1740
ggggtccacc atgtgaaggc atcttcgac tccaataatg gagcaatgac gtaagggctt   1800
acgaaataag taagggtagt ttgggaaatg tccactcacc cgtcagtcta taatactta    1860
gcccctccct cattgttaag ggagcaagga tccaccatga ctagtaacgg ccgccagtgt   1920
gctggtattc gcccttatga cggccgacaa caacaccgag gcctggacag cagcaccacc   1980
aaggacgtga tccagaaggg catcagcgtg gtgggcgtg gtggggcttc                2040
cccttcggcg gcgccctggt gagcttctac accaacttcc tgaacaccat ctggcccagc   2100
gaggacccct ggaaggcctt catggagcag gtggaggccc tgatgaccca aagatcgcc    2160
gactacgcca gaacaaggc actggccgag ctacagggcc tccagaacaa cgtggaggac   2220
tatgtgagcg ccctgagcag ctggcagaag aaccccgctg caccgttccg caacccccac   2280
agccagggcc gcatccgcga gctgttcagc caggccgaga gccacttccg caacagcatg   2340
```

```
cccagcttcg ccatcagcgg ctacgaggtg ctgttcctga ccacctacgc ccaggccgcc   2400
aacacccacc tgttcctgct gaaggacgcc caaatctacg gagaggagtg gggctacgag   2460
aaggaggaca tcgccgagtt ctacaagcgc cagctgaagc tgacccagga gtacaccgac   2520
cactgcgtga agtggtacaa cgtgggtcta gacaagctcc gcggcagcag ctacgagagc   2580
tgggtgaact tcaaccgcta ccgccgcgag atgaccctga ccgtgctgag cctgatcgcc   2640
ctgttccccc tgtacgacgt gcgcctgtac cccaaggagg tgaagaccga gctgaccgc    2700
gacgtgctga ccgaccccat cgtgggcgtg aacaacctgc gcggctacgg caccaccttc   2760
agcaacatcg agaactacat ccgcaagccc cacctgttcg actacctgca ccgcatccag   2820
ttccacacgc gtttccagcc cggctactac ggcaacgaca gcttcaacta ctggagcggc   2880
aactacgacg gcacccgccc cagcatcggc agcaacgaca tcatcaccag ccccttctac   2940
ggcaacaaga gcagcgagcc cgtgcagaac cttgagttca acggcgagaa ggtgtaccgc   3000
gccgtggcta acaccaacct ggccgtgtgg ccctctgcag tgtacagcgg cgtgaccaag   3060
gtggagttca gccagtacaa cgaccagacc gacgaggcca gcacccagac ctacgacagc   3120
aagcgcaacg tgggcgccgt gagctgggac agcatcgacc agctgccccc cgagaccacc   3180
gacgagcccc tggagaaggg ctacagccac cagctgaact acgtgatgtg cttcctgatg   3240
cagggcagcc gcggcaccat ccccgtgctg acctggaccc acaagagcgt cgacttcttc   3300
aacatgatcg acagcaagaa gatcacccag ctgcccctga ccaagagcac caacctgggc   3360
agcggcacca gcgtggtgaa gggccccggc ttcaccgacg gcgacatcct gcgccgcacc   3420
agccccggcc agatcagcac cctgcgcgtg aacatcaccg cccccctgag ccagcgctac   3480
cgcgtccgca tccgctacgc cagcaccacc aacctgcagt tccacaccag catcgacggc   3540
cgccccatca accagggcaa cttcagcgcc accatgagca gcggcagcaa cctgcagagc   3600
ggcagcttcc gcaccgtggg cttcaccacc cccttcaacc tcagcaacgg cagcagcgtg   3660
ttcaccctga gcgccacgt gttcaacagc ggcaacgagg tgtacatcga ccgcatcgag   3720
ttcgtgcccg ccgaggtgac cttcgaggcc gagtacgacc tggagagggc tcagaaggcc   3780
gtgaacgagc tgttcaccag cagcaaccag atcggcctga agaccgacgt gaccgactac   3840
cacatcgatc aggtgtagga gctgagctct agatccccga atttcccga tcgttcaaac   3900
atttggcaat aaagtttctt aagattgaat cctgttgccg gtcttgcgat gattatcata   3960
taatttctgt tgaattacgt taagcatgta ataattaaca tgtaatgcat gacgttattt   4020
atgagatggg tttttatgat tagagtcccg caattataca tttaatacgc gatagaaaac   4080
aaaatatagc gcgcaaacta ggataaaatta tcgcgcgcgg tgtcatctat gttactagat   4140
cgggaattgg gtaccagctt gcatgcctgc agtgcagcgt gacccggtcg tgccctctc    4200
tagagataat gagcattgca tgtctaagtt ataaaaaatt accacatatt ttttttgtca   4260
cacttgtttg aagtgcagtt tatctatctt tatacatata tttaaacttt actctacgaa   4320
taatataatc tatagtacta caataatatc agtgttttaga agaatcatat aaatgaacag   4380
ttagacatgg tctaaaggac aattgagtat tttgacaaca ggactctaca gttttatctt   4440
tttagtgtgc atgtgttctc cttttttttt gcaaatagct tcacctatat aatacttcat   4500
ccatttatt agtacatcca tttagggttt agggttaatg gttttatag actaattttt    4560
ttagtacatc tattttattc tattttagcc tctaaattaa gaaaactaaa actctatttt   4620
agtttttta tttaataatt tagatataaa atagaataaa ataaagtgac taaaaattaa   4680
acaaatacc tttaagaaat taaaaaaact aaggaaacat ttttcttgtt tcgagtagat    4740
aatgccagcc tgttaaacgc cgtcgacgag tctaacggac caaccagc gaaccagcag     4800
cgtcgcgtcg ggccaagcga agcagacggc acggcatctc tgtcgctgcc tctggacccc   4860
tctcgagagt tccgctccac cgttggactt gctccgctgt cggcatccag aaattgcgtg   4920
gcggagcggc agacgtgagc cggcacggca ggcggcctcc tcctcctctc acggcaccgg   4980
cagctacggg ggattccttt cccaccgctc cttgcctttc cctccctcgc ccgccgtaat   5040
aaatagacac ccctccaca ccctcttcc ccaacctcgt gttgttcgga gcgcacacac    5100
acacaccag atctccccca aatccacccg tcggcacctc gcttcaagg tacgccgtc     5160
gtcctccccc ccccccctc tctaccttct ctagatcggc gttccggtcc atggttaggg   5220
cccggtagtt ctacttctgt tcatgttttgt gttagatccg tgtttgtgtt agatccgtgc   5280
tgctagcgtt cgtacacgga tgcgacctgt acgtcagaca cgttctgatt gctaacttgc   5340
cagtgttttct ctttggggaa tcctgggatg gctctagccg ttccgcagac gggatcgatt   5400
tcatgatttt ttttgtttcg ttgcataggg tttggtttgc cctttccttt tatttcaata   5460
tatgccgtgc acttgtttgt cgggtcatct tttcatgctt ttttttgtct tggttgtgat   5520
gatgtggtct ggttgggcgg tcgttctaga tcggagtaga attctgtttc aaactacctg   5580
gtggatttat taatttgga tctgtatgtg tgtgccatac atattcatag ttacgaattg    5640
aagatgatgg atggaaatat cgatctagga taggtataca tgttgatgcg ggttttactg   5700
atgcatatac agagatgctt tttgttcgct tggttgtgat gatgtggtgt ggttgggcgg   5760
tcgttcattc gttctagatc ggagtagaat actgtttcaa actaccggt gtatttatta    5820
attttggaac tgtatgtgtg tgtcatacat cttcatagtt acgagtttaa gatggatgga   5880
aatatcgatc taggataggt atacatgttg atgtgggttt tactgatgca tatacatgat   5940
ggcatatgca gcatctattc atatgctcta accttgagta cctatctatt ataataaaca   6000
agtatgtttt ataattattt tgatcttgat atacttggat gatggcatat gcagcagcta   6060
tatgtggatt ttttttagccc tgccttcata cgctatttat ttgcttggta ctgtttcttt   6120
tgtcgatgct caccctgttg ttttggtgtta cttctgcagg gatccccgat catgcaaaaa   6180
ctcattaact cagtgcaaaa ctatgcctgg ggcagcaaaa ccgcgttgac tgaactttat   6240
ggtatggaaa atccgtccag ccagccgatg gccgagctgt ggatgggcgc acatccgaaa   6300
agcagttcac gagtgcagaa tgccgccgga gatatcgttt cactgcgtga tgtgattgag   6360
agtgataaat cgactctgct cggagaggcc gttgccaaac gcttttggcga actgcctttc   6420
ctgttcaaag tattatgcgc agcacagcca ctctccattc aggttcatcc aaacaaacac   6480
aattctgaaa tcggtttgc caaagaaaat gccgcaggta tcccgatgga tgccgccgag   6540
cgtaactata aagatcctaa ccacaagccg gactgttt ttgcgctgac gccttttcctt    6600
gcgatgaacg cgtttcgtga atttttccgag attgtctccc tactccagcc ggtcgcaggt   6660
gcacatccgg cgattgctca cttttttacaa cagcctgatg ccgaacgttt aagcgaactg   6720
ttcgccagcc tgttgaatat gcagggtgaa gaaaaatccc gccgctggc gattttaaaa   6780
tcggccctcg atagccagca gggtgaaccg tggcaaacga ttcgtttaat ttctgaatt   6840
taccggaag acagcggtct gttctccccg ctattgctga atgtggtgaa attgaacctt   6900
ggcgaagcga tgttcctgtt cgctgaaaca ccgcacgctt acctgcaagg cgtggcgctg   6960
gaagtgatgg caaactccga taacgtgctg cgtgcgggtc tgacgcctaa atacattgat   7020
attccggaac tggttgccaa tgtgaaattc gaagccaaac cggctaacca gttgttgacc   7080
```

```
cagccggtga acaaggtgc agaactggac ttcccgattc cagtggatga ttttgccttc    7140
tcgctgcatg accttagtga taaagaaacc accattagcc agcagagtgc cgccattttg    7200
ttctgcgtcg aaggcgatgc aacgttgtgg aaaggttctc agcagttaca gcttaaaccg    7260
ggtgaatcag cgtttattgc cgccaacgaa tcaccggtga ctgtcaaagg ccacggccgt    7320
ttagcgcgtg tttacaacaa gctgtaagag cttactgaaa aaattaacat ctcttgctaa    7380
gctgggagct cgatccgtcg acctgcagat cgttcaaaca tttggcaata aagtttctta    7440
agattgaatc ctgttgccgg tcttgcgatg attatcatat aatttctgtt gaattacgtt    7500
aagcatgtaa taattaacat gtaatgcatg acgttattta tgagatgggt tttatgatt    7560
agagtcccgc aattatacat ttaatacgcg atagaaaaca aaatatagcg cgcaaactga    7620
gataaattat cgcgcgcggt gtcatctatg ttactagatc tgctagccct gcaggaaatt    7680
taccggtgcc cgggcggcca gcatggccgt atccgcaatg tgttattaag ttgtctaagc    7740
gtcaatttgt ttacaccaca atatacctc ttccctgggc caggctgggc ccactggcaa    7800
agggtgcacc ggacagtccg gtgccccaaa gccagaaacc ctagcttctg ttttgtgctg    7860
tttttcaat ttggttttg ttctaacttg tgagtatgt ctagagttac acctagcact    7920
atatgtgagt gtgaatatgc accaacacta cactagaact cttttggtca aactactat    7980
cgacaacccc tctttatagt acggctaaaa caaaataaaa gacctaacta tatcacgagt    8040
gtccgcaact ccttgacact cggaatacga agaccttcac tttttgtttc gtcgtttag    8100
ccgttgcttc aagtttttat ctcgggatt gttttcacca ttgtagtaca tctacctgta    8160
atgcgacct aacttaccatt tgcctctgca aaacacatgt tagtcacata taaaattacg    8220
ttgtcattaa tcactaaaac caaccagggg cctagatgct ttctagtta aatccccaac    8280
aagtcaaaat tctttctatt tttttttgca agttccaatt gacatctgaa aggttgtaag    8340
gtacacgtt ggctctcatt gataacgggg gaaagataca gtgcaaacca ccatataatg    8400
acccactct aatcgaatgg acctgtaacg acgaaatacc ctgtgagaac tatggttcac    8460
tcatgttaat tcattgaaat tgttgtagtg aattgacatg gttgggagcc tgcttagaga    8520
gtatagattg tcactttttt ttggaccgca acttatttt aaaagatatt gcgatcgctt    8580
gtttagtagc tgtttcaggc cccaatgcag tttctatcgt gatccattta agtcactcaa    8640
cattctcata cttctcattt tgcattaatt cattccaatc tccactacta taaaatacta    8700
gcttcgatgg tcgtcatacg ccatgcacga agcatgtaga tcaatccgca taccagtggg    8760
catctataga taggctgtga aaaccaccca aatccctact agtggacatt ttatctatag    8820
atggaccgtg agaaaccaca caagtctaac acgacagg                             8858

SEQ ID NO: 37           moltype = AA   length = 1307
FEATURE                 Location/Qualifiers
source                  1..1307
                        mol_type = protein
                        organism = unidentified
SEQUENCE: 37
MTQFEGFTNL YQVSKTLRFE LIPQGKTLKH IQEQGFIEED KARNDHYKEL KPIIDRIYKT     60
YADQCLQLVQ LDWENLSAAI DSYRKEKTEE TRNALIEEQA TYRNAIHDYF IGRTDNLTDA    120
INKRHAEIYK GLFKAELFNG KVLKQLGTVT TTEHENALLR SFDKFTTYFS GFYENRKNVF    180
SAEDISTAIP HRIVQDNFPK FKENCHIFTR LITAVPSLRE HFENVKKAIG IFVSTSIEEV    240
FSFPFYNQLL TQTQIDLYNQ LLGGISREAG TEKIKGLNEV LNLAIQKNDE TAHIIASLPH    300
RFIPLFKQIL SDRNTLSFIL EEFKSDEEVI QSFCKYKTLL RNENVLETAE ALFNELNSID    360
LTHIFISHKK LETISSALCD HWDTLRNALY ERRISELTGK ITKSAKEKVQ RSLKHEDINL    420
QEIISAAGKE LSEAFKQKTS EILSHAHAAL DQPLPTTLKK QEEKEILKSQ LDSLLGLYHL    480
LDWFAVDESN EVDPEFSARL TGIKLEMEPS LSFYNKARNY ATKKPYSVEK FKLNFQMPTL    540
ASGWDVNKEK NNGAILFVKN GLYYLGIMPK QKGRYKALSF EPTEKTSEGF DKMYYDYFPD    600
AAKMIPKCST QLKAVTAHFQ THTTPILLSN NFIEPLEITK EIYDLNNPEK EPKKFQTAYA    660
KKTGDQKGYR EALCKWIDFT RDFLSKYTKT TSIDLSSLRP SSQYKDLGEY YAELNPLLYH    720
ISFQRIAEKE IMDAVETGKL YLFQIYNKDF AKGHHGKPNL HTLYWTGLFS PENLAKTSIK    780
LNGQAELFYR PKSRMKRMAH RLGEKMLNKK LKDQKTPIPD TLYQELYDYV NHRLSHDLSD    840
EARALLPNVI TKEVSHEIIK DRRFTSDKFF FHVPITLNYQ AANSPSKFNQ RVNAYLKEHP    900
ETPIIGIDRG ERNLIYITVI DSTGKILEQR SLNTIQQFDY QKKLDNREKE RVAARQAWSV    960
VGTIKDLKQG YLSQVIHEIV DLMIHYQAVV VLENNLFGFK SKRTGIAEKA VYQQFEKMLI   1020
DKLNCLVLKD YPAEKVGGVL NPYQLTDQFT SFAKMGTQSG FLFYVPAPYT SKIDPLTGFV   1080
DPFVWKTIKN HESRKHFLEG FDFLHYDVKT GDFILHFKMN RNLSFQRGLP GFMPAWDIVF   1140
EKNETQFDAK GTPFIAGKRI VPVIENHRFT GRYDLYPAN ELIALLEEKG IVFRDGSNIL   1200
PKLLENDDSH AIDTMVALIR SVLQMRNSNA ATGEDYINSP VRDLNGVCFD SRFQNPEWPM   1260
DADANGAYHI ALKGQLLLNH LKESKDLKLQ NGISNQDWLA YIQELRN                 1307

SEQ ID NO: 38           moltype = DNA   length = 13
FEATURE                 Location/Qualifiers
source                  1..13
                        mol_type = other DNA
                        organism = synthetic construct
SEQUENCE: 38
acgaatttaa act                                                        13

SEQ ID NO: 39           moltype = DNA   length = 19
FEATURE                 Location/Qualifiers
source                  1..19
                        mol_type = other DNA
                        organism = synthetic construct
SEQUENCE: 39
gcctctaaac acgaactga                                                  19

SEQ ID NO: 40           moltype = DNA   length = 20
FEATURE                 Location/Qualifiers
source                  1..20
```

```
                        mol_type = other DNA
                        organism = synthetic construct
SEQUENCE: 40
tcgttcaaac attaacatct                                            20

SEQ ID NO: 41           moltype = DNA  length = 25
FEATURE                 Location/Qualifiers
source                  1..25
                        mol_type = other DNA
                        organism = synthetic construct
SEQUENCE: 41
tgctgcgcat gggcgcaccg gacag                                      25

SEQ ID NO: 42           moltype = DNA  length = 25
FEATURE                 Location/Qualifiers
source                  1..25
                        mol_type = other DNA
                        organism = synthetic construct
SEQUENCE: 42
caattcctgc agcgttgcgg ttctg                                      25
```